(12) United States Patent
Watt et al.

(10) Patent No.: US 8,063,012 B2
(45) Date of Patent: Nov. 22, 2011

(54) NEUROPROTECTIVE PEPTIDE INHIBITORS OF AP-1 SIGNALING AND USES THEREFOR

(75) Inventors: Paul Watt, Perth (AU); Nadia Milech, Perth (AU); Mark Fear, Perth (AU)

(73) Assignee: Phylogica Limited, Subiaco (AU)

( * ) Notice: Subject to any disclaimer, the term of this patent is extended or adjusted under 35 U.S.C. 154(b) by 0 days.

(21) Appl. No.: 12/441,695

(22) PCT Filed: Jan. 31, 2007

(86) PCT No.: PCT/AU2007/000092
§ 371 (c)(1),
(2), (4) Date: Apr. 12, 2010

(87) PCT Pub. No.: WO2008/034161
PCT Pub. Date: Mar. 27, 2008

(65) Prior Publication Data
US 2010/0190698 A1    Jul. 29, 2010

Related U.S. Application Data

(60) Provisional application No. 60/826,208, filed on Sep. 19, 2006.

(51) Int. Cl.
*C07K 14/47* (2006.01)
(52) U.S. Cl. .......................................... 514/1.1; 530/350
(58) Field of Classification Search .................. None
See application file for complete search history.

(56) References Cited

U.S. PATENT DOCUMENTS

| 5,843,698 A | 12/1998 | Sorensen |
| 6,074,815 A | 6/2000 | Sorensen |
| 6,150,127 A | 11/2000 | Sorensen |
| 2007/0031832 A1 | 2/2007 | Watt |
| 2007/0060514 A1 | 3/2007 | Bonny |

FOREIGN PATENT DOCUMENTS

| CN | 1629637 | 6/2005 |
| EP | 1776958 A2 | 4/2007 |
| EP | 1811033 A1 | 7/2007 |
| WO | WO 01/32156 A2 | 5/2001 |
| WO | WO 2004/074479 A1 | 9/2004 |
| WO | WO 2006/017913 A1 | 2/2006 |
| WO | WO 2007/031098 A1 | 3/2007 |
| WO | WO 2008/034161 A1 | 3/2008 |
| WO | WO 2008/034162 A1 | 3/2008 |
| WO | WO 2008/154700 A1 | 12/2008 |

OTHER PUBLICATIONS

Bennett, B.L., "c-Jun N-Terminal Kinase-Dependent Mechanisms in Respiratory Disease," Eur. Respir. Journal, 2006, pp. 651-661, vol. 28.
Florin, I. et al., "Identification of Novel AP-1 Target Genes in Fibroblasts Regulated During Cutaneous Wound Healing," Oncogene, 2004, pp. 7005-7017, vol. 23, No. 42.
Nguyen, C. et al., "Chemogenomic Identification of Ref-1/AP-1 as a Therapeutic Target for Asthma," Proc. Nat. Acad. Sci., Feb. 4, 2003, pp. 1169-1173, vol. 100, No. 3.
PCT International Search Report, PCT Application No. PCT/AU2007/000092, Apr. 2, 2007, 3 pages.
PCT International Preliminary Examination Report, PCT Application No. PCT/AU2007/000092, Mar. 24, 2009, 7 pages.
PCT International Search Report and Written Opinion, PCT Application No. PCT/AU2007/000121, Apr. 5, 2007, 8 pages.
PCT International Preliminary Examination Report, PCT Application No. PCT/AU2007/000121, Mar. 24, 2009, 4 pages.
PCT International Search Report and Written Opinion, PCT Application No. PCT/AU2008/000903, Oct. 15, 2008, 13 pages.
PCT International Preliminary Report on Patentability, PCT Application No. PCT/AU2008/000903, Dec. 22, 2009, 7 pages.
RefSeq Accession No. XP_975325.1, NCBI Sequence Viewer v2.0, 1 page, [Online] [Retrieved on May 3, 2007].
RefSeq Accession No. ZP_01044355.1, NCBI Sequence Viewer v2.0, 2 pages, [Online] [Retrieved on May 3, 2007].
RefSeq Accession No. YP_284595.1, NCBI Sequence Viewer v2.0, 2 pages, [Online] [Retrieved on May 3, 2007].
Yates, S. et al."Transcription Factor Activation in Response to Cutaneous Injury: Role of AP-1 in Reepithelialization," Wound Repair Regeneration, 2002, pp. 5-15, vol. 10, No. 1.

*Primary Examiner* — John Ulm
(74) *Attorney, Agent, or Firm* — Fenwick & West LLP

(57) ABSTRACT

The present invention provides AP-1 signaling inhibitory peptides of SEQ ID NOS:54-57, compositions of the peptides, and methods of treatment of neurological disorders by administration of the peptide(s) or compositions.

11 Claims, 18 Drawing Sheets

```
                        SEQUENCE LISTING

<160> NUMBER OF SEQ ID NOS: 68

<210> SEQ ID NO 1
<211> LENGTH: 10
<212> TYPE: PRT
<213> ORGANISM: artificial
<220> FEATURE:
<223> OTHER INFORMATION: HIV tat basic region protein transduction
      domain

<400> SEQUENCE: 1

Gly Arg Lys Lys Arg Arg Gln Arg Arg Arg
1               5                   10

<210> SEQ ID NO 2
<211> LENGTH: 11
<212> TYPE: PRT
<213> ORGANISM: artificial
<220> FEATURE:
<223> OTHER INFORMATION: HIV tat basic region protein transduction
      domain

<400> SEQUENCE: 2

Gly Arg Lys Lys Arg Arg Gln Arg Arg Arg Pro
1               5                   10

<210> SEQ ID NO 3
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 3

Gly Arg Lys Lys Arg Arg Gln Arg Arg Arg Pro Pro
1               5                   10

<210> SEQ ID NO 4
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 4

Gly Arg Lys Lys Arg Arg Gln Arg Arg Arg Pro Pro Gln
1               5                   10

<210> SEQ ID NO 5
<211> LENGTH: 11
<212> TYPE: PRT
<213> ORGANISM: artificial
<220> FEATURE:
<223> OTHER INFORMATION: HIV tat basic region protein transduction
      domain
```

-continued

<400> SEQUENCE: 5

Gly Arg Lys Lys Arg Arg Gln Arg Arg Gly
1               5                   10

<210> SEQ ID NO 6
<211> LENGTH: 12
<212> TYPE: PRT
<213> ORGANISM: artificial
<220> FEATURE:
<223> OTHER INFORMATION: HIV tat basic region protein transduction
      domain

<400> SEQUENCE: 6

Gly Arg Lys Lys Arg Arg Gln Arg Arg Arg Pro Gly
1               5                   10

<210> SEQ ID NO 7
<211> LENGTH: 13
<212> TYPE: PRT
<213> ORGANISM: artificial
<220> FEATURE:
<223> OTHER INFORMATION: HIV tat basic region protein transduction
      domain

<400> SEQUENCE: 7

Gly Arg Lys Lys Arg Arg Gln Arg Arg Arg Pro Pro Gly
1               5                   10

<210> SEQ ID NO 8
<211> LENGTH: 14
<212> TYPE: PRT
<213> ORGANISM: artificial
<220> FEATURE:
<223> OTHER INFORMATION: HIV tat basic region protein transduction
      domain

<400> SEQUENCE: 8

Gly Arg Lys Lys Arg Arg Gln Arg Arg Arg Pro Pro Gln Gly
1               5                   10

<210> SEQ ID NO 9
<211> LENGTH: 10
<212> TYPE: PRT
<213> ORGANISM: artificial
<220> FEATURE:
<223> OTHER INFORMATION: retroinverted HIV tat basic region protein
      transduction domain wherein all amino acids other than glycine
      are D-amino acids

<400> SEQUENCE: 9

Arg Arg Arg Gln Arg Arg Lys Lys Arg Gly
1               5                   10

<210> SEQ ID NO 10
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 10

Pro Arg Arg Arg Gln Arg Arg Lys Lys Arg Gly
1               5                   10

<210> SEQ ID NO 11

-continued

```
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 11

Pro Pro Arg Arg Arg Gln Arg Arg Lys Lys Arg Gly
1               5                   10

<210> SEQ ID NO 12
<211> LENGTH: 13
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 12

Gln Pro Pro Arg Arg Arg Gln Arg Arg Lys Lys Arg Gly
1               5                   10

<210> SEQ ID NO 13
<211> LENGTH: 11
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 13

Gly Arg Arg Arg Gln Arg Arg Lys Lys Arg Gly
1               5                   10

<210> SEQ ID NO 14
<211> LENGTH: 12
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 14

Gly Pro Arg Arg Arg Gln Arg Arg Lys Lys Arg Gly
1               5                   10

<210> SEQ ID NO 15
<211> LENGTH: 13
<212> TYPE: PRT
<213> ORGANISM: artificial
<220> FEATURE:
<223> OTHER INFORMATION: retroinverted HIV tat basic region protein
      transduction domain wherein all amino acids other than glycine are
      D-amino acids

<400> SEQUENCE: 15

Gly Pro Pro Arg Arg Arg Gln Arg Arg Lys Lys Arg Gly
1               5                   10

<210> SEQ ID NO 16
<211> LENGTH: 14
<212> TYPE: PRT
<213> ORGANISM: artificial
<220> FEATURE:
<223> OTHER INFORMATION: retroinverted HIV tat basic region protein
``` transduction domain wherein all amino acids other than glycine are
D-amino acids

<400> SEQUENCE: 16

Gly Gln Pro Pro Arg Arg Gln Arg Arg Lys Lys Arg Gly
1               5                   10

<210> SEQ ID NO 17
<211> LENGTH: 12
<212> TYPE: PRT
<213> ORGANISM: artificial
<220> FEATURE:
<223> OTHER INFORMATION: Kaposi fibroblast growth factor (FGF)
      hydrophobic peptide protein transduction domain

<400> SEQUENCE: 17

Ala Ala Val Leu Leu Pro Val Leu Leu Ala Ala Pro
1               5                   10

<210> SEQ ID NO 18
<211> LENGTH: 13
<212> TYPE: PRT
<213> ORGANISM: artificial
<220> FEATURE:
<223> OTHER INFORMATION: Kaposi fibroblast growth factor (FGF)
      hydrophobic peptide protein transduction domain

<400> SEQUENCE: 18

Gly Ala Ala Val Leu Leu Pro Val Leu Leu Ala Ala Pro
1               5                   10

<210> SEQ ID NO 19
<211> LENGTH: 12
<212> TYPE: PRT
<213> ORGANISM: artificial
<220> FEATURE:
<223> OTHER INFORMATION: retroinverted Kaposi FGF hydrophobic
      peptide protein transduction domain

<400> SEQUENCE: 19

Pro Ala Ala Leu Leu Val Pro Leu Leu Val Ala Ala
1               5                   10

<210> SEQ ID NO 20
<211> LENGTH: 13
<212> TYPE: PRT
<213> ORGANISM: artificial
<220> FEATURE:
<223> OTHER INFORMATION: retroinverted Kaposi FGF hydrophobic peptide
      protein transduction domain

<400> SEQUENCE: 20

Pro Ala Ala Leu Leu Val Pro Leu Leu Val Ala Ala Gly
1               5                   10

<210> SEQ ID NO 21
<211> LENGTH: 27
<212> TYPE: PRT
<213> ORGANISM: ARTIFICIAL
<220> FEATURE:
<223> OTHER INFORMATION: signal sequence based peptide 1

<400> SEQUENCE: 21

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

```
<210> SEQ ID NO 22
<211> LENGTH: 16
<212> TYPE: PRT
<213> ORGANISM: ARTIFICIAL
<220> FEATURE:
<223> OTHER INFORMATION: signal sequence based peptide 2

<400> SEQUENCE: 22

Ala Ala Val Ala Leu Leu Pro Ala Val Leu Leu Ala Leu Leu Ala Pro
1               5                   10                  15

<210> SEQ ID NO 23
<211> LENGTH: 26
<212> TYPE: PRT
<213> ORGANISM: ARTIFICIAL
<220> FEATURE:
<223> OTHER INFORMATION: transportan protein transduction domain

<400> SEQUENCE: 23

Gly Trp Thr Leu Asn Ser Ala Gly Tyr Leu Leu Lys Ile Asn Leu Lys
1               5                   10                  15

Ala Leu Ala Ala Leu Ala Lys Lys Ile Leu
            20                  25

<210> SEQ ID NO 24
<211> LENGTH: 18
<212> TYPE: PRT
<213> ORGANISM: ARTIFICIAL
<220> FEATURE:
<223> OTHER INFORMATION: amphiphilic model peptide

<400> SEQUENCE: 24

Lys Leu Ala Leu Lys Leu Ala Leu Lys Ala Leu Lys Ala Ala Leu Lys
1               5                   10                  15

Leu Ala

<210> SEQ ID NO 25
<211> LENGTH: 9
<212> TYPE: PRT
<213> ORGANISM: ARTIFICIAL
<220> FEATURE:
<223> OTHER INFORMATION: polyarginine protein transduction domain

<400> SEQUENCE: 25

Arg Arg Arg Arg Arg Arg Arg Arg Arg
1               5

<210> SEQ ID NO 26
<211> LENGTH: 69
<212> TYPE: DNA
<213> ORGANISM: artificial
<220> FEATURE:
<223> OTHER INFORMATION: DNA encoding FLAG-PYC19 peptide

<400> SEQUENCE: 26
aggtcagact acaaggacga cgacgacaag cttatcaatc aatcatacgc ataccettac      60 atttactaa                                                             69

<210> SEQ ID NO 27
<211> LENGTH: 22
<212> TYPE: PRT
<213> ORGANISM: artificial
<220> FEATURE:
<223> OTHER INFORMATION: FLAG-PYC19 peptide

<400> SEQUENCE: 27
```

-continued

```
Arg Ser Asp Tyr Lys Asp Asp Asp Lys Leu Ile Asn Gln Ser Tyr
1               5                   10                  15

Ala Tyr Pro Tyr Ile Tyr
            20

<210> SEQ ID NO 28
<211> LENGTH: 12
<212> TYPE: PRT
<213> ORGANISM: artificial
<220> FEATURE:
<223> OTHER INFORMATION: PYC19L peptide

<400> SEQUENCE: 28

Leu Ile Asn Gln Ser Tyr Ala Tyr Pro Tyr Ile Tyr
1               5                   10

<210> SEQ ID NO 29
<211> LENGTH: 13
<212> TYPE: PRT
<213> ORGANISM: artificial
<220> FEATURE:
<223> OTHER INFORMATION: PYC19D peptide (the retroinverted form of
      PYC19L, peptide wherein all amino acids other than glycine are
      D-amino acids with a C-terminal glyine linker added)

<400> SEQUENCE: 29

Tyr Ile Tyr Pro Tyr Ala Tyr Ser Gln Asn Ile Leu Gly
1               5                   10

<210> SEQ ID NO 30
<211> LENGTH: 23
<212> TYPE: PRT
<213> ORGANISM: artificial
<220> FEATURE:
<223> OTHER INFORMATION: PYC19L-TAT peptide (peptide PYC19L with an
      N-terminal TAT basic region protein transduction domain peptide)

<400> SEQUENCE: 30

Gly Arg Lys Lys Arg Arg Gln Arg Arg Gly Leu Ile Asn Gln Ser
1               5                   10                  15

Tyr Ala Tyr Pro Tyr Ile Tyr
            20

<210> SEQ ID NO 31
<211> LENGTH: 23
<212> TYPE: PRT
<213> ORGANISM: artificial
<220> FEATURE:
<223> OTHER INFORMATION: PYC19D-TAT peptide (the retroinverted form of
      PYC19L-TAT peptide wherein all amino acids other than glycine are
      D-amino acids)

<400> SEQUENCE: 31

Tyr Ile Tyr Pro Tyr Ala Tyr Ser Gln Asn Ile Leu Gly Arg Arg
1               5                   10                  15

Gln Arg Arg Lys Lys Arg Gly
            20

<210> SEQ ID NO 32
<211> LENGTH: 25
<212> TYPE: PRT
<213> ORGANISM: artificial
<220> FEATURE:
<223> OTHER INFORMATION: PYC19L-FM peptide (peptide PYC19L with a
      C-terminal Kaposi FGF protein transduction domain)

<400> SEQUENCE: 32
```

```
Leu Ile Asn Gln Ser Tyr Ala Tyr Pro Tyr Ile Tyr Gly Ala Ala Val
1               5                   10                  15

Leu Leu Pro Val Leu Leu Ala Ala Pro
            20                  25

<210> SEQ ID NO 33
<211> LENGTH: 25
<212> TYPE: PRT
<213> ORGANISM: artificial
<220> FEATURE:
<223> OTHER INFORMATION: PYC19D-FM peptide (the retroinverted form of
      PYC19L-FM wherein all amino acids other than glycine are D-amino
      acids)

<400> SEQUENCE: 33

Pro Ala Ala Leu Leu Val Pro Leu Leu Val Ala Ala Gly Tyr Ile Tyr
1               5                   10                  15

Pro Tyr Ala Tyr Ser Gln Asn Ile Leu
            20                  25

<210> SEQ ID NO 34
<211> LENGTH: 87
<212> TYPE: DNA
<213> ORGANISM: artificial
<220> FEATURE:
<223> OTHER INFORMATION: DNA encoding FLAG-PYC35 peptide

<400> SEQUENCE: 34
aggtcagact acaaggacga cgacgacaag gcttatcaat caatcaggtc tggagggata      60
gagtcgagtt cgaaaaggga aaggtag                                         87

<210> SEQ ID NO 35
<211> LENGTH: 28
<212> TYPE: PRT
<213> ORGANISM: artificial
<220> FEATURE:
<223> OTHER INFORMATION: FLAG-PYC35 peptide

<400> SEQUENCE: 35

Arg Ser Asp Tyr Lys Asp Asp Asp Lys Ala Tyr Gln Ser Ile Arg
1               5                   10                  15

Ser Gly Gly Ile Glu Ser Ser Ser Lys Arg Glu Arg
            20                  25

<210> SEQ ID NO 36
<211> LENGTH: 18
<212> TYPE: PRT
<213> ORGANISM: artificial
<220> FEATURE:
<223> OTHER INFORMATION: PYC35L peptide

<400> SEQUENCE: 36

Ala Tyr Gln Ser Ile Arg Ser Gly Gly Ile Glu Ser Ser Ser Lys Arg
1               5                   10                  15

Glu Arg

<210> SEQ ID NO 37
<211> LENGTH: 19
<212> TYPE: PRT
<213> ORGANISM: artificial
<220> FEATURE:
<223> OTHER INFORMATION: PYC35D peptide (the retroinverted form of
      PYC35L, peptide wherein all amino acids other than glycine are
      D-amino acids with a C-terminal glyine linker added)
```

```
<400> SEQUENCE: 37

Arg Glu Arg Lys Ser Ser Ser Glu Ile Gly Gly Ser Arg Ile Ser Gln
1               5                   10                  15

Tyr Ala Gly

<210> SEQ ID NO 38
<211> LENGTH: 29
<212> TYPE: PRT
<213> ORGANISM: artificial
<220> FEATURE:
<223> OTHER INFORMATION: PYC35L-TAT peptide (peptide PYC35L with an
      N-terminal TAT basic region protein transduction domain peptide)

<400> SEQUENCE: 38

Gly Arg Lys Lys Arg Arg Gln Arg Arg Gly Ala Tyr Gln Ser Ile
1               5                   10                  15

Arg Ser Gly Gly Ile Glu Ser Ser Ser Lys Arg Glu Arg
                20                  25

<210> SEQ ID NO 39
<211> LENGTH: 29
<212> TYPE: PRT
<213> ORGANISM: artificial
<220> FEATURE:
<223> OTHER INFORMATION: PYC35D-TAT peptide (the retroinverted form of
      PYC35L-TAT peptide wherein all amino acids other than glycine are
      D-amino acids)

<400> SEQUENCE: 39

Arg Glu Arg Lys Ser Ser Ser Glu Ile Gly Gly Ser Arg Ile Ser Gln
1               5                   10                  15

Tyr Ala Gly Arg Arg Gln Arg Arg Lys Lys Arg Gly
                20                  25

<210> SEQ ID NO 40
<211> LENGTH: 31
<212> TYPE: PRT
<213> ORGANISM: artificial
<220> FEATURE:
<223> OTHER INFORMATION: PYC35L-FM peptide (peptide PYC35L with a
      C-terminal Kaposi FGF protein transduction domain)

<400> SEQUENCE: 40

Ala Tyr Gln Ser Ile Arg Ser Gly Gly Ile Glu Ser Ser Ser Lys Arg
1               5                   10                  15

Glu Arg Gly Ala Ala Val Leu Leu Pro Val Leu Leu Ala Ala Pro
                20                  25                  30

<210> SEQ ID NO 41
<211> LENGTH: 31
<212> TYPE: PRT
<213> ORGANISM: artificial
<220> FEATURE:
<223> OTHER INFORMATION: PYC35D-FM peptide (the retroinverted form of
      PYC35L-FM wherein all amino acids other than glycine are D-amino
      acids)

<400> SEQUENCE: 41

Pro Ala Ala Leu Leu Val Pro Leu Leu Val Ala Ala Gly Arg Glu Arg
1               5                   10                  15

Lys Ser Ser Ser Glu Ile Gly Gly Ser Arg Ile Ser Gln Tyr Ala
                20                  25                  30

<210> SEQ ID NO 42
<211> LENGTH: 29
```

```
<212> TYPE: PRT
<213> ORGANISM: artificial
<220> FEATURE:
<223> OTHER INFORMATION: PYC35D Scram-TAT peptide (retroinverted peptide
      comprising scrambled PYC35D peptide and retroinverted TAT basic
      region protein trasnduction domain, wherein all amino acids other
      than glycine are D-amino acids)

<400> SEQUENCE: 42

Lys Ile Glu Arg Ser Glu Gly Ile Ser Gln Ser Ala Arg Ser Arg Gly
1               5                   10                  15

Tyr Ser Gly Arg Arg Arg Gln Arg Arg Lys Lys Arg Gly
            20                  25

<210> SEQ ID NO 43
<211> LENGTH: 78
<212> TYPE: DNA
<213> ORGANISM: artificial
<220> FEATURE:
<223> OTHER INFORMATION: DNA encoding FLAG-PYC36 peptide

<400> SEQUENCE: 43
aggtcagact acaaggacga cgacgacaag ggactacaag gacgacgacg acaaggttat       60
caatcaatca agccatga                                                    78

<210> SEQ ID NO 44
<211> LENGTH: 25
<212> TYPE: PRT
<213> ORGANISM: artificial
<220> FEATURE:
<223> OTHER INFORMATION: FLAG-PYC36 peptide

<400> SEQUENCE: 44

Arg Ser Asp Tyr Lys Asp Asp Asp Asp Lys Gly Leu Gln Gly Arg Arg
1               5                   10                  15

Arg Gln Gly Tyr Gln Ser Ile Lys Pro
            20                  25

<210> SEQ ID NO 45
<211> LENGTH: 15
<212> TYPE: PRT
<213> ORGANISM: artificial
<220> FEATURE:
<223> OTHER INFORMATION: PYC36L peptide

<400> SEQUENCE: 45

Gly Leu Gln Gly Arg Arg Arg Gln Gly Tyr Gln Ser Ile Lys Pro
1               5                   10                  15

<210> SEQ ID NO 46
<211> LENGTH: 15
<212> TYPE: PRT
<213> ORGANISM: artificial
<220> FEATURE:
<223> OTHER INFORMATION: PYC36D peptide (the retroinverted form of
      PYC36L, peptide wherein all amino acids other than glycine are D-
      amino acids)

<400> SEQUENCE: 46

Pro Lys Ile Ser Gln Tyr Gly Gln Arg Arg Arg Gly Gln Leu Gly
1               5                   10                  15

<210> SEQ ID NO 47
<211> LENGTH: 26
<212> TYPE: PRT
<213> ORGANISM: artificial
<220> FEATURE:
```

-continued

```
<223> OTHER INFORMATION: PYC36L-TAT peptide (peptide PYC36L with an N-
      terminal TAT basic region protein transduction domain peptide)

<400> SEQUENCE: 47

Gly Arg Lys Lys Arg Gln Arg Arg Gly Gly Leu Gln Gly Arg
1               5                   10                  15

Arg Arg Gln Gly Tyr Gln Ser Ile Lys Pro
            20                  25

<210> SEQ ID NO 48
<211> LENGTH: 26
<212> TYPE: PRT
<213> ORGANISM: artificial
<220> FEATURE:
<223> OTHER INFORMATION: PYC36D-TAT peptide (the retroinverted form of
      PYC36L-TAT peptide wherein all amino acids other than glycine are
      D-amino acids)

<400> SEQUENCE: 48

Pro Lys Ile Ser Gln Tyr Gly Gln Arg Arg Gly Gln Leu Gly Gly
1               5                   10                  15

Arg Arg Gln Arg Arg Lys Lys Arg Gly
            20                  25

<210> SEQ ID NO 49
<211> LENGTH: 28
<212> TYPE: PRT
<213> ORGANISM: artificial
<220> FEATURE:
<223> OTHER INFORMATION: PYC36L-FM peptide (peptide PYC36L with a C-
      terminal Kaposi FGF protein transduction domain)

<400> SEQUENCE: 49

Gly Leu Gln Gly Arg Arg Arg Gln Gly Tyr Gln Ser Ile Lys Pro Gly
1               5                   10                  15

Ala Ala Val Leu Leu Pro Val Leu Leu Ala Ala Pro
            20                  25

<210> SEQ ID NO 50
<211> LENGTH: 28
<212> TYPE: PRT
<213> ORGANISM: artificial
<220> FEATURE:
<223> OTHER INFORMATION: PYC36D-FM peptide (the retroinverted form of
      PYC36L-FM wherein all amino acids other than glycine are D-amino
      acids)

<400> SEQUENCE: 50

Pro Ala Ala Leu Leu Val Pro Leu Leu Val Ala Ala Gly Pro Lys Ile
1               5                   10                  15

Ser Gln Tyr Gly Gln Arg Arg Gly Gln Leu Gly
            20                  25

<210> SEQ ID NO 51
<211> LENGTH: 26
<212> TYPE: PRT
<213> ORGANISM: artificial
<220> FEATURE:
<223> OTHER INFORMATION: PYC36D Scram-TAT peptide (retroinverted peptide
      comprising scrambled PYC36D peptide and retroinverted basic region
      TAT protein transduction domain, wherein all amino acids other
      than glycine are D-amino acids)

<400> SEQUENCE: 51

Lys Arg Arg Gly Gly Ile Leu Arg Tyr Gly Gln Pro Gln Ser Gln Gly
1               5                   10                  15
```

Arg Arg Arg Gln Arg Arg Lys Lys Arg Gly
            20                  25

<210> SEQ ID NO 52
<211> LENGTH: 108
<212> TYPE: DNA
<213> ORGANISM: artificial
<220> FEATURE:
<223> OTHER INFORMATION: DNA encoding FLAG-PYC38/39 peptide

<400> SEQUENCE: 52
aggtcagact acaaggacga cgacgacaag ggactacaag gccgccgaca gcctggccaa      60
cagcctcaag gccgctggag tggacgcgcg cttccagcgc atcgatag                  108

<210> SEQ ID NO 53
<211> LENGTH: 35
<212> TYPE: PRT
<213> ORGANISM: artificial
<220> FEATURE:
<223> OTHER INFORMATION: FLAG-PYC38/39 peptide

<400> SEQUENCE: 53

Arg Ser Asp Tyr Lys Asp Asp Asp Lys Gly Leu Gln Gly Arg Arg
1               5                   10                  15

Gln Pro Gly Gln Gln Pro Gln Gly Arg Trp Ser Gly Arg Ala Leu Pro
            20                  25                  30

Ala His Arg
        35

<210> SEQ ID NO 54
<211> LENGTH: 25
<212> TYPE: PRT
<213> ORGANISM: artificial
<220> FEATURE:
<223> OTHER INFORMATION: PYC38/39L peptide

<400> SEQUENCE: 54

Gly Leu Gln Gly Arg Arg Gln Pro Gly Gln Gln Pro Gln Gly Arg Trp
1               5                   10                  15

Ser Gly Arg Ala Leu Pro Ala His Arg
            20                  25

<210> SEQ ID NO 55
<211> LENGTH: 25
<212> TYPE: PRT
<213> ORGANISM: artificial
<220> FEATURE:
<223> OTHER INFORMATION: PYC38/39D peptide (the retroinverted form of
      PYC38/38L, peptide wherein all amino acids other than glycine are
      D-amino acids)

<400> SEQUENCE: 55

Arg His Ala Pro Leu Ala Arg Gly Ser Trp Arg Gly Gln Pro Gln Gln
1               5                   10                  15

Gly Pro Gln Arg Arg Gly Gln Leu Gly
            20                  25

<210> SEQ ID NO 56
<211> LENGTH: 36
<212> TYPE: PRT
<213> ORGANISM: artificial
<220> FEATURE:
<223> OTHER INFORMATION: PYC38/39L-TAT peptide (peptide PYC38/39L with
      an N-terminal TAT basic region protein transduction domain
      peptide)

```
<400> SEQUENCE: 56

Gly Arg Lys Lys Arg Arg Gln Arg Arg Gly Gly Leu Gln Gly Arg
1               5                   10                  15

Arg Gln Pro Gly Gln Gln Pro Gln Gly Arg Trp Ser Gly Arg Ala Leu
            20                  25                  30

Pro Ala His Arg
        35

<210> SEQ ID NO 57
<211> LENGTH: 36
<212> TYPE: PRT
<213> ORGANISM: artificial
<220> FEATURE:
<223> OTHER INFORMATION: PYC38/39D-TAT peptide (the retroinverted form
      of PYC38/39L-TAT peptide wherein all amino acids other than
      glycine are D-amino acids)

<400> SEQUENCE: 57

Arg His Ala Pro Leu Ala Arg Gly Ser Trp Arg Gly Gln Pro Gln Gln
1               5                   10                  15

Gly Pro Gln Arg Arg Gly Gln Leu Gly Gly Arg Arg Arg Gln Arg Arg
            20                  25                  30

Lys Lys Arg Gly
        35

<210> SEQ ID NO 58
<211> LENGTH: 38
<212> TYPE: PRT
<213> ORGANISM: artificial
<220> FEATURE:
<223> OTHER INFORMATION: PYC38/39L-FM peptide (peptide PYC38/39L with a
      C-terminal Kaposi FGF protein transduction domain)

<400> SEQUENCE: 58

Gly Leu Gln Gly Arg Arg Gln Pro Gly Gln Gln Pro Gln Gly Arg Trp
1               5                   10                  15

Ser Gly Arg Ala Leu Pro Ala His Arg Gly Ala Ala Val Leu Leu Pro
20                  25                  30

Val Leu Leu Ala Ala Pro
35

<210> SEQ ID NO 59
<211> LENGTH: 38
<212> TYPE: PRT
<213> ORGANISM: artificial
<220> FEATURE:
<223> OTHER INFORMATION: PYC38/39D-FM peptide (the retroinverted form of
      PYC38/39L-FM wherein all amino acids other than glycine are
      D-amino acids)

<400> SEQUENCE: 59

Pro Ala Ala Leu Leu Val Pro Leu Leu Val Ala Ala Gly Arg His Ala
1               5                   10                  15

Pro Leu Ala Arg Gly Ser Trp Arg Gly Gln Pro Gln Gln Gly Pro Gln
            20                  25                  30

Arg Arg Gly Gln Leu Gly
        35

<210> SEQ ID NO 60
<211> LENGTH: 72
<212> TYPE: DNA
<213> ORGANISM: artificial
<220> FEATURE:
<223> OTHER INFORMATION: DNA encoding FLAG-PYC41 peptide
```

<400> SEQUENCE: 60
aggtcagact acaaggacga cgacgacaag gtatcaatca atcaggagca ccatcgactc    60
ttgccgctat ga    72

<210> SEQ ID NO 61
<211> LENGTH: 23
<212> TYPE: PRT
<213> ORGANISM: artificial
<220> FEATURE:
<223> OTHER INFORMATION: FLAG-PYC41 peptide

<400> SEQUENCE: 61

Arg Ser Asp Tyr Lys Asp Asp Asp Lys Val Ser Ile Asn Gln Glu
1               5                   10                  15

His His Arg Leu Leu Pro Leu
            20

<210> SEQ ID NO 62
<211> LENGTH: 13
<212> TYPE: PRT
<213> ORGANISM: artificial
<220> FEATURE:
<223> OTHER INFORMATION: PYC41L peptide

<400> SEQUENCE: 62

Val Ser Ile Asn Gln Glu His His Arg Leu Leu Pro Leu
1               5                   10

<210> SEQ ID NO 63
<211> LENGTH: 14
<212> TYPE: PRT
<213> ORGANISM: artificial
<220> FEATURE:
<223> OTHER INFORMATION: PYC41D peptide (the retroinverted form of
      PYC41L, peptide wherein all amino acids other than glycine are
      D-amino acids with a C-terminal glyine linker added)

<400> SEQUENCE: 63

Leu Pro Leu Leu Arg His His Glu Gln Asn Ile Ser Val Gly
1               5                   10

<210> SEQ ID NO 64
<211> LENGTH: 24
<212> TYPE: PRT
<213> ORGANISM: artificial
<220> FEATURE:
<223> OTHER INFORMATION: PYC41L-TAT peptide (peptide PYC41L with an
      N-terminal TAT basic region protein transduction domain peptide)

<400> SEQUENCE: 64

Gly Arg Lys Lys Arg Arg Gln Arg Arg Gly Val Ser Ile Asn Gln
1               5                   10                  15

Glu His His Arg Leu Leu Pro Leu
            20

<210> SEQ ID NO 65
<211> LENGTH: 24
<212> TYPE: PRT
<213> ORGANISM: artificial
<220> FEATURE:
<223> OTHER INFORMATION: PYC41D-TAT peptide (the retroinverted form of
      PYC41L-TAT peptide wherein all amino acids other than glycine are
      D-amino acids)

<400> SEQUENCE: 65

```
Leu Pro Leu Leu Arg His His Glu Gln Asn Ile Ser Val Gly Arg Arg
1               5                   10                  15

Arg Gln Arg Arg Lys Lys Arg Gly
            20

<210> SEQ ID NO 66
<211> LENGTH: 26
<212> TYPE: PRT
<213> ORGANISM: artificial
<220> FEATURE:
<223> OTHER INFORMATION: PYC41L-FM peptide (peptide PYC41L with a
      C-terminal Kaposi FGF protein transduction domain)

<400> SEQUENCE: 66

Val Ser Ile Asn Gln Glu His His Arg Leu Leu Pro Leu Gly Ala Ala
1               5                   10                  15

Val Leu Leu Pro Val Leu Leu Ala Ala Pro
            20                  25

<210> SEQ ID NO 67
<211> LENGTH: 26
<212> TYPE: PRT
<213> ORGANISM: artificial
<220> FEATURE:
<223> OTHER INFORMATION: PYC41D-FM peptide (the retroinverted form of
      PYC41L-FM wherein all amino acids other than glycine are D-amino
      acids)

<400> SEQUENCE: 67

Pro Ala Ala Leu Leu Val Pro Leu Leu Val Ala Ala Gly Leu Pro Leu
1               5                   10                  15

Leu Arg His His Glu Gln Asn Ile Ser Val
            20                  25

<210> SEQ ID NO 68
<211> LENGTH: 32
<212> TYPE: PRT
<213> ORGANISM: ARTIFICIAL
<220> FEATURE:
<223> OTHER INFORMATION: JNK1-1D-TAT peptide (retroinverted JNK1-1
      peptide and TAT basic region protein transduction domain, wherein
      all amino acids other than glycine are D-amino acids)

<400> SEQUENCE: 68

Thr Asp Gln Ser Arg Pro Val Gln Pro Phe Leu Asn Leu Thr Thr Pro
1               5                   10                  15

Arg Lys Pro Arg Pro Pro Arg Arg Gln Arg Arg Lys Lys Arg Gly
            20                  25                  30
```

NEUROPROTECTIVE PEPTIDE INHIBITORS OF AP-1 SIGNALING AND USES THEREFOR

RELATED APPLICATION DATA

The present invention claims priority from U.S. Patent Application No. 60/826,208 filed Sep. 19, 2006 which is herein incorporated by reference in its entirety.

REFERENCE TO SEQUENCE LISTING

This application includes a Sequence Listing submitted electronically as a text file named 15423US_sequencelisting.txt, created on Apr. 8, 2010, with a size of 24,576 bytes and submitted to the USPTO via EFS-Web on Apr. 12, 2010. The sequence listing is incorporated by reference.

FIELD OF THE INVENTION

The present invention relates generally to peptides having neuroprotective properties by virtue of inhibiting AP-1 signaling in mammalian cells. Also provided are methods for the diagnosis and treatment of aberrant neuronal function by virtue of inhibiting, delaying or preventing AP-1 signaling neuronal disorders stroke using the peptides of the invention.

BACKGROUND OF THE INVENTION

1. General Information

This specification contains nucleotide and amino acid sequence information prepared using PatentIn Version 3.3, presented herein after the claims. Each nucleotide sequence is identified in the sequence listing by the numeric indicator <210> followed by the sequence identifier (e.g. <210>1, <210>2, <210>3, etc). The length and type of sequence (DNA, protein (PRT), etc), and source organism for each nucleotide sequence, are indicated by information provided in the numeric indicator fields <211>, <212> and <213>, respectively. Nucleotide sequences referred to in the specification are defined by the term "SEQ ID NO:", followed by the sequence identifier (eg. SEQ ID NO: 1 refers to the sequence in the sequence listing designated as <400>1).

The designation of nucleotide residues referred to herein are those recommended by the IUPAC-IUB Biochemical Nomenclature Commission, wherein A represents Adenine, C represents Cytosine, G represents Guanine, T represents thymine, Y represents a pyrimidine residue, R represents a purine residue, M represents Adenine or Cytosine, K represents Guanine or Thymine, S represents Guanine or Cytosine, W represents Adenine or Thymine, H represents a nucleotide other than Guanine, B represents a nucleotide other than Adenine, V represents a nucleotide other than Thymine, D represents a nucleotide other than Cytosine and N represents any nucleotide residue.

As used herein the term "derived from" shall be taken to indicate that a specified integer may be obtained from a particular source albeit not necessarily directly from that source.

Throughout this specification, unless the context requires otherwise, the word "comprise", or variations such as "comprises" or "comprising", will be understood to imply the inclusion of a stated step or element or integer or group of steps or elements or integers but not the exclusion of any other step or element or integer or group of elements or integers.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Each embodiment described herein is to be applied mutatis mutandis to each and every other embodiment unless specifically stated otherwise.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

The present invention is performed without undue experimentation using, unless otherwise indicated, conventional techniques of molecular biology, microbiology, virology, recombinant DNA technology, peptide synthesis in solution, solid phase peptide synthesis, and immunology. Such procedures are described, for example, in the following texts:

1. Sambrook, Fritsch & Maniatis, whole of Vols I, II, and III;
2. DNA Cloning: A Practical Approach, Vols. I and II (D. N. Glover, ed., 1985), IRL Press, Oxford, whole of text;
3. Oligonucleotide Synthesis: A Practical Approach (M. J. Gait, ed., 1984) IRL Press, Oxford, whole of text, and particularly the papers therein by Gait, pp 1-22; Atkinson et al., pp 35-81; Sproat et al., pp 83-115; and Wu et al., pp 135-151;
4. Nucleic Acid Hybridization: A Practical Approach (B. D. Hames & S. J. Higgins, eds., 1985) IRL Press, Oxford, whole of text;
5. Animal Cell Culture: Practical Approach, Third Edition (John R. W. Masters, ed., 2000), ISBN 0199637970, whole of text;
6. Immobilized Cells and Enzymes: A Practical Approach (1986) IRL Press, Oxford, whole of text;
7. Perbal, B., A Practical Guide to Molecular Cloning (1984);
8. Methods In Enzymology (S. Colowick and N. Kaplan, eds., Academic Press, Inc.), whole of series;
9. J. F. Ramalho Ortigão, "The Chemistry of Peptide Synthesis" In: Knowledge database of Access to Virtual Laboratory website (Interactiva, Germany);
10. Sakakibara, D., Teichman, J., Lien, E. Land Fenichel, R. L. (1976). *Biochem. Biophys. Res. Commun.* 73 336-342
11. Merrifield, R. B. (1963). *J. Am. Chem. Soc.* 85, 2149-2154.
12. Barany, G. and Merrifield, R. B. (1979) in *The Peptides* (Gross, E. and Meienhofer, J. eds.), vol. 2, pp. 1-284, Academic Press, New York.
13. Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart.
14. Bodanszky, M. (1984) *Principles of Peptide Synthesis*, Springer-Verlag, Heidelberg.
15. Bodanszky, M. & Bodanszky, A. (1984) *The Practice of Peptide Synthesis*, Springer-Verlag, Heidelberg.
16. Bodanszky, M. (1985) *Int. J. Peptide Protein Res.* 25, 449-474.
17. Handbook of Experimental Immunology, Vols. I-IV (D. M. Weir and C. C. Blackwell, eds., 1986, Blackwell Scientific Publications).

18. McPherson et al., *In: PCR A Practical Approach.*, IRL Press, Oxford University Press, Oxford, United Kingdom, 1991.
19. Methods in Yeast Genetics: A Cold Spring Harbor Laboratory Course Manual (D. Burke et al., eds) Cold Spring Harbor Press, New York, 2000 (see whole of text).
20. Guide to Yeast Genetics and Molecular Biology. In: Methods in Enzymology Series, Vol. 194 (C. Guthrie and G. R. Fink eds) Academic Press, London, 1991 2000 (see whole of text).

2. Description of the Related Art

Peptide Therapeutics

As a response to the increasing demand for new lead compounds and new target identification and validation reagents, the pharmaceutical industry has increased its screening of various sources for new lead compounds having a unique activity or specificity in therapeutic applications, such as, for example, in the treatment of neoplastic disorders, infection, modulating immunity, autoimmunity, fertility, etc.

It is known that proteins bind to other proteins, antigens, antibodies, nucleic acids, and carbohydrates. Such binding enables the protein to effect changes in a wide variety of biological processes in all living organisms. As a consequence, proteins represent an important source of natural modulators of phenotype. Accordingly, peptides that modulate the binding activity of a protein represent attractive lead compounds (drug candidates) in primary or secondary drug screening. For example, the formation of a target biological interaction that has a deleterious effect (eg. replication of a pathogen or of a cancer cell), can be assayed to identify lead compounds that antagonize the biological interaction.

Antibodies represent the fastest growing class of approved drugs in this area, however they require complex and expensive synthesis and are difficult to deliver via non-injectable routes. In contrast, large peptides can often be made synthetically and are increasingly being delivered by buccal, intranasal or intranasal routes as alternatives to injection. Furthermore, intracellular delivery of peptides is also now possible in vivo using protein transduction domains. These advances make peptide-based therapeutics an attractive alternative to antibody-based therapeutics.

Existing drawbacks associated with peptide-based therapeutics include their low affinity, high turnover in vivo and difficulties in their isolation compared to small molecules. For example, peptides that target protein interaction interfaces which may be large and relatively featureless are generally more difficult to produce and isolate when compared to small molecule inhibitors of enzyme-active sites that generally form small complex pockets. Accordingly, it is not facile to identify peptides that address these problems.

For example, random peptide (synthetic mimetic or mimotope) libraries can be produced using short random oligonucleotides produced by synthetic combinatorial chemistry, cloned into an appropriate vehicle for expression, and the encoded peptide screened using one of a variety of approaches. However, the ability to isolate active peptides from random fragment libraries can be highly variable with low affinity interactions occurring between many of the peptide-binding partners and very low hit-rates for biologically active peptides. Moreover, the expressed peptides often show little or none of the secondary or tertiary structure required for efficient binding activity, and/or are unstable. This is not surprising, considering that biological molecules appear to recognize shape and charge rather than primary sequence (Yang and Honig *J. Mol. Biol.* 301(3), 691-711 2000) and that such random peptides are generally too small to comprise a protein domain or to form the secondary structure of a protein domain. Moreover even the largest peptide libraries to have been produced do not contain sufficient complexities to exhaustively cover all of the possible combinations of the 20 amino acids, for peptides of more than approximately a dozen residues. The relatively unstructured 'linear' nature of many artificial peptides derived from random amino acid sequences also leads to their more rapid degradation and clearance following administration to a subject in vivo, thereby reducing their appeal as therapeutic agents.

In contrast, natural protein folds or subdomains are understood in the art to mean independently folding peptide structures (e.g., a 19-residue fragment from the C-loop of the fourth epidermal growth factor-like domain of thrombomodulin as been described by Alder et al, *J. Biol. Chem.*, 270: 23366-23372, 1995). These constrained structures provide thermodynamic advantages to bind other protein surfaces through limiting the entropic cost of binding. Moreover, structured folds can be less susceptible to proteolysis than unstructured linear peptides, increasing their biological stability.

To enhance the probability of obtaining useful bioactive peptides or proteins from random peptide libraries, peptides have previously been constrained within scaffold structures, eg., thioredoxin (Trx) loop (Blum et al. *Proc. Natl. Acad. Sci. USA*, 97, 2241-2246, 2000) or catalytically inactive staphylococcal nuclease (Norman et al, *Science*, 285, 591-595, 1999), to enhance their stability. Constraint of peptides within such structures has been shown, in some cases, to enhance the affinity of the interaction between the expressed peptides and its target, presumably by limiting the degrees of conformational freedom of the peptide, and thereby minimizing the entropic cost of binding.

Recently, peptide mimotopes of less than about 50 amino acids in length have been described that are capable of forming protein domains by virtue of assuming conformations sufficient for binding to a target protein or target nucleic acid ("Phylomer™ peptides", Phylogica, Perth, western Australia, Australia) e.g., International Patent Application No. PCT/AU00/00414 and US Patent Publication No. 2003-0215846 A1. Such Phylomer™ peptides show promise in overcoming the existing drawbacks associated with peptide therapeutics. The conformation(s) of such Phylomer™ peptides is a product of secondary and/or tertiary structural features and, by virtue of the peptide binding to its target protein or protein interaction interface is compatible with, albeit not necessarily iterative of, the target protein(s) or target protein interaction interface. Such secondary structural features may suggest that Phylomer™ peptides, on average, have higher substrate affinities and longer half-lives than more conventional random peptides. On the other hand, Phylomer™ peptides may also provide production and delivery advantages compared to antibody-based therapies by virtue of their small size. Additionally, because Phylomer™ peptides are derived from libraries comprising mixtures of small genome fragments from evolutionarily-diverse bacteria and eukaryotes having small albeit well-characterized genomes, they can be screened in silico to select against those peptides sequences that are likely, because of their known strucure or function, to produce adverse reactions in recipient mammals, including humans. Notwithstanding the need for empirical testing of therapeutic products, this "safety" feature of Phylomer™ peptides provides a significant potential advantage over peptides derived from mammals, including antibodies.

Neuronal Disorders Involving Neuronal Cell Death

Neuronal disorders such as migraine, stroke, traumatic brain injury, epilepsy and neurodegenerative disorders including Huntington's Disease (HD), Parkinson's Disease (PD), Alzheimer's Disease (AD) and Amyotrophic Lateral Sclerosis (ALS) are major causes of morbidity and disability arising from long term brain injury. These effects generally involve apoptosis and/or necrosis of neurons, possibly involving diverse pathways including oxidative stress.

As used herein, the term "stroke" includes any ischemic disorder e.g., a peripheral vascular disorder, a venous thrombosis, a pulmonary embolus, a myocardial infarction, a transient ischemic attack, lung ischemia, unstable angina, a reversible ischemic neurological deficit, adjunct thromolytic activity, excessive clotting conditions, reperfusion injury, sickle cell anemia, a stroke disorder or an iatrogenically induced ischemic period such as angioplasty, or cerebral ischemia.

Glutamate Excitotoxicity

Increased extracellular levels of the neurotransmitter glutamate cause neuronal cell death via excitotoxicity. An accumulation of extracellular glutamate over-stimulates NMDA and AMPA receptors resulting in an influx of extracellular calcium and sodium ions and the release of bound calcium from intracellular stores. The increase in intracellular calcium initiates a range of cell damaging events involving phospholipases, proteases, phosphatases, kinases and nitric oxide synthase, as well as the activation of the pro-apoptotic transcription factor c-Jun.

Involvement of the AP-1 Signaling Pathway in Neuronal Function

Various types of evidence indicate that c-Jun N-Terminal Kinase (JNK or SAPK) is involved in neuronal cell death during or following ischemia, via activation of c-Jun (a component of the AP-1 complex) in an analogous way to the known activation of this stress kinase response in other forms of ischemia such as coronary heart disease or in organ or blood vessel reperfusion injury.

Components of the AP-1 pathway associate with scaffold proteins that modulate their activities and cellular localization. JNK activity is controlled by a cascade of protein kinases and by protein phosphatases, including dual-specificity MAPK phosphatases. For example, the JNK-interacting protein-1 (JIP-1) scaffold protein specifically binds JNK, MAPK kinase 4 (MKK4) and MAPK kinase 7 (MKK7), and members of the mixed lineage kinase (MLK) family, and regulates INK activation in neurons. Distinct regions within the N termini of MKK7 and the MLK family member dual leucine zipper kinase (DLK) mediate their binding to JIP-1. JNK binds to c-Jun, and this appears to be required for efficient c-Jun phosphorylation.

Several members of the death-related AP-1 pathway acting upstream of JNK have been defined. The most distal of these are the Rho small GTPase family members Rac1 and Cdc42. Over expression of constitutively active forms of Rac1 (i.e., Rac1V12) and Cdc42 (i.e., Cdc42V12) leads to activation of the AP-1 pathway and to death of Jurkat T lymphocytes, PC12 cells, and sympathetic neurons. Conversely, over expression of dominant-negative mutants of Cdc42 (i.e., Cdc42N17) and Rac1 (i.e., Rac1N17) in sympathetic neurons prevents elevation of c-Jun and death evoked by nerve growth factor (NGF) withdrawal (Bazenet et al., *Proc. Natl. Acad. Sci. USA* 95, 3984-3989, 1998; Chuang et al., *Mol. Biol. Cell* 8, 1687-1698, 1997). Over expression of the dominant negative mutant Rac1N17 also reverses the induction of death by Cdc42V12, whereas Cdc42N17 has no effect on Rac-1V12-induced death, suggesting that Cdc42 lies upstream of Rac1 (Bazenet et al., *Proc. Natl. Acad. Sci. USA* 95, 3984-3989, 1998). Similar approaches have indicated that mitogen-activated protein kinase kinases 4 and 7 (MKK4 and MKK7) lie downstream of Cdc42 and Rac1 and directly upstream of the JNKs (Foltz et al., *J. Biol. Chem.* 273, 9344-9351, 1998; Holland et al., *J. Biol. Chem.* 272, 24994-24998, 1997; Mazars et al., *Oncogene* 19, 1277-1287, 2000; Vacratsis et al., *J. Biol. Chem.* 275, 27893-27900, 2000; Xia et al., *Science* 270, 1326-1331, 1995; Yamauchi et al., *J. Biol. Chem.* 274, 1957-1965, 1999). Studies using constitutively active and dominant-negative constructs have also implicated apoptosis signal-regulating kinase 1 (ASK1) as an additional participant in the pathway that lies between Cdc42 and the downstream MKKs and JNKs (Kanamoto et al., *Mol. Cell. Biol.* 20, 196-204, 2000).

MLKs have been shown to function as MKK kinases and lead to activation of JNKs via activation of MKKs (Bock et al., *J. Biol. Chem.* 275, 14231-1424, 2000; Cuenda et al., *Biochem. J.* 333, 11-159, 1998; Hirai et al., *J. Biol. Chem.* 272, 15167-15173, 1997; Merritt et al., *J. Biol. Chem.* 274, 10195-10202, 1999; Rana et al., *J. Biol. Chem.* 271, 19025-19028, 1996; Tibbles et al., *EMBO J.* 15, 7026-7035, 1996; Vacratsis et al., *J. Biol. Chem.* 275, 27893-27900, 2000). Members of the family include MLK1, MLK2 (also called MST), MLK3 (also called SPRK or PTK1), dual leucine zipper kinase (DLK; also called MUK or ZPK), and leucine zipper-bearing kinase (LZK). Constitutively active mutants of Rac1 and Cdc42 have been found to bind to and to modulate the activities of MLK2 and -3, and co-expression of MLK3 and activated Cdc42 leads to enhanced MLK3 activation.

In animal models of ischemia or migraine, stroke, apoptotic neurons have enhanced phosphorylation of the transcription factor c-Jun by JNK. Additionally, neuronal c-Jun levels are elevated in response to trophic factor withdrawal, and dominant-negative forms of this transcription factor are at least partially-protective against neuronal cell death evoked by selective activation of JNKs (Filers et al., *J. Neurosci.* 18, 1713-1724, 1998; Ham et al., *Neuron* 14, 927-939).

The transcriptional activating activity of c-Jun is regulated at the post-translational level by its phosphorylation by JNK (SAPK) at two residues within the amino-terminal transactivation domain, serines 63 and 73, in response to a variety of cellular stresses. Phosphorylation of these two residues is critical for the transcriptional activating activity of c-Jun, since mutation of them markedly decreases this activity. JNKs (SAPKs) readily phosphorylate c-Jun at Ser 63/73, and at a rate that is about 10 times faster than ERK-1 and ERK-2. The JNKs (SAPKs) account for the majority of c-Jun transactivation domain (Ser 63/73) kinase activity after reperfusion, suggesting that they trigger part of the kidney's very early genetic response to ischemia by enhancing the transcriptional activating activity of c-Jun. Since induction of c-Jun is auto-regulated, it is likely that activation of the JNKs (SAPKs) is, at least in part, responsible for the induction of c-Jun following myocardial or renal ischemia.

The role of JNKs (SAPKs) in the control of gene expression during and/or following ischemia extends well beyond the regulation of c-Jun by INK. It is known that AP-1 comprises complexes of c-Jun with parters such as c-Fos or ATF-2 (a member of the CREB family). When complexed with c-Fos, the dimer is targeted to promoters, such as that of the collagenase gene, containing canonical AP-1 elements. When complexed with ATF-2, however, the dimer appears to prefer CRE sequences, and AP-1 variants such as that contained in the c-Jun promoter which controls induction of c-Jun in response to a variety of stimuli. After ischemia and reperfusion, ATF-2 and c-Jun are targeted as a heterodimer to both ATF/CRE motifs and the Jun2 TRE within the c-Jun promoter. This suggests that, following reperfusion of ischemic tissue, the JNKs (SAPKs) target ATF-2/c-Jun heterodimers to various promoters, including the c-Jun promoter, and enhance transcriptional activating activity of both components of the c-Jun/ATF-2 dimer. This may provide a potent mechanism for the induction of a large number of genes regulated by promoters containing ATF/CRE sites or AP-1 variants to which the heterodimer binds.

Dimerization of c-Jun also leads to apoptosis in neurons in response to ischemia (Tong et al., *J. Neurochem* 71, 447-459, 1998; Ham et al., *Biochem. Pharmacol.* 60, 1015-1021, 2000).

A homodimer of c-Jun is also known to activate the c-Jun transcription factor via binding to the transcriptional regulatory element (TRE) in the c-Jun promoter.

As used herein unless specifically stated otherwise or the context requires otherwise, the term "c-Jun dimerization" shall be taken to include homo-dimerization of c-Jun monomers and the partnering of c-Jun with another peptide or polypeptide e.g., JNK, c-Fos, ATF-2. Similarly, unless specifically stated otherwise or the context requires otherwise, the term "c-Jun dimer" shall be taken to include homo-dimer of c-Jun monomers and a heterodimer of c-Jun with another peptide or polypeptide e.g., c-Fos, ATF-2, including transient complexes such as those between the JNK kinase and its substrate c-Jun.

Treatment of Neuronal Cell Death

Currently, there is no effective clinical agent that inhibits the delayed neuronal cell death associated with such neuronal dysfunction. For example, drugs such as Activase (genetically engineered tissue plasminogen activator; Genentech), Abciximab (a platelet inhibitor; Centocor), and Ancrod (fibrinogenolytic) have had limited success, even if administered soon after the stroke occurs. These agents offer no clinical benefit if administered later than the period immediately following the stroke and unfortunately many patients present to a hospital after this window of opportunity. Even alternative approaches that target glutamate receptors to prevent glutamate excitotoxicity causing neuronal damage have shown no significant or consistent improvements in patient outcome, most likely due to the need to target these events early.

SUMMARY OF THE INVENTION

The present invention is based upon the identification by the inventors of Phylomer™ peptides that inhibit AP-1 signaling as determined by binding to human c-Jun in yeast cells, and AP-1 regulated transcription in mammalian cells. The peptides were identified using a reverse hybrid screening technology that employed dual counter selection using the cytotoxic compounds cycloheximide and 5-fluoro orotic acid (5-FOA), in which only cells in which an interaction between JUN1 and JUNZ is disrupted could be rescued (Example 1). Phylomer™ peptides that rescued yeast cells in primary reverse hybrid screens were then expressed in mammalian cells expressing luciferase under operable control of AP-1 enhancer elements, to confirm their ability to inhibit AP-1 regulated transcription (Example 2).

By virtue of their activity in yeast cells in preventing JUN1/JUNZ dimerization, the identified Phylomer™ peptides are candidate AP-1 signaling inhibitory peptides that inhibit AP-1 signaling by direct inhibition of c-Jun homodimerization and/or heterodimerization. Such a mechanism of action is entirely consistent with the ability of the Phylomer™ peptides to also prevent expression of a luciferase reporter gene in mammalian cells.

The AP-1 binding Phylomer™ peptides can also be validated by other related methodologies, such as forward two hybrid screens using c-Jun as a bait. Peptide inhibitors of c-Jun/dependent autoactivation in two hybrid assays can be captured using counterselection approaches such as those described above. Similarly inhibitors of c-Jun to AP1 binding sites can be validated through standard one hybrid assays using this promoter element. A subset of such c-Jun binding, or DNA binding peptides might be expected to also inhibit AP1 signalling.

It is also possible that certain Phylomer™ peptides inhibit AP-1 signaling by indirect means e.g., involving factors upstream of c-Jun that are conserved between yeasts and mammals. For example, yeast cells possess a stress-responsive MAPK (SAPK) cascade; a multistep phosphorelay system; and AP-1-like transcription factor (Yap 1) that govern the response of yeasts to oxidative stress (Ikner et al., *Mutation Res.* 569, 13-27, 2005), and which may be involved in regulating the apoptotic response to cytotoxic compounds used in the reverse hybrid screens. The yeast MAPK (SAPK) cascade involves signaling from a complex comprising yeast homologs of human Cdc42 and Pak1 (i.e., Cdc42 and Step 20, respectively) to the MAPKKK Ste11, which regulates the MAPKK Pbs2 and, in turn, the MAPK Hog1 to regulate gene expression, membrane transport, cell cycle progression, etc. The yeast phosphorelay system appears to converge on Pbs2 MAPKK of the Hog1 SAPK cascade and is initiated by the transmembrane protein Sho1 which activates Pbs2 through the MAPKKK Ste11 of the Hog1 SAPK cascade. The AP-1-like transcription factor (Yap1) appears to serve as an oxidative stress sensor that directly regulates transcription albeit independently of the SAPK pathway. Without being bound by any theory or mode of action, the present inventors reason that a Phylomer™ peptide identified in a counter selection screen such as a reverse hybrid screening of yeast cells may rescue yeast cells from an event upstream of Hog1 in yeast that would otherwise lead to activation of these stress responses (including cell-cycle modulation) leading to cell death. If the same Phylomer™ peptide also recognizes a homologous mammalian AP-1 pathway component upstream of c-Jun and/or JNK, inhibition of that component would also explain the observed reduction in AP-1 mediated activation of luciferase reporter gene expression observed in mammalian cells.

Accordingly, the identified Phylomer™ peptides from yeast reverse hybrid screens not to be limited by their ability to inhibit c-Jun dimerization, and are designated herein as "AP-1 inhibitors" or "AP-1 complex formation inhibitors" or "AP-1 signaling inhibitors" or similar term. It is to be understood that such terminology includes the direct c-Jun dimerization and/or upstream indirect effects e.g., acting on phosphorylation of Cdc42, Pak1 or Rac1, or dimerization of Cdc42, Pak1 or Rac1 in mammalian cells. Preferred AP-1 signaling inhibitory peptides will inhibit later steps in the AP-1 signaling pathway e.g., c-Jun dimerization, to thereby provide greater specificity than, for example, a JNK inhibitory peptide.

It is also to be understood that the term "c-Jun dimerization" includes c-Jun self-dimerization or homodimerization, and heterodimerization between c-Jun and another protein e.g., ATF-2, c-Fos or JNK and preferably between c-Jun and ATF-2 or between c-Jun and c-Fos (i.e., a c-Jun heterodimer) or an analog of said isolated peptide or protein domain.

The present inventors have shown herein that five AP-1 signaling inhibitory peptides, designated PYC19, PYC35, PYC36, PYC38/39 and PYC41, are also neuroprotective in in vitro and in vivo models of neurological damage in humans. The sequences of these peptides are set forth in Table 1 herein and the accompanying Sequence Listing. In particular, the Phylomer™ peptides are neuroprotective following glutamate and/or NMDA excitotoxicity in primary cortical neuronal cultures, establishing their relevance to therapy of disorders such as migraine, stroke, traumatic brain injury, epilepsy and neurodegenerative disorders including Parkinson's Disease (PD), Alzheimer's Disease (AD) and Amyotrophic Lateral Sclerosis (ALS). The inventors have also demonstrated that AP-1 signaling inhibitory Phylomer™ peptides, in particular PYC35 and/or PYC36, protect cultured cortical neurons in an in vitro model of cerebral ischemia i.e., Oxygen Glucose Deprivation (OGD). The data presented herein also demonstrate that AP-1 signaling inhibitory Phylomer™ peptides, in particular PYC35 and/or PYC36, are neuroprotective in vivo, in a head injury model of global cerebral ischemia, as determined by MAP2 immunoreactivity (a marker of neuron loss in brain tissue) following administration of peptides. In particular, peptide PYC35 provides significant neuroprotection following acute cortical injury of rat brain tissue in situ, including: (i) reduced loss of neurons as determined by MAP2 immunoreactivity; (ii) reduced astrogliosis as determined by glial fibrillary acidic protein immunoreactivity; and (iii) reduced microglial activation as determined by ferritin immunoreactivity. These data are consistent with a neuroprotective function and therapeutic potential in the treatments of head injury and/or ischemia.

Accordingly, the present invention provides a neuroprotective AP-1 signaling inhibitory peptide individually or collectively selected from the group consisting of:

(i) a neuroprotective AP-1 signaling inhibitory peptide comprising a sequence individually or collectively selected from the group consisting of: SEQ ID NO: 28, SEQ ID NO: 29, SEQ ID NO: 30, SEQ ID NO: 31, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 54, SEQ ID NO: 55, SEQ ID NO: 56, SEQ ID NO: 57, SEQ ID NO: 62, SEQ ID NO: 63, SEQ ID NO: 64 and SEQ ID NO: 65;

(ii) a neuroprotective AP-1 signaling inhibitory peptide comprising a fusion between a protein transduction domain and a peptide comprising a sequence individually or collectively selected from the group consisting of SEQ ID NO: 28, SEQ ID NO: 29, SEQ ID NO: 36, SEQ ID NO: 37, SEQ ID NO: 45, SEQ ID NO: 46, SEQ ID NO: 54, SEQ ID NO: 55, SEQ ID NO: 62 and SEQ ID NO: 63;

(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions; and (iv) a retroinverted analog of (i) or (ii) or (iii) or (iv) comprising one or more D-amino acids.

By "individually" is meant that the invention encompasses the recited neuroprotective peptides or groups of neuroprotective peptides separately, and that, notwithstanding that individual peptides or groups of peptides may not be separately listed herein the accompanying claims may define such peptides or groups of peptides separately and divisibly from each other.

By "collectively" is meant that the invention encompasses any number or combination of the recited neuroprotective peptides or groups of neuroprotective peptides, and that, notwithstanding that such numbers or combinations of peptides or groups of peptides may not be specifically listed herein the accompanying claims may define such combinations or subcombinations separately and divisibly from any other combination of peptides or groups of peptides.

In another example, the neuroprotective AP-1 signaling inhibitory peptide is individually or collectively selected from the group consisting of:

(i) a neuroprotective AP-1 signaling inhibitory peptide comprising a sequence individually or collectively selected from the group consisting of: SEQ ID NO: 28, SEQ ID NO: 29, SEQ ID NO: 30, SEQ ID NO: 31, SEQ ID NO: 54, SEQ ID NO: 55, SEQ ID NO: 56, SEQ ID NO: 57, SEQ ID NO: 62, SEQ ID NO: 63, SEQ ID NO: 64 and SEQ ID NO: 65;

(ii) a neuroprotective AP-1 signaling inhibitory peptide comprising a fusion between a protein transduction domain and a peptide comprising a sequence individually or collectively selected from the group consisting of SEQ ID NO: 28, SEQ ID NO: 29, SEQ ID NO: 54, SEQ ID NO: 55, SEQ ID NO: 62 and SEQ ID NO: 63;

(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions; and (iv) a retroinverted analog of (i) or (ii) or (iii) or (iv) comprising one or more D-amino acids.

In another example, the neuroprotective AP-1 signaling inhibitory peptide is a retroinverted peptide selected from the group consisting of:

(i) a neuroprotective AP-1 signaling inhibitory peptide comprising a sequence selected from the group consisting of: SEQ ID NO: 29, SEQ ID NO: 31, SEQ ID NO: 37, SEQ ID NO: 39, SEQ ID NO: 46, SEQ ID NO: 48, SEQ ID NO: 55, SEQ ID NO: 57, SEQ ID NO: 63 and SEQ ID NO: 65;

(ii) a neuroprotective AP-1 signaling inhibitory peptide comprising a fusion between a protein transduction domain and a peptide comprising a sequence selected from the group consisting of SEQ ID NO: 29, SEQ ID NO: 37, SEQ ID NO: 46, SEQ ID NO: 55 and SEQ ID NO: 63; and (iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions.

In another example, the neuroprotective AP-1 signaling inhibitory peptide provides for greater inhibition of glutamate excitotoxicity than an equimolar concentration of the peptide JNK1-1D-TAT (SEQ ID NO: 68) which inhibits JNK, and preferably significantly inhibits glutamate excitotoxicity at a concentration of less than about 1 µM or 2 µM. In accordance with this example, a preferred neuroprotective AP-1 signaling inhibitory peptide is selected from the group consisting of:

(i) a neuroprotective AP-1 signaling inhibitory peptide comprising a sequence selected from the group consisting of: SEQ ID NO: 29, SEQ ID NO: 31, SEQ ID NO: 37, SEQ ID NO: 39, SEQ ID NO: 45, SEQ ID NO: 46, SEQ ID NO: 47, SEQ ID NO: 48, SEQ ID NO: 55 and SEQ ID NO: 57;

(ii) a neuroprotective AP-1 signaling inhibitory peptide comprising a fusion between a protein transduction domain and a peptide comprising a sequence selected from the group consisting of SEQ ID NO: 29, SEQ ID NO: 37, SEQ ID NO: 45, SEQ ID NO: 46 and SEQ ID NO: 55;

(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions; and (iv) a retroinverted analog of (i) or (ii) or (iii) or (iv) comprising one or more D-amino acids.

Preferably, the neuroprotective AP-1 signaling inhibitory peptide is a retroinverted peptide selected from the group consisting of:
(i) a neuroprotective AP-1 signaling inhibitory peptide comprising a sequence selected from the group consisting of: SEQ ID NO: 29, SEQ ID NO: 31, SEQ ID NO: 37, SEQ ID NO: 39, SEQ ID NO: 46, SEQ ID NO: 48, SEQ ID NO: 55 and SEQ ID NO: 57;
(ii) a neuroprotective AP-1 signaling inhibitory peptide comprising a fusion between a protein transduction domain and a peptide comprising a sequence selected from the group consisting of SEQ ID NO: 29, SEQ ID NO: 37, SEQ ID NO: 46 and SEQ ID NO: 55; and
(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions.

Alternatively, the neuroprotective AP-1 signaling inhibitory peptide is a retroinverted peptide selected from the group consisting of:
(i) a neuroprotective AP-1 signaling inhibitory peptide comprising a sequence selected from the group consisting of: SEQ ID NO: 29, SEQ ID NO: 31, SEQ ID NO: 55 and SEQ ID NO: 57;
(ii) a neuroprotective AP-1 signaling inhibitory peptide comprising a fusion between a protein transduction domain and a peptide comprising a sequence selected from the group consisting of SEQ ID NO: 29 and SEQ ID NO: 55; and
(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions.

In yet another example, the neuroprotective AP-1 signaling inhibitory peptide protects neurons from cell death in vivo. In accordance with this example, a preferred neuroprotective AP-1 signaling inhibitory peptide is selected from the group consisting of:
(i) a neuroprotective AP-1 signaling inhibitory peptide comprising a sequence selected from the group consisting of: SEQ ID NO: 36, SEQ ID NO: 37, SEQ ID NO: 38, SEQ ID NO: 39, SEQ ID NO: 45, SEQ ID NO: 46, SEQ ID NO: 47 and SEQ ID NO: 48;
(ii) a neuroprotective AP-1 signaling inhibitory peptide comprising a fusion between a protein transduction domain and a peptide comprising a sequence selected from the group consisting of SEQ ID NO: 36, SEQ ID NO: 37, SEQ ID NO: 45 and SEQ ID NO: 46;
(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions; and
(iv) a retroinverted analog of (i) or (ii) or (iii) or (iv) comprising one or more D-amino acids.

Preferred neuroprotective AP-1 signaling inhibitory peptides having neuroprotective activity in vivo are selected from the group consisting of:
(i) a neuroprotective AP-1 signaling inhibitory peptide comprising a sequence selected from the group consisting of: SEQ ID NO: 36, SEQ ID NO: 37, SEQ ID NO: 38 and SEQ ID NO: 39;
(ii) a neuroprotective AP-1 signaling inhibitory peptide comprising a fusion between a protein transduction domain and a peptide comprising a sequence selected from the group consisting of SEQ ID NO: 36 and SEQ ID NO: 37;
(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions; and
(iv) a retroinverted analog of (i) or (ii) or (iii) or (iv) comprising one or more D-amino acids.

More preferably, neuroprotective AP-1 signaling inhibitory peptides having neuroprotective activity in vivo are retroinverted peptides selected from the group consisting of:
(i) a neuroprotective AP-1 signaling inhibitory peptide comprising a sequence selected from the group consisting of: SEQ ID NO: 37 and SEQ ID NO: 39;
(ii) a neuroprotective AP-1 signaling inhibitory peptide comprising a fusion between a protein transduction domain and a peptide comprising the sequence set forth in SEQ ID NO: 37; and
(iii) a neuroprotective AP-1 signaling inhibitory peptide that is a variant of (i) or (ii) having at least about 90% or 95% sequence identity thereto and comprising a sequence that differs from a sequence set forth in (i) or (ii) by one or more conservative amino acid substitutions.

In each of the foregoing embodiments, a preferred protein transduction domain will comprise an amino acid sequence selected from the group set forth in SEQ ID NOS: 1-25, more preferably a peptide transduction domain comprising a sequence selected from the group set forth in SEQ ID NOS: 1-16 and 21-25, and still more preferably a TAT basic region peptide selected from the group set forth in SEQ ID NOS: 1-16 including one or more retroinverted analogs thereof e.g., as set forth in any one of SEQ ID NOS: 9-16. In a particularly preferred embodiment, the protein transduction domain is a TAT basic region peptide comprising the sequence set forth in SEQ ID NO: 1 or a retroinverted TAT basic region peptide comprising the sequence set forth in SEQ ID NO: 9.

It will be apparent from the sequence data provided herein that the AP-1 signaling inhibitory peptide may be separated from a protein transduction domain by one or more linkers, preferably a linker comprising from 1 to about 6 glycine residues or other amino acids of low immunogenicity e.g., serine. In a particularly preferred embodiment, the protein transduction domain is separated from the AP-1 signaling inhibitory peptide by at least one glycine residue which may be provided by the terminal amino acid of one or other peptide moiety.

In each of the foregoing embodiments by virtue of the small size of Phylomer™ peptides, conservative amino acid variants of the exemplified peptides will differ only in 1 or 2 or 3 or 4 or 5 amino acid residues. Whilst such variants will naturally possess neuroprotective activity to retain their utility in performing an method of the invention described herein below, the present invention clearly encompasses any and all such variants in so far as they possess enhanced neuroprotective function in any of the assay systems exemplified herein. Preferred amino acid substitutions producing such variants are described herein.

The present invention clearly extends to any derivatives of the exemplified neuroprotective peptides described in accordance with any one or more of the foregoing examples.

In each of the embodiments described herein, it is preferred that all amino acids in a retroinverted peptide other than glycine are D-amino acids.

The present invention also provides a neuroprotective composition comprising (i) an amount of a neuroprotective AP-1 signaling inhibitory peptides according to any one or more embodiments described herein sufficient to reduce, delay or prevent neuronal apoptosis and/or necrosis in an animal; and (ii) a suitable carrier or excipient for application to the central nervous system of the animal.

Compositions comprising multiple neuroprotective AP-1 signaling inhibitory peptides are clearly contemplated herein, for enhanced benefit. It is preferred but not essential for such compositions to comprise active ingredients having different effects or activities in vivo. For example, suitable compositions may comprise combinations of combinations of peptides PYC19 and/or PYC35 and/or PYC36 and/or PYC 38/39 and/or PYC41, and preferably a combination of PYC35 and PYC36, optionally in further combination with the JNK inhibitory peptide JNK1-1D-TAT, and preferably as fusions with protein transduction domain(s) such as TAT basic region. Certain linker residues such as glycine may be found joining the protein transduction domain with the Phylomer peptides. Again, one or more of the constituent peptides may be retroinverted.

As used herein, the term "amount sufficient to prevent or reduce neuronal apoptosis and/or necrosis in an animal" or similar term shall be taken to mean a sufficient quantity of a stated integer to reduce the number of neurons undergoing apoptosis and/or necrosis induced by a insult such as a physical injury e.g., acute cortical injury, or ischemic event in the animal. The precise amount of the stated integer will vary depending on the specific activity of the integer and/or the severity of the insult. Accordingly, this term is not to be construed to limit the invention to a specific quantity, e.g., weight or concentration, unless specifically stated otherwise. Methods for assessing efficacy of any amount of a peptide of the present invention in preventing neuronal cell death i.e., apoptosis and/or necrosis will be apparent to the skilled artisan from the disclosure herein.

As used herein, the term "suitable carrier or excipient" shall be taken to mean a compound or mixture thereof that is suitable for use in a formulation for administration to neurons or neuronal tissue albeit not necessarily limited in use to that context. Similarly, the term "carrier or excipient for neuronal application" shall be taken to mean a compound or mixture thereof that is suitable for application to neuronal tissues and which may be suitable for use in other contexts. In contrast, a "neuronal tissue carrier or excipient" is compound or mixture thereof that is described in the art only with reference to a use in formulations used on neuronal tissues.

A carrier or excipient useful in the composition of the present invention will generally not inhibit to any significant degree a relevant biological activity of the active compound e.g., the carrier or excipient will not significantly inhibit the AP-1 signaling inhibitory activity of the active peptide. For example, a carrier or excipient may merely provide a buffering activity to maintain the active compound at a suitable pH to thereby exert its biological activity, e.g., phosphate buffered saline. Alternatively, or in addition, the carrier or excipient may comprise a compound that enhances neuronal uptake of the peptide and/or enhances neuronal delivery. Alternatively, or in addition, the carrier or excipient may comprise a compound that enhances the activity or half-life of the active peptide e.g., a protease inhibitor. In yet another example, the carrier or excipient may include an antibiotic and/or an anaesthetic.

Suitable carriers for use in protecting neurons in vivo include e.g., gels, emulsions or saline in which the peptide(s) is/are substantially soluble. Particularly preferred carriers are suitable for administration by injection to neuronal tissue or alternatively, by direct application to wounded neural tissue e.g., brain lesion.

In another example, the composition of the present invention comprises an additional composition of matter having synergistic activity with respect to the active peptide in so far as neuron repair is concerned e.g., an antioxidant compound and/or stem cell.

The present invention also provides a method for producing a composition described herein according to any embodiment. For example, in its broadest form, such a method comprises mixing or otherwise combining an amount of an AP-1 signaling inhibitory peptide of the present invention sufficient to reduce or prevent neuronal cell death in an animal and a suitable carrier or excipient. In one example, the method additionally comprises producing or obtaining the AP-1 signaling inhibitory peptide. For example, a peptide inhibitor or a nucleic acid inhibitor is produced synthetically or recombinantly, using a method known in the art and/or described herein.

The present invention also provides a method for preventing or delaying neuronal cell death in a subject comprising administering an AP-1 signaling inhibitory peptide or composition comprising said peptide according to any embodiment described herein or an analog of said peptide to a subject in need of treatment.

The present invention also provides a method for preventing or delaying neuronal cell death in a subject comprising administering a composition comprising one or more AP-1 signaling inhibitory peptides according to any embodiment described herein to a subject in need of treatment.

As used herein, the term "subject in need thereof" shall be taken to mean a subject that has developed or suffers from a neuronal condition involving e.g., glutamate and/or NMDA excitotoxicity and/or ischemia and/or wounding. For example, the subject may have recently suffered from, or is likely to suffer from, cerebral ischemia, traumatic brain injury, epilepsy, Parkinson's Disease, Alzheimer's Disease and Amyotrophic Lateral Sclerosis (ALS). In view of the efficacy of certain peptides early in an ischemic event e.g., within 1-7 days and preferably within 1-4 days or the day following an ischemic event, the subject is more likely to be a subject having recently suffered local or global cerebral ischemia or traumatic brain injury e.g., following a motor vehicle accident.

Similarly, neuronal cell death treatable by the present invention is preferably induced by NMDA excitotoxicity and/or glutamate excitotoxicity and/or ischemia and/or wounding e.g., acute cortical injury.

In another example, an AP-1 signaling inhibitory peptide or composition is administered by a process comprising administering nucleic acid encoding an AP-1 signaling inhibitory peptide to a subject by particle bombardment under conditions sufficient for transcription and translation of said nucleic acid to occur.

The therapeutic method described herein is not to be limited to a single application of a peptide or composition of the invention. The present invention also contemplates repeated administration of a peptide or composition as described herein according to any embodiment e.g., to extend the period over which beneficial effects are derived.

In another example, the therapeutic method of the invention additionally comprises providing or obtaining a composition as described herein according to any embodiment or information concerning same. For example, the present invention provides a method of treatment of a subject in need thereof, said method comprising:

(i) identifying a subject suffering from or developing a neuronal condition involving e.g., glutamate and/or NMDA excitotoxicity and/or ischemia and/or wounding;
(ii) obtaining an AP-1 signaling inhibitory peptide or composition comprising said peptide as described herein according to any embodiment; and
(iii) administering said peptide or composition to said subject.

The present invention also provides a method of treatment of a subject in need thereof, said method comprising:
(i) identifying a subject suffering from or developing a neuronal condition involving e.g., glutamate and/or NMDA excitotoxicity and/or ischemia and/or wounding; and
(ii) recommending administration of AP-1 signaling inhibitory peptide or composition comprising said peptide as described herein according to any embodiment.

Alternatively, the method of treatment comprises administering or recommending administration of AP-1 signaling inhibitory peptide or composition comprising said peptide as described herein according to any embodiment to a subject previously identified as suffering from a neuronal condition involving e.g., glutamate and/or NMDA excitotoxicity and/or ischemia and/or wounding.

The present invention also provides for the use of an amount of an AP-1 signaling inhibitory peptide as described herein according to any embodiment sufficient to inhibit or delay neuronal cell death in the manufacture of a medicament for the treatment of a neuronal condition involving e.g., glutamate and/or NMDA excitotoxicity and/or ischemia and/or wounding.

MTS data were expressed as percentage neuronal viability with no insult control taken as 100% viability and insult control as 5% viability (mean±SEM; n=4; *p<0.005; **p<0.0001).

Figure 6:
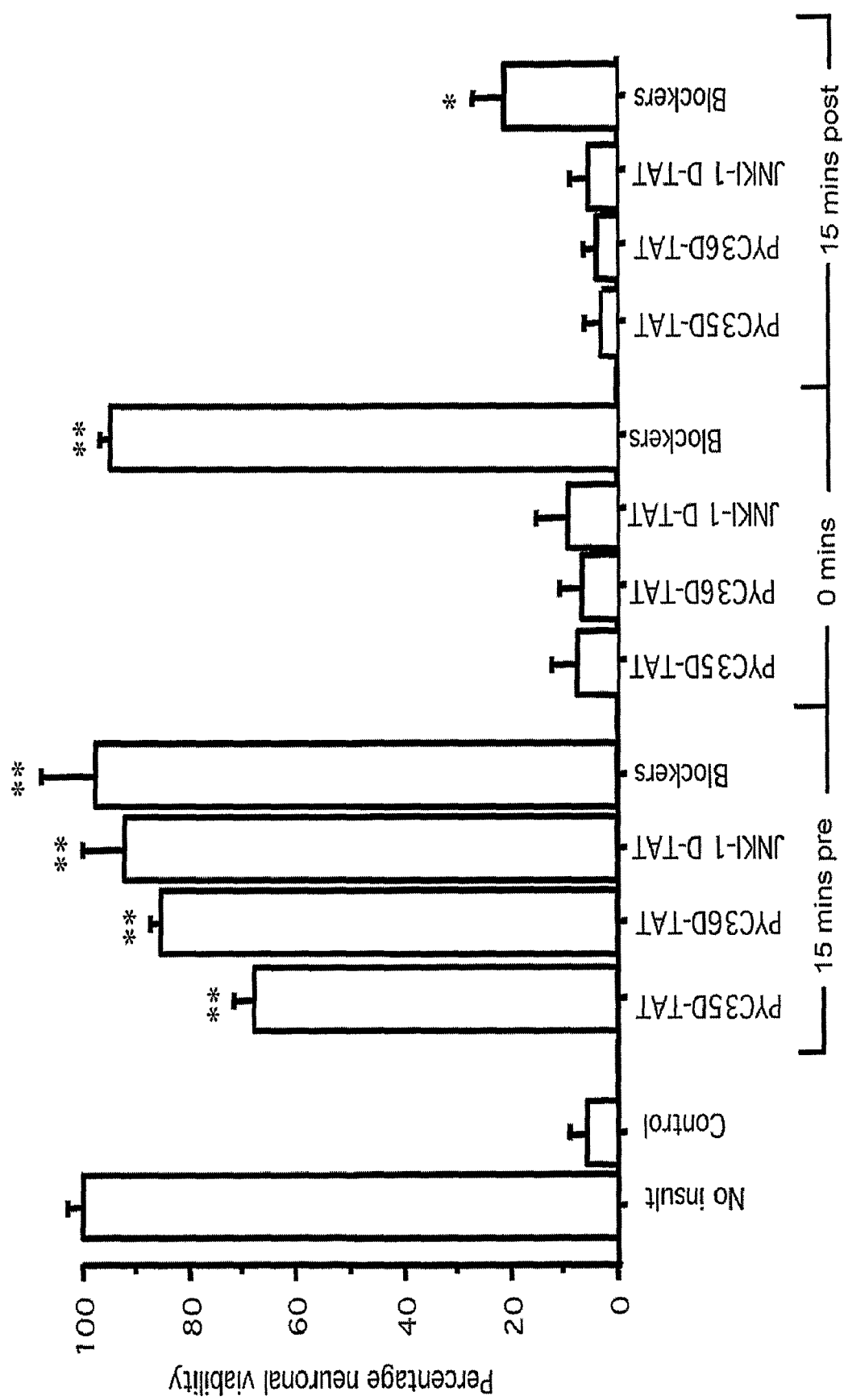

FIG. 6 provides a graphical representation showing, on the y-axis the percentages of viable neurons in culture in the presence of 5 µM extracellular concentration of the Phylomer™ peptides PYC35D-TAT and PYC36D-TAT administered 15 min prior to incubation with glutamate to induce excitotoxicity ("15 mins pre"), or alternatively, at the same time as incubation with glutamate ("0 mins") or 15 min following incubation with glutamate ("15 mins post"). Controls consisted of neuron cultures grown without glutamate (No insult), or without added peptide (Control), or neuron cultures incubated with glutamate in the presence of the peptide JNK1-1D-TAT or glutamate receptor inhibitors (Blockers) added 15 min prior to incubation with glutamate to induce excitotoxicity ("15 mins pre"), at the same time as incubation with glutamate ("0 mins") or 15 min following incubation with glutamate ("15 mins post"). MTS data were expressed as percentage neuronal viability with no insult control taken as 100% viability and insult control as 5% viability (mean±SEM; n=4; *p<0.005; **p<0.0001).

Figure 7A:
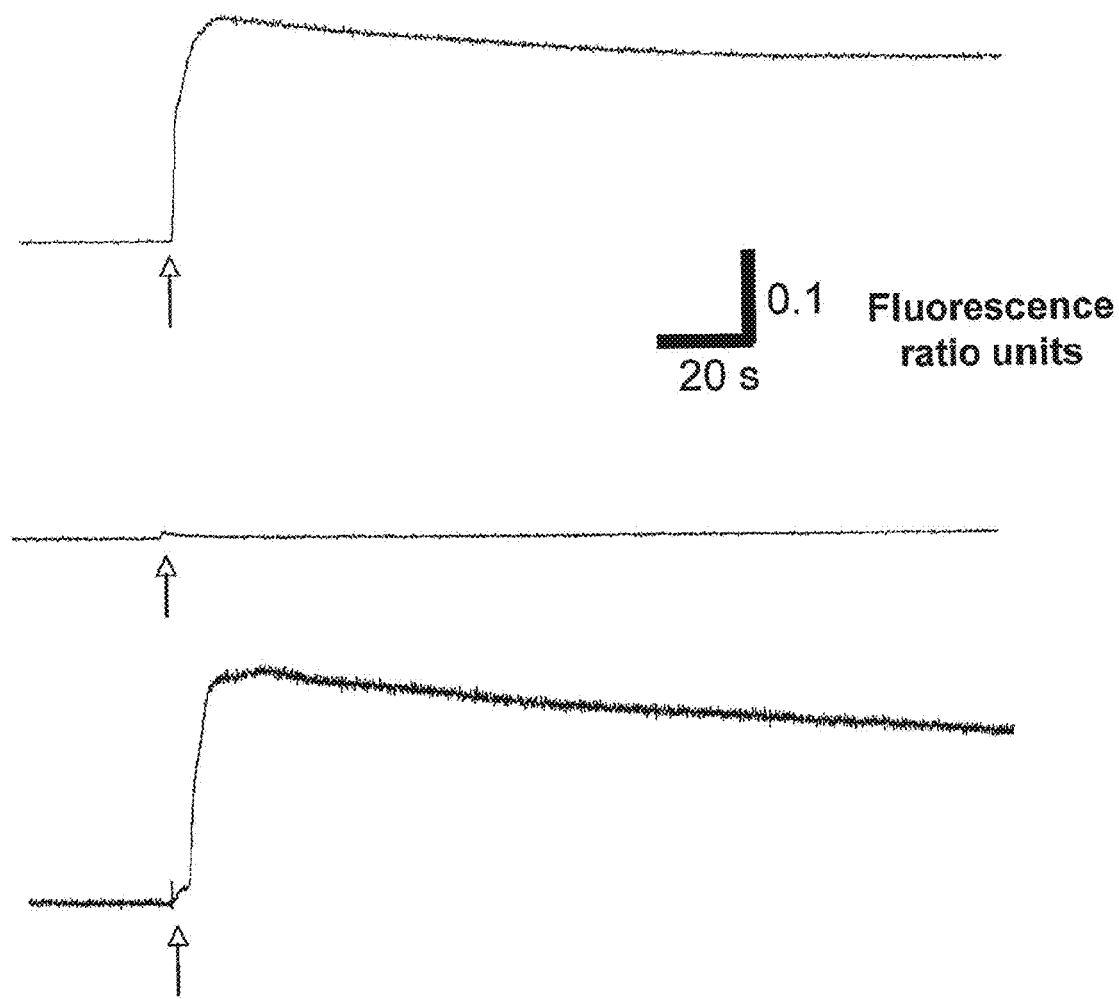

FIG. 7A provides graphical representations showing the time course of calcium influx in cortical neurons exposed to glutamate (30 second time point; arrow) in the presence of Phylomer™ peptide PYC36D-TAT (lower panel), compared to neurons not receiving glutamate (top panel) or receiving glutamate receptor inhibitors (middle panel).

Figure 7B:
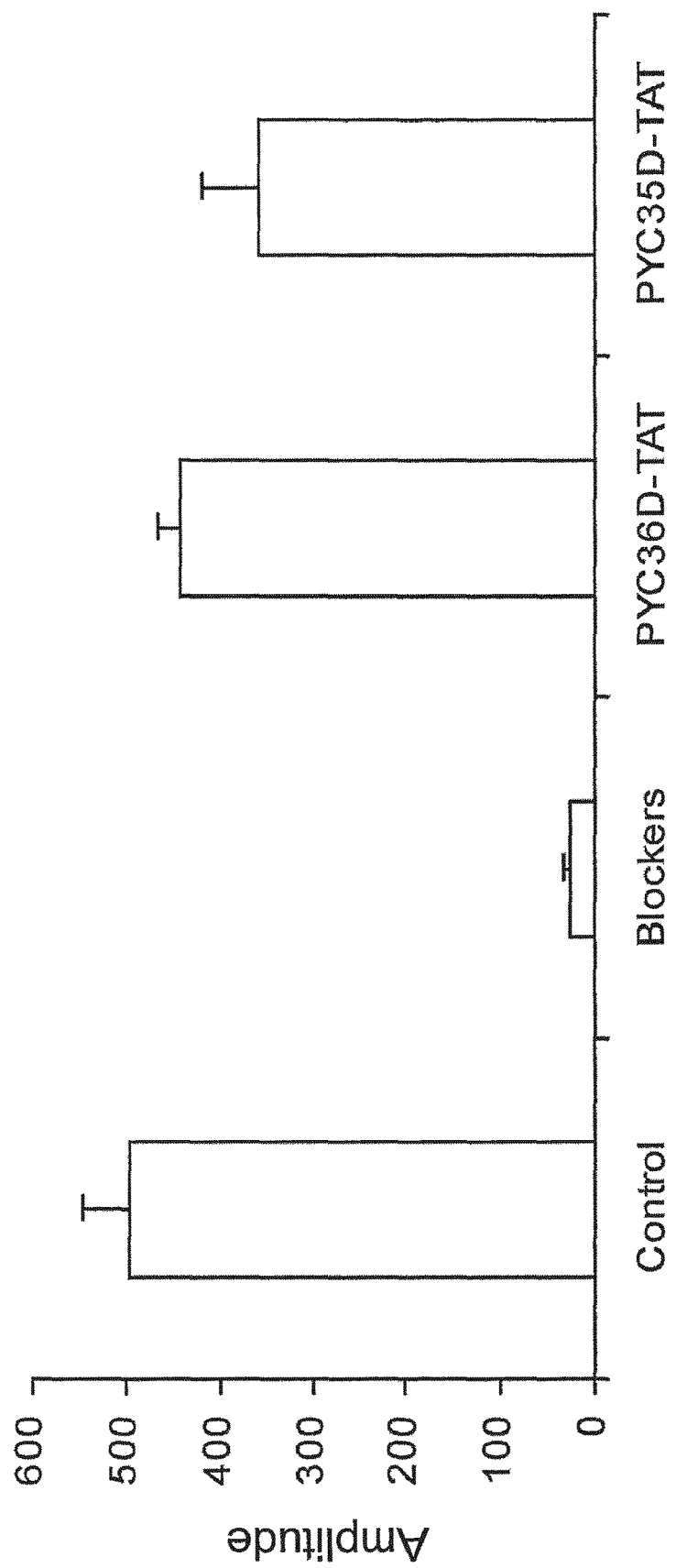

FIG. 7B provides a graphical representation showing the amplitude (y-axis) between basal $Ca^{2+}$ level and peak $Ca^{2+}$ level for neuron cultures in the absence and presence of glutamate, for each condition indicated on the x-axis. Control: No added peptide or receptor inhibitor in the presence and absence of glutamate; Blockers: glutamate receptor inhibitors added in the presence and absence of glutamate; PYC5D-TAT, the Phylomer™ peptide PYC35D-TAT was added in the presence and absence of glutamate; and PYC36D-TAT, the Phylomer™ peptide PYC36D-TAT was added in the presence and absence of glutamate.

Figure 8:
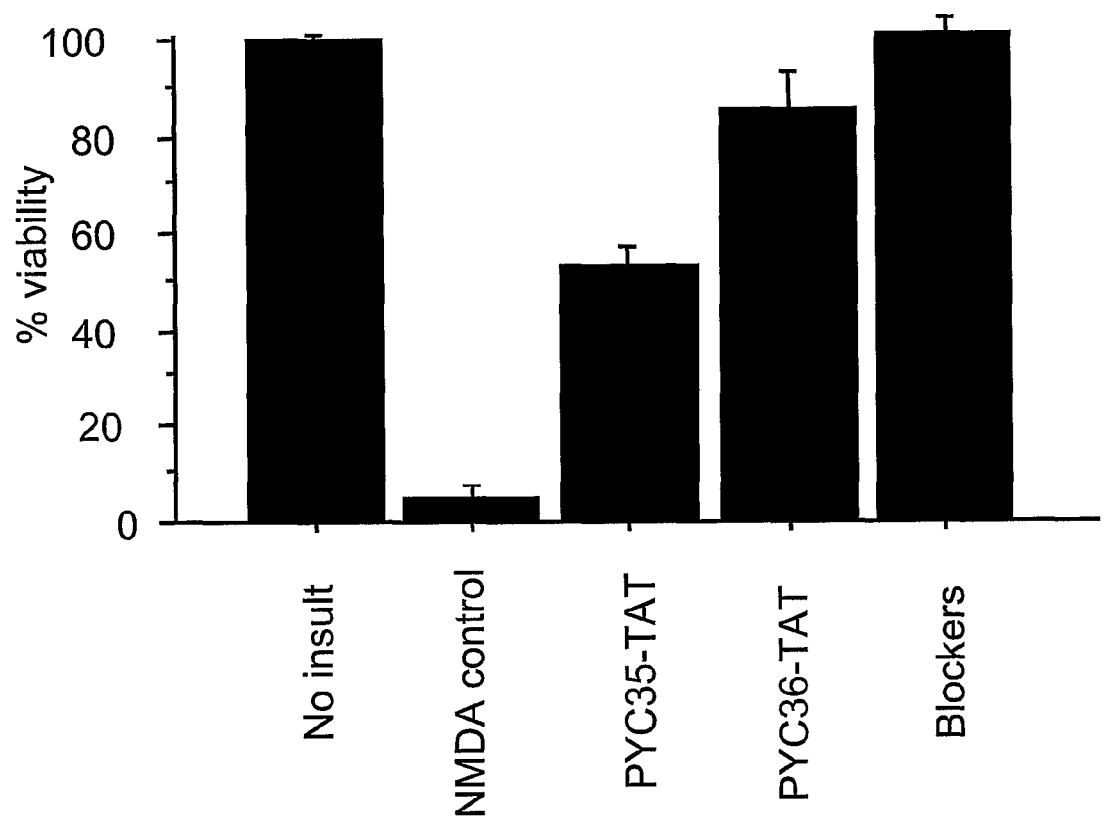

FIG. 8 provides a graphical representation showing, on the y-axis the percentages of viable neurons in culture in the presence of 5 µM extracellular concentration of the Phylomer™ peptides PYC35D-TAT and PYC36D-TAT administered 15 min prior to incubation with NMDA to induce excitotoxicity. Controls consisted of neuron cultures grown without NMDA (No insult), or without added peptide (NMDA Control), or neuron cultures incubated with NMDA in the presence of glutamate receptor inhibitors (Blockers). MTS data were expressed as percentage neuronal viability with no insult control taken as 100% viability and insult control as 5% viability (mean±SEM; n=4; *p<0.005; **p<0.0001).

Figure 9:
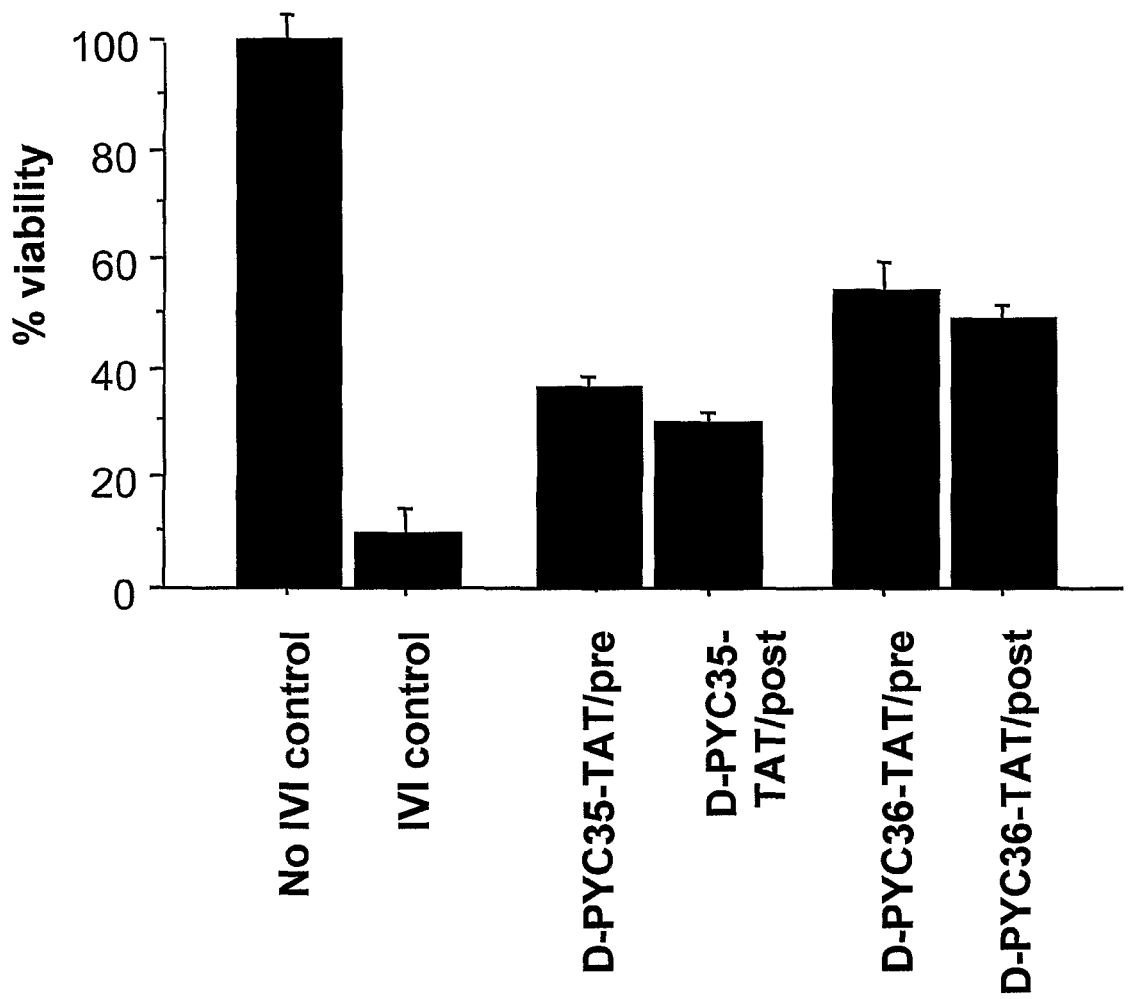

FIG. 9 is a graphical representation showing the ability of retroinverted Phylomer™ peptides to protect cultured cortical neurons in an in vitro model of ischemia known as Oxygen Glucose Deprivation (OGD). Neuronal survival (5) (y-axis) was determined in the absence ("No IVI control") or following 35 min OGD in the absence of exogenously-added peptide ("IVI Control") or in the presence of peptides PYC35D-TAT or PYC36D-TAT added before ("pre") or after ("post") commencement of OGD.

Figure 10:
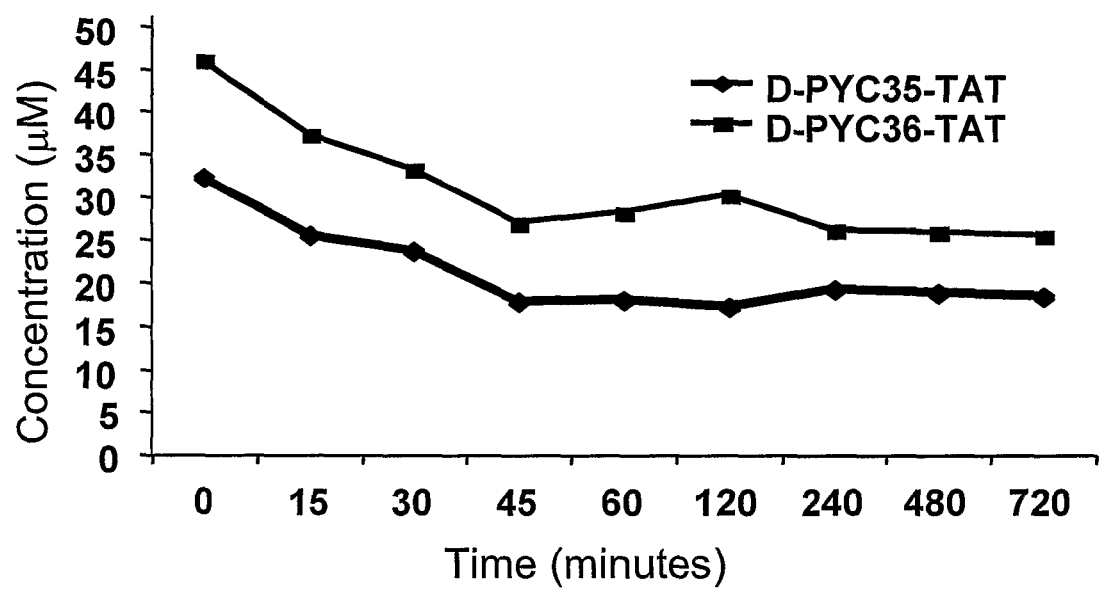

FIG. 10 is a graphical representation showing the stability of retroinverted Phylomer™ peptides in serum. Peptide concentration (µM) is shown on the y-axis at various time points (min) after administration to animals as indicated on the x-axis. Neuronal survival (y-axis) was determined in the absence ("No IVI control") or following 35 min OGD in the absence of exogenously-added peptide ("IVI Control") or in the presence of peptides PYC35D-TAT or PYC36D-TAT added before ("pre") or after ("post") commencement of OGD.

Figure 11:
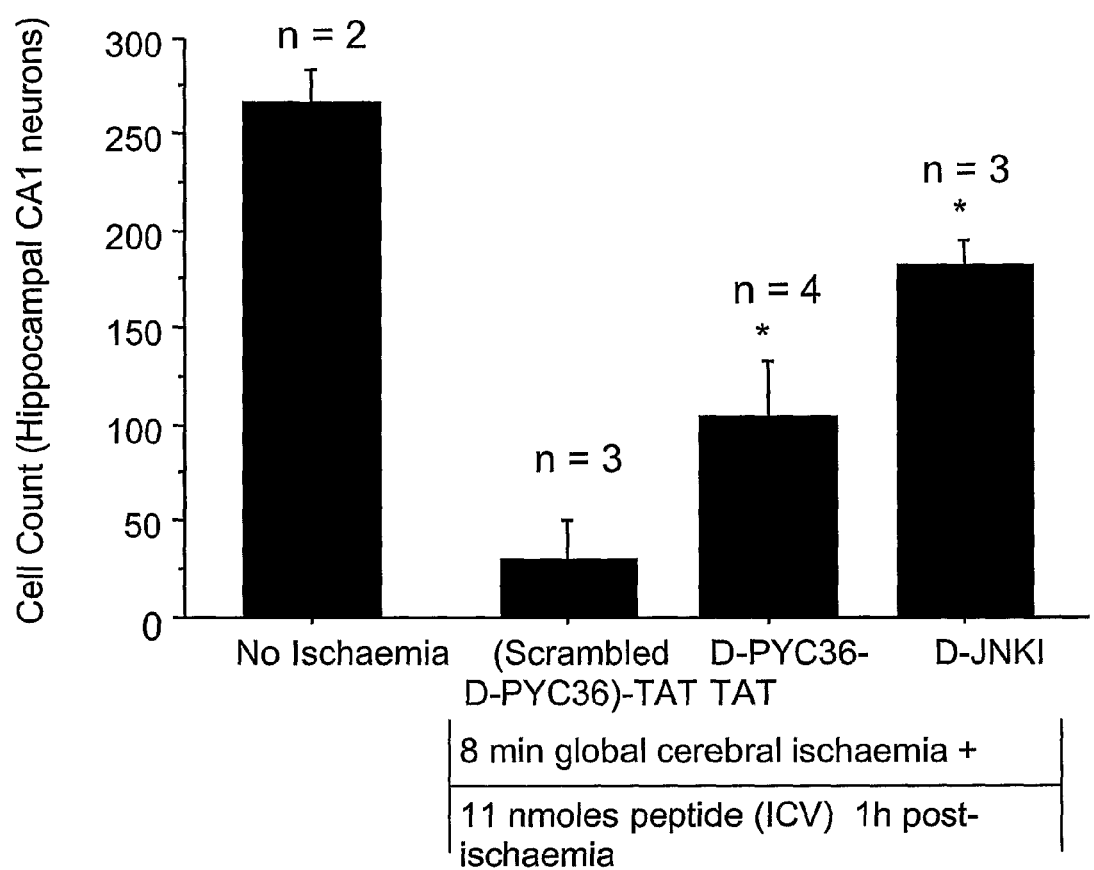

FIG. 11 is a graphical representation showing the extent of neuronal loss in the perilesion area 1 day post-injury following administration of Phylomer™ peptides PYC35D-TAT and PYC36D-TAT, and the peptide JNK1-1D-TAT, as determined by hippocampal CA1 cell count. As a negative control, hippocampal CA1 cell count was determined following administration of PYC35D Scram-TAT peptide, containing the scrambled sequence of PYC35D was employed. Hippocampal CA1 cell counts were also determined for sham-treated animals, and for animals receiving saline (NaCl). Values are expressed as the loss of MAP2 immunoreactive area ($mm^2$).

Figure 12:
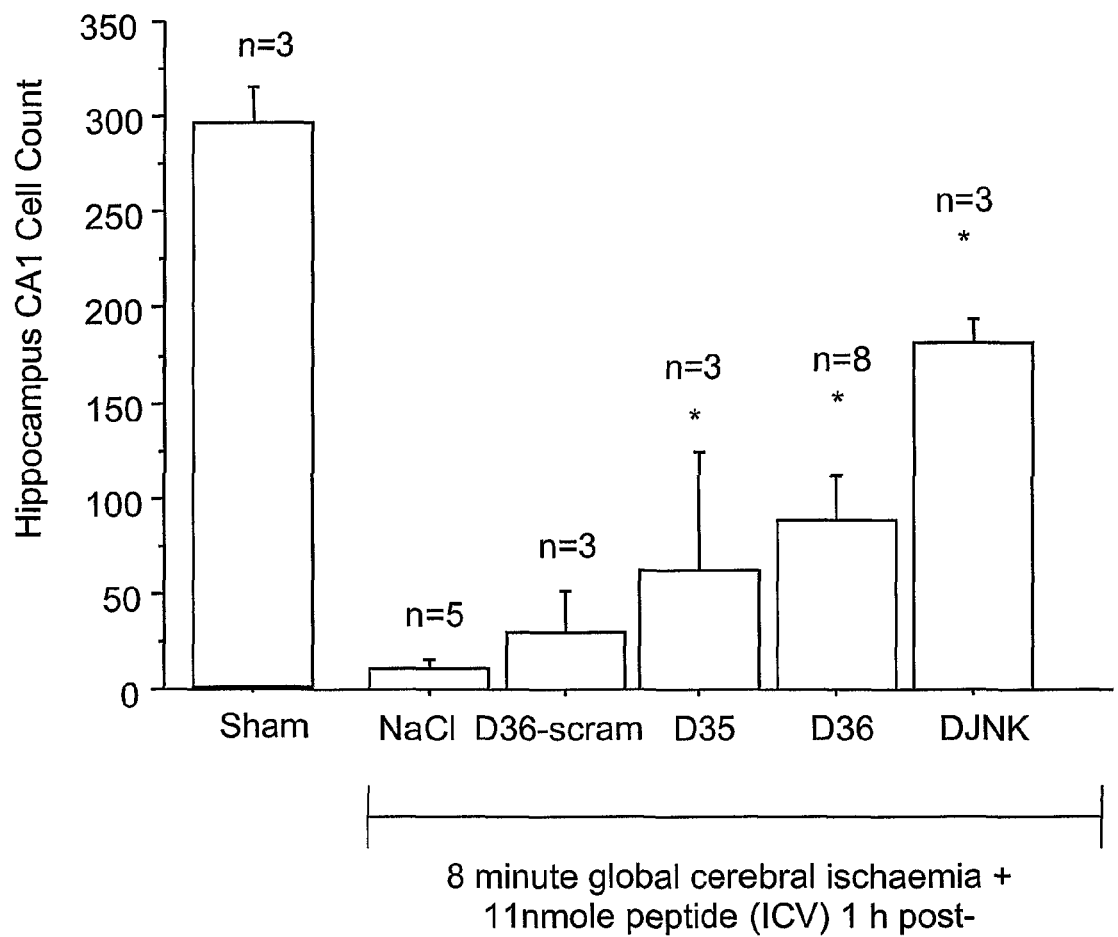

FIG. 12 is a graphical representation showing the extent of neuronal loss in the perilesion area 1 day post-injury following administration of Phylomer peptides PYC35D-TAT and PYC36D-TAT, and the peptide JNK1-1D-TAT, as determined by loss of MAP immunoreactivity ($mm^2$) 1 day post injury following administration of Phylomer™ peptide PYC35D-TAT, the negative control peptide PYC35D Scram-TAT, or the peptide JNK1-1D-TAT.

Figure 13:
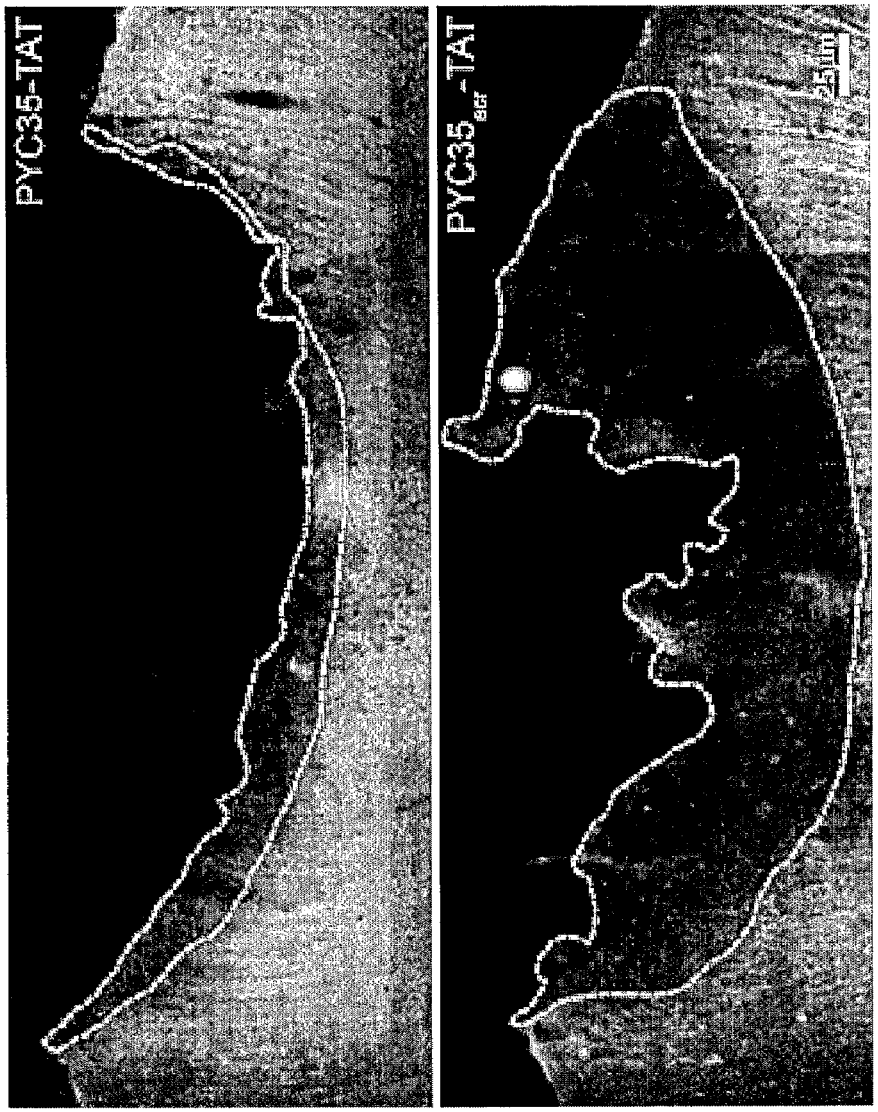

FIG. 13 is a copy of a photomicrograph showing loss of MAP immunoreactivity (area enclosed by dotted line) in perilesion area 1 day post injury following administration of Phylomer™ PYC35D-TAT or negative control peptide (PYC35D Scram-TAT). Size bar 25 µm.

DETAILED DESCRIPTION OF THE PREFERRED EMBODIMENTS

Peptide Inhibitors of AP-1 Signaling

As exemplified herein, the present inventors have identified a number of neuroprotective AP-1 signaling inhibitory peptides that partially or completely inhibit c-Jun homodimerization and/or c-Jun heterodimerization and/or one or more upstream signaling steps in the AP-1 signaling pathway e.g., Cdc42 and/or Rac1 and/or Pak1 and/or MKK (Table 1), thereby preventing, delaying or reducing neuronal cell death by apoptotic and/or necrotic pathways. The peptides partially or completely decrease, prevent or inhibit neuronal cell death mediated by glutamate excitotoxicity and/or NMDA excitotoxicity, albeit not necessarily at the level of the glutamate/NMDA receptor. Additionally, the peptides have been shown herein to be neuroprotective in models of local and global ischemia in vitro as well as in vivo.

The present invention clearly extends to variants of the exemplified neuroprotective AP-1 signaling inhibitory peptides, such as derivatives and/or analogs, by modification to the sequences provided herein. The invention also extends to homologs i.e., functionally-equivalent peptides having related sequences to the sequences provided herein e.g., using different expression libraries to those used as a source of the neuroprotective peptides described herein.

It is understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which specific amino acids may be substituted or deleted. Particular embodiments encompass variants that have one, two, three, four, five or more variations in the amino acid sequence relative to a base peptide subject to the retention of neuroprotective function in one or more assays described in the examples. Of course, a plurality of variants may be made and used in accordance with the invention.

Peptide Derivatives

As used herein the term "derivative" shall be taken to mean a peptide that is derived from an AP-1 signaling inhibitory peptide exemplified herein e.g., a fragment or processed form of the peptide, or a molecule comprising one or more amino acid substitutions, or comprising additional amino acid residues or non-amino acid substituents, relative to the base peptide from which it is derived. The term "derivative" also encompasses fusion proteins comprising a peptide of the invention.

Exemplary fusion protein comprises a label, such as, for example, an epitope, e.g., a FLAG epitope or a V5 epitope or an HA epitope. Such a tag is useful for, for example, purifying the fusion protein.

A "conservative amino acid substitution" is one in which an amino acid residue is replaced with another amino acid residue without disturbing the overall structure of the peptide. Such changes tend to rely on similarity in hydrophilicity and/or polarity of the substituent. The size and/or charge of the side chains also are relevant factors in determining which substitutions are conservative. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), .beta.-branched side chains (e.g., threonine, valine, isoleucine) and aromatic side chains (e.g., tyrosine, phenylalanine, tryptophan, histidine).

Those skilled in the art are well aware that the following substitutions are permissible conservative substitutions (i) substitutions involving arginine, lysine and histidine; (ii) substitutions involving alanine, glycine and serine; and (iii) substitutions involving phenylalanine, tryptophan and tyrosine.

The importance of the hydropathic amino acid index in conferring interactive biological function on a protein is generally understood in the art (Kyte & Doolittle, *J. Mol. Biol.* 157, 105-132, 1982). It is known that certain amino acids may be substituted for other amino acids having a similar hydropathic index or score and still retain a similar biological activity. The hydropathic index of amino acids also may be considered in determining a conservative substitution that produces a functionally equivalent molecule. Each amino acid has been assigned a hydropathic index on the basis of their hydrophobicity and charge characteristics, as follows: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making changes based upon the hydropathic index, the substitution of amino acids whose hydropathic indices are within .+/−0.2 is preferred. More preferably, the substitution will involve amino acids having hydropathic indices within .+/−0.1, and more preferably within about +/−0.05.

It is also understood in the art that the substitution of like amino acids is made effectively on the basis of hydrophilicity, particularly where the biological functional equivalent protein or peptide thereby created is intended for use in immunological embodiments, as in the present case (e.g. U.S. Pat. No. 4,554,101), In fact, the greatest local average hydrophilicity of a protein, as governed by the hydrophilicity of its adjacent amino acids, correlates with its immunogenicity and antigenicity. As detailed in U.S. Pat. No. 4,554,101, the following hydrophilicity values have been assigned to amino acid residues: arginine (+3.0); lysine (+3.0); aspartate (+3.0+/−0.1); glutamate (+3.0+/−0.1); serine (+0.3); asparagine (+0.2); glutamine (+0.2); glycine (0); threonine (−0.4); proline (−0.5+/−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is preferred to substitute amino acids having hydrophilicity values within about +/−0.2 of each other, more preferably within about +/−0.1, and even more preferably within about +/−0.05

Non-amino acid substituents may be linked covalently to a peptide e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound. For example, particular peptide residues may be derivatized or chemically modified in order to enhance the stability of the peptide or to permit coupling of the peptide to other agents, particularly lipids.

Chemical moieties may be linked covalently to a peptidyl moiety e.g., via an amino terminal amino acid residue, a carboxy terminal amino acid residue, or at an internal amino acid residue. Such modifications include the addition of a protective or capping group on a reactive moiety in the peptide, addition of a detectable label, and other changes that do not adversely destroy the activity of the peptide compound.

An "amino terminal capping group" of a peptide described herein is any chemical compound or moiety that is covalently linked or conjugated to the amino terminal amino acid residue of a peptide compound. An amino terminal capping group may be useful to inhibit or prevent intramolecular cyclization or intermolecular polymerization, to promote transport of the peptide compound across the blood-brain barrier (BBB), to protect the amino terminus from an undesirable reaction with other molecules, to provide additional antioxidative activity, or to provide a combination of these properties. A peptide compound of this invention that possesses an amino terminal capping group may possess other beneficial activities as compared with the uncapped peptide, such as enhanced efficacy or reduced side effects. Examples of amino terminal capping groups that are useful in preparing peptide compounds and compositions according to this invention include, but are not limited to, 1 to 6 naturally occurring L-amino acid residues, preferably, 1-6 lysine residues, 1-6 arginine residues, or a combination of lysine and arginine residues; urethanes; urea compounds; lipoic acid ("Lip"); glucose-3-O-glycolic acid moiety ("Gga"); or an acyl group that is covalently linked to the amino terminal amino acid residue of a peptide, wherein such acyl groups useful in the compositions of the invention may have a carbonyl group and a hydrocarbon chain that ranges from one carbon atom (e.g., as in an acetyl moiety) to up to 25 carbons (e.g., palmitoyl group, "Palm" (16:0) and docosahexaenoyl group, "DHA" (C22:6-3)). Furthermore, the carbon chain of the acyl group may be saturated, as in Palm, or unsaturated, as in DHA. It is understood that when an acid, such as docosahexaenoic acid, palmitic acid, or lipoic acid is designated as an amino terminal capping group, the resultant peptide compound is the condensed product of the uncapped peptide and the acid.

A "carboxy terminal capping group" of a peptide compound described herein is any chemical compound or moiety that is covalently linked or conjugated to the carboxy terminal amino acid residue of the peptide compound. The primary purpose of such a carboxy terminal capping group is to inhibit or prevent intramolecular cyclization or intermolecular polymerization, to promote transport of the peptide compound across the blood-brain barrier, and to provide a combination of these properties. A peptide compound of this invention possessing a carboxy terminal capping group may also possess other beneficial activities as compared with the uncapped peptide, such as enhanced efficacy, reduced side effects, enhanced hydrophilicity, enhanced hydrophobicity. Carboxy terminal capping groups that are particularly useful in the peptide compounds described herein include primary or secondary amines that are linked by an amide bond to the .alpha.-carboxyl group of the carboxy terminal amino acid of the peptide compound. Other carboxy terminal capping groups useful in the invention include aliphatic primary and secondary alcohols and aromatic phenolic derivatives, including flavenoids, with 1 to 26 carbon atoms, which form esters when linked to the carboxylic acid group of the carboxy terminal amino acid residue of a peptide compound described herein.

Other chemical modifications of a peptide or analog, include, for example, glycosylation, acetylation (including N-terminal acetylation), carboxylation, carbonylation, phosphorylation, PEGylation, amidation, addition of trans olefin, substitution of α-hydrogens with methyl groups, derivatization by known protecting/blocking groups, circularization, inhibition of proteolytic cleavage (e.g., using D amino acids), linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$, acetylation, formylation, oxidation, reduction, etc.

Peptide Analogs

In another example of the invention, an AP-1 signaling inhibitory peptide analog is prepared. As used herein, the term "analog" shall be taken to mean a peptide that is modified to comprise one or more non-naturally-occurring amino acids.

Analogs may also comprise sterically similar compounds that mimic critical subdomains of a peptide. Such "peptidomimetics" are produced by modelling and chemical design processes known to those of skill in the art.

Preferred analogs of an AP-1 signaling inhibitory peptides comprise one or more non-naturally occurring amino acids or amino acid analogs. For example, a peptide inhibitor as described herein comprises one or more naturally occurring non-genetically encoded L-amino acids, synthetic L-amino acids or D-enantiomers of an amino acid. For example, the peptide comprises only D-amino acids. For example, the analog comprises one or more residues selected from the group consisting of: hydroxyproline, β-alanine, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylananine 3-benzothienyl alanine 4-chlorophenylalanine, 2-fluorophenylalanine, 3-fluorophenylalanine, 4-fluorophenylalanine, penicillamine, 1,2,3,4-tetrahydro-tic isoquinoline-3-carboxylic acid β-2-thienylalanine, methionine sulfoxide, homoarginine, N-acetyl lysine, 2,4-diamino butyric acid, ρ-aminophenylalanine, N-methylvaline, homocysteine, homoserine, ε-amino hexanoic acid, δ-amino valeric acid, 2,3-diaminobutyric acid and mixtures thereof.

Other amino acid residues that are useful for making the peptides and peptide analogs described herein can be found, e.g., in Fasman, 1989, CRC Practical Handbook of Biochemistry and Molecular Biology, CRC Press, Inc., and the references cited therein.

The present invention additionally encompasses an isostere of a peptide described herein. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) known to those skilled in the art. Such modifications include modifications of the amide nitrogen, the α-carbon, amide carbonyl, complete replacement of the amide bond, extensions, deletions or backbone crosslinks. Several peptide backbone modifications are known, including $\psi[CH_2S]$, $\psi[CH_2NH]$, $\psi[CSNH_2]$, $\psi[NHCO]$, $\psi[COCH_2]$, and $\psi[(E)$ or $(Z) CH=CH]$. In the nomenclature used above, ψ indicates the absence of an amide bond. The structure that replaces the amide group is specified within the brackets.

Other modifications include, for example, an N-alkyl (or aryl) substitution (ψ[CONR]), or backbone crosslinking to construct lactams and other cyclic structures. Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides.

In another example, a peptide analog is a retro peptide (see, for example, Goodman et al., *Accounts of Chemical Research*, 12:1-7, 1979). A retro peptide comprises a reversed amino acid sequence of a peptide inhibitor described herein. Optionally, the retro peptide analog comprises an additional feature, such as, for example, a protein transduction domain, which may also be a retro peptide.

In a further example, an analog of a peptide described herein is a retro-inverso peptide (Sela and Zisman, *FASEB J.* 11:449, 1997). Evolution has ensured the almost exclusive occurrence of L-amino acids in naturally occurring proteins. As a consequence, virtually all proteases cleave peptide bonds between adjacent L-amino acids. Accordingly, artificial proteins or peptides composed of D-amino acids are preferably resistant to proteolytic breakdown. Retro-inverso peptide analogs are isomers of linear peptides in which the direction of the amino acid sequence is reversed (retro) and the chirality, D- or L-, of one or more amino acids therein is inverted (inverso) e.g., using D-amino acids rather than L-amino acids, e.g., Jameson et al., *Nature*, 368, 744-746 (1994); Brady et al., *Nature*, 368, 692-693 (1994). The net result of combining D-enantiomers and reverse synthesis is that the positions of carbonyl and amino groups in each amide bond are exchanged, while the position of the side-chain groups at each alpha carbon is preserved. An advantage of retro-inverso peptides is their enhanced activity in vivo due to improved resistance to proteolytic degradation, i.e., the peptide has enhanced stability. (e.g., Chorev et al., Trends Biotech. 13, 438-445, 1995).

Retro-inverso or retroinverted peptide analogs may be complete or partial. Complete retro-inverso peptides are those in which a complete sequence of a peptide described herein is reversed and the chirality of each amino acid other than glycine in a sequence is inverted. The exclusion of glycine is based on the fact that glycine does not have a chiral analog. Partial retro-inverso peptide analogs are those in which only some of the peptide bonds are reversed and the chirality of only those amino acid residues in the reversed portion is inverted. For example, one or two or three or four or five or six or seven or eight or nine or ten or eleven or twelve or thirteen or fourteen or fifteen or sixteen or seventeen or eighteen or nineteen or twenty or twenty one or twenty two or twenty three or twenty four or twenty five or twenty six or twenty seven or twenty eight or twenty nine or thirty or thirty one or thirty two or thirty three or thirty four or thirty five or thirty six or thirty seven or thirty eight amino acid residues are D-amino acids. The present invention clearly encompasses both partial and complete retro-inverso peptide analogs. Such a retroinverso peptide analog may optionally include an additional component, such as, for example, a protein transduction domain, which may also be retroinverted.

In one embodiment, the retro-inverso peptide is N-terminally modified, for example, with a modifying group comprising an alkyl group such as a C1-C6 lower alkyl group, e.g., a methyl, ethyl, or propyl group; or a cyclic, heterocyclic, polycyclic or branched alkyl group, or one or more an amino acid linker residues.

In another embodiment, the retro-inverso peptide is C-terminally modified, for example with an amide group, an alkyl or aryl amide group (e.g., phenethylamide) or a hydroxy group (i.e., the reduction product of a peptide acid, resulting in a peptide alcohol), or one or more an amino acid linker residues e.g., glycine, cysteine, etc.

It is also within the scope of the present invention for the retro-inverso peptide to be further modified by the inclusion of one or more targeting domains e.g., penetratin, TAT etc added to the N-terminus and/or C-terminus. Such peptide additions may be separated from the retro-inverso peptide moiety by one or more linkers e.g., glycine, serine, cysteine, etc.

Protein Transduction Domains

To facilitate peptide entry into a cell, the peptide may be conjugated to (e.g., expressed as a fusion with) a protein transduction domain. As used herein, the term "protein transduction domain" shall be taken to mean a peptide or protein that is capable of enhancing, increasing or assisting penetration or uptake of a compound conjugated to the protein transduction domain into a cell either in vitro or in vivo. Those skilled in the art will be aware that synthetic or recombinant peptides can be delivered into cells through association with a protein transduction domain such as the TAT sequence from HIV or the Penetratin sequence from the Antennapaedia homeodomain protein (see, for example, Temsamani and Vidal, *Drug Discovery Today* 9: 1012-1019, 2004, for review).

A suitable protein transduction domain will be apparent to the skilled artisan and includes, for example, native conformations and retroinverted forms of HIV-1 TAT basic region (e.g., SEQ ID NOS: 1-16), Kaposi fibroblast growth factor (FGF) protein transduction domain (e.g., SEQ ID NOS: 17-20), signal sequence based peptide 1 (e.g., SEQ ID NO: 21), signal sequence based peptide 2 (e.g., SEQ ID NO: 22), transportan (e.g., SEQ ID NO: 23), amphiphilic model peptide (e.g., SEQ ID NO: 24) or polyarginine (e.g., SEQ ID NO: 25).

Additional suitable protein transduction domains are described, for example, by Zhao and Weisledder *Medicinal Research Reviews*, 24: 1-12, 2004; or by Wagstaff and Jans, *Current Medicinal Chemistry*, 13: 1371-1387, 2006.

Linkers

The "core" AP-1 signaling inhibitory Phylomer™ peptide (e.g., identified e.g., by virtue of its ability to block c-Jun dimerization in yeast and/or to block AP-1 regulated luciferase reporter gene expression in mammalian cells) may be linked to another peptidyl moiety (e.g., for immunodetection such as a FLAG epitope, or for targeting such as a protein transduction domain), albeit separated there from by a linker.

Preferred linkers facilitate the independent folding of each peptidyl moiety in the assembled AP-1 signaling inhibitory peptide, thereby reducing steric hindrance of one moiety by another moiety. The amino acid composition of a linker peptide is important for stability and folding of a fusion protein, rather than a specific sequence (Robinson and Sauer *Proc. Natl. Acad. Sci.* 95: 5929-5934, 1998).

Suitable linkers will be apparent to the skilled artisan and are predominantly hydrophilic, i.e. the residues in the linker are hydrophilic.

It is also often unfavourable to utilize a linker sequence having a high propensity to adopt α-helix or β-strand structures, which could limit the flexibility of the peptidyl moieties and reduce functionality. Accordingly, preferred linkers may have a preference to adopt extended conformations.

Preferred linkers comprise a high content of glycine and/or serine residues. Linkers comprising glycine and/or serine have a high freedom degree for linking of two proteins, i.e., they enable the fused proteins to fold and produce functional proteins.

Glycine-rich linkers are particularly preferred because they force the linker to adopt a loop conformation. The absence of a β-carbon from glycine also permits the polypeptide backbone to access dihedral angles that are energetically forbidden for other amino acids. A particularly preferred linker in the present context consists of polyglycine i.e., between about 2 and 6 glycine residues, or a single glycine residue.

Chemical Synthesis of Peptides and Peptide Analogs

AP-1 signaling inhibitory peptides and any derivatives, analogs or homologs thereof are readily synthesized from their determined amino acid sequences using standard techniques, e.g., using BOC or FMOC chemistry. Synthetic peptides are prepared using known techniques of solid phase, liquid phase, or peptide condensation, or any combination thereof, and can include natural and/or unnatural amino acids. Amino acids used for peptide synthesis may be standard Boc (Nα-amino protected Nα-t-butyloxycarbonyl)amino acid resin with the deprotecting, neutralization, coupling and wash protocols of the original solid phase procedure of Merrifield, *J. Am. Chem. Soc.*, 85:2149-2154, 1963, or the base-labile Nα-amino protected 9-fluorenylmethoxycarbonyl (Fmoc) amino acids described by Carpino and Han, *J. Org. Chem.*, 37:3403-3409, 1972. Both Fmoc and Boc Nα-amino protected amino acids can be obtained from various commercial sources, such as, for example, Fluka, Bachem, Advanced Chemtech, Sigma, Cambridge Research Biochemical, Bachem, or Peninsula Labs.

The Merrifield method of synthesis (Merrifield, *J Am Chem Soc*, 85:2149-2154, 1963) and the myriad of available improvements on that technology are described in the art (see e.g., Synthetic Peptides: A User's Guide, Grant, ed. (1992) W.H. Freeman & Co., New York, pp. 382; Jones (1994) The Chemical Synthesis of Peptides, Clarendon Press, Oxford, pp. 230.); Barany, G. and Merrifield, R. B. (1979) in *The Peptides* (Gross, E. and Meienhofer, J. eds.), vol. 2, pp. 1-284, Academic Press, New York; Wünsch, E., ed. (1974) *Synthese von Peptiden in Houben-Weyls Metoden der Organischen Chemie* (Müler, E., ed.), vol. 15, 4th edn., Parts 1 and 2, Thieme, Stuttgart; Bodanszky, M. (1984) *Principles of Peptide Synthesis*, Springer-Verlag, Heidelberg; Bodanszky, M. & Bodanszky, A. (1984) *The Practice of Peptide Synthe-* sis, Springer-Verlag, Heidelberg; Bodanszky, M. (1985) *Int. J. Peptide Protein Res.* 25, 449-474.

Generally, chemical synthesis methods comprise the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis. Synthesis. Biology, Vol. 1, for classical solution synthesis. These methods are suitable for synthesis of a peptide of the present invention or an analog or derivative thereof.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

A peptide, analog or derivative as described herein can also be chemically prepared by other methods such as by the method of simultaneous multiple peptide synthesis. See, e.g., Houghten *Proc. Natl. Acad. Sci. USA* 82: 5131-5135, 1985 or U.S. Pat. No. 4,631,211.

Synthetic peptides may also be produced using techniques known in the art and described, for example, in Stewart and Young (In: Solid Phase Synthesis, Second Edition, Pierce Chemical Co., Rockford, Ill. (1984) and/or Fields and Noble (*Int. J. Pept. Protein Res.*, 35:161-214, 1990), or using automated synthesizers.

Phylomer™ peptides may also be produced in synthetic form as true cyclic peptides. Alternatively they may be cyclized following synthesis via the formation of a covalent bond between the termini such as the oxidation of flanking cystein residues or by the formation of a thioester or peptidyl bond.

Recombinant Peptide Production

AP-1 signaling inhibitory peptides of the present invention and any derivatives, analogs or homologs thereof are readily synthesized by recombinant means using methods known in the art. For example, nucleic acid encoding a peptide is synthesized from the deduced amino acid sequence (e.g., as set forth in Table 1).

To facilitate the production of a recombinant peptide or fusion protein nucleic acid encoding same is preferably isolated or synthesized. Typically the nucleic acid encoding the constituent components of the fusion protein is/are isolated using a known method, such as, for example, amplification (e.g., using PCR or splice overlap extension) or isolated from nucleic acid from an organism using one or more restriction enzymes or isolated from a library of nucleic acids. Methods for such isolation will be apparent to the ordinary skilled artisan and/or described in Ausubel et al (In: Current Protocols in Molecular Biology. Wiley Interscience, ISBN 047 150338, 1987), Sambrook et al (In: Molecular Cloning: Molecular Cloning: A Laboratory Manual, Cold Spring Harbor Laboratories, New York, Third Edition 2001).

For expressing protein by recombinant means, a protein-encoding nucleotide sequence is placed in operable connection with a promoter or other regulatory sequence capable of regulating expression in a cell-free system or cellular system. For example, nucleic acid comprising a sequence that encodes a peptide in operable connection with a suitable promoter is expressed in a suitable cell for a time and under conditions sufficient for expression to occur. Nucleic acid encoding a peptide is readily derived from the publicly available amino acid sequence.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid (e.g., a transgene), e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid (e.g., a transgene and/or a selectable marker gene and/or a detectable marker gene) to which it is operably linked. Preferred promoters can contain additional copies of one or more specific regulatory elements to further enhance expression and/or alter the spatial expression and/or temporal expression of said nucleic acid.

As used herein, the term "in operable connection with" "in connection with" or "operably linked to" means positioning a promoter relative to a nucleic acid (e.g., a transgene) such that expression of the nucleic acid is controlled by the promoter. For example, a promoter is generally positioned 5' (upstream) to the nucleic acid, the expression of which it controls. To construct heterologous promoter/nucleic acid combinations (e.g., promoter/transgene and/or promoter/selectable marker gene combinations), it is generally preferred to position the promoter at a distance from the gene transcription start site that is approximately the same as the distance between that promoter and the nucleic acid it controls in its natural setting, i.e., the gene from which the promoter is derived. As is known in the art, some variation in this distance can be accommodated without loss of promoter function.

Should it be preferred that a peptide or fusion protein of the invention is expressed in vitro a suitable promoter includes, but is not limited to a T3 or a T7 bacteriophage promoter (Hanes and Plückthun *Proc. Natl. Acad. Sci. USA*, 94 4937-4942 1997).

Typical expression vectors for in vitro expression or cell-free expression have been described and include, but are not limited to the TNT T7 and TNT T3 systems (Promega), the pEXP1-DEST and pEXP2-DEST vectors (Invitrogen).

Typical promoters suitable for expression in bacterial cells include, but are not limited to, the lacz promoter, the lpp promoter, temperature-sensitive λL or λR promoters, T7 promoter, T3 promoter, SP6 promoter or semi-artificial promoters such as the IPTG-inducible tac promoter or lacUV5 promoter. A number of other gene construct systems for expressing the nucleic acid fragment of the invention in bacterial cells are well-known in the art and are described for example, in Ausubel et al (In: Current Protocols in Molecular Biology. Wiley Interscience, ISBN 047 150338, 1987), U.S. Pat. No. 5,763,239 (Diversa Corporation) and Sambrook et al (In: Molecular Cloning: Molecular Cloning: A Laboratory Manual, Cold Spring Harbor Laboratories, New York, Third Edition 2001).

Numerous expression vectors for expression of recombinant polypeptides in bacterial cells and efficient ribosome binding sites have been described, and include, for example, PKC30 (Shimatake and Rosenberg, Nature 292, 128, 1981); pKK173-3 (Amann and Brosius, Gene 40, 183, 1985), pET-3 (Studier and Moffat, J. Mol. Biol. 189, 113, 1986); the pCR vector suite (Invitrogen), pGEM-T Easy vectors (Promega), the pL expression vector suite (Invitrogen) the pBAD/TOPO or pBAD/thio—TOPO series of vectors containing an arabinose-inducible promoter (Invitrogen, Carlsbad, Calif.), the latter of which is designed to also produce fusion proteins with a Trx loop for conformational constraint of the expressed protein; the pFLEX series of expression vectors (Pfizer nc., CT, USA); the pQE series of expression vectors (QIAGEN, CA, USA), or the pL series of expression vectors (Invitrogen), amongst others.

Typical promoters suitable for expression in viruses of eukaryotic cells and eukaryotic cells include the SV40 late promoter, SV40 early promoter and cytomegalovirus (CMV) promoter, CMV IE (cytomegalovirus immediate early) promoter amongst others. Preferred vectors for expression in mammalian cells (e.g., 293, COS, CHO, 10T cells, 293T cells) include, but are not limited to, the pcDNA vector suite supplied by Invitrogen, in particular pcDNA 3.1 myc-His-tag comprising the CMV promoter and encoding a C-terminal 6×His and MYC tag; and the retrovirus vector pSRαtkneo (Muller et al., *Mol. Cell. Biol.*, 11, 1785, 1991).

A wide range of additional host/vector systems suitable for expressing a peptide or fusion protein of the present invention are available publicly, and described, for example, in Sambrook et al (In: Molecular cloning, A laboratory manual, second edition, Cold Spring Harbor Laboratory, Cold Spring Harbor, N.Y., 1989).

Means for introducing the isolated nucleic acid molecule or a gene construct comprising same into a cell for expression are well-known to those skilled in the art. The technique used for a given organism depends on the known successful techniques. Means for introducing recombinant DNA into cells include microinjection, transfection mediated by DEAE-dextran, transfection mediated by liposomes such as by using lipofectamine (Gibco, Md., USA) and/or cellfectin (Gibco, Md., USA), PEG-mediated DNA uptake, electroporation and microparticle bombardment such as by using DNA-coated tungsten or gold particles (Agracetus Inc., WI, USA) amongst others.

Peptide/Analog Isolation

After being produced or synthesized, a peptide compound that is useful in the compositions and methods of the invention may be purified using methods known in the art. Such purification preferably provides a peptide of the invention in a state dissociated from significant or detectable amounts of undesired side reaction products; unattached or unreacted moieties used to modify the peptide compound; and dissociated from other undesirable molecules, including but not limited to other peptides, proteins, nucleic acids, lipids, carbohydrates, and the like.

Standard methods of peptide purification are employed to obtained isolated peptide compounds of the invention, including but not limited to various high-pressure (or performance) liquid chromatography (HPLC) and non-HPLC peptide isolation protocols, such as size exclusion chromatography, ion exchange chromatography, phase separation methods, electrophoretic separations, precipitation methods, salting in/out methods, immunochromatography, and/or other methods.

A preferred method of isolating peptide compounds useful in compositions and methods of the invention employs reversed-phase HPLC using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptide compounds based on their charge. The degree of purity of the peptide compound may be determined by various methods, including identification of a major large peak on HPLC. A peptide compound that produces a single peak that is at least 95% of the input material on an HPLC column is preferred. Even more preferable is a polypeptide that produces a single peak that is at least 97%, at least 98%, at least 99% or even 99.5% of the input material on an HPLC column.

To ensure that a peptide compound obtained using any of the techniques described above is the desired peptide compound for use in compositions and methods of the present invention, analysis of the compound's composition determined by any of a variety of analytical methods known in the art. Such composition analysis may be conducted using high resolution mass spectrometry to determine the molecular weight of the peptide. Alternatively, the amino acid content of a peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide. Since some of the peptide compounds contain amino and/or carboxy terminal capping groups, it may be necessary to remove the capping group or the capped amino acid residue prior to a sequence analysis. Thin-layer chromatographic methods may also be used to authenticate one or more constituent groups or residues of a desired peptide compound. Purity of a peptide compound may also be assessed by electrophoresing the peptide compound in a polyacrylamide gel followed by staining to detect protein components separated in the gel.

Assays to Identify Neuroprotective Compounds

In addition to providing the exemplified neuroprotective peptide inhibitors of AP-1 signaling, the present invention contemplates the identification of homologous peptides and small molecules which may be validated by the approaches disclosed herein.

The identification of such homologs requires the establishment of (i) AP-1 signaling inhibitory activity; and (ii) neuroprotective function as determined by their ability to reduce or inhibit neuronal cell death. Methods for conducting such assays are clearly described herein, in the accompanying examples.

Alternatively, or in addition to any one or more assays described in the accompanying examples, any one or more surrogate assays for determining (i) AP-1 signaling inhibitory activity; and (ii) neuroprotective function of a homologous compound may be employed.

For example, AP-1 signaling inhibitors may be identified by their ability to inhibit the binding of AP-1 to nucleic acid comprising AP-1 binding sites. In one embodiment, an AP-1 bZIP peptide is coated onto a microtitre plate and labelled oligonucleotide (e.g., digoxigenin-labelled oligonucleotide) comprising AP-1 recognition site sequences is added to the microtitre plate in the presence or absence of a test compound. Following washing to remove unbound oligonucleotide, the amount of label bound to the AP-1 peptide is determined. A compound that reduces the level of oligonucleotide bound to the peptide is considered to inhibit AP-1 signaling. Alternatively, or in addition, AP-1 signaling inhibitory compounds are identified by their ability to inhibit protein interactions in the AP-1 signaling cascade, other than merely c-Jun dimerization. For example, a reverse hybrid assay can be employed to rescue cells in which a test compound inhibits or reduces an interaction between any of the following proteins: Cdc42 and Rac1, cdc42 and MLK3, Rac1 and MLK3, JNK and c-Jun, a MAP kinase kinase kinase and JNK, JNK and JIP, or any of the proteins that interact to form AP-1 e.g., ATF-2 or c-Fos. Reverse hybrid methods will be apparent to the skilled artisan and/or described in Watt et al. (U.S. Ser. No. 09/227,652) or Erickson et al. (WO95/26400).

Homologs of the neuroprotective peptides described herein, including those that have been demonstrated to possess AP-1 signaling inhibitory activity by one or more primary surrogate assays supra or by a method described in the accompanying examples, may be determined by their ability to inhibit neuronal cell death e.g., apoptosis and/or necrosis. For example, APOPTEST (available from Immunotech) stains cells early in apoptosis, and does not require fixation of the cell sample (Martin et al., 1994). This method utilizes an annexin V antibody to detect cell membrane re-configuration that is characteristic of cells undergoing apoptosis. Apoptotic cells stained in this manner can then sorted either by fluorescence activated cell sorting (FACS), ELISA or by adhesion and panning using immobilized annexin V antibodies.

Alternatively, a terminal deoxynucleotidyl transferase-mediated biotinylated UTP nick end-labeling (TUNEL) assay is used to determine the level of cell death. The TUNEL assay uses the enzyme terminal deoxynucleotidyl transferase to label 3'-OH DNA ends, generated during apoptosis, with biotinylated nucleotides. The biotinylated nucleotides are then detected by using streptavidin conjugated to a detectable marker. Kits for TUNEL staining are available from, for example, Intergen Company, Purchase, N.Y.

Alternatively, or in addition, an activated caspase, such as, for example, Caspase 3 is detected. Several caspases are effectors of apoptosis and, as a consequence, are only activated to significant levels in a cell undergoing programmed cell death. Kits for detection of an activated caspase are available from, for example, Promega Corporation, Madison Wis., USA. Such assays are useful for both immunocytochemical or flow cytometric analysis of cell death.

Methods for detecting necrosis or determining the level of necrosis, e.g., in a sample comprising cells are known in the art and/or described, for example, in Lemaire et al., *Cell Death and Differentiation*, 6: 813-820, 1999, Therapeutic Compositions As will be apparent to the skilled artisan, peptides identified in the method of the present invention are useful as a therapeutic and/or prophylactic treatment of a neuronal disease and/or disorder, preferably those disorders associated with elevated extracellular glutamate leading to glutamate excitotoxicity and/or NMDA excitotoxicity e.g., migraine, stroke, traumatic brain injury, epilepsy and neurodegenerative disorders including Parkinson's Disease (PD), Alzheimer's Disease (AD) and Amyotrophic Lateral Sclerosis (ALS).

Accordingly, the present invention provides a method for preventing or delaying neuronal cell death in a subject comprising administering an AP-1 signaling inhibitory peptide of the invention according to any embodiment described herein or a composition comprising said peptide to a subject in need of treatment e.g., a subject suffering from the disease and/or disorder or at risk of developing and/or suffering from the disease and/or disorder.

Clearly the present invention encompasses the use of an AP-1 signaling inhibitory peptide of the invention according to any embodiment described herein or a derivative or analog thereof in medicine. Additionally, the present invention encompasses a peptide identified by the present invention when used in medicine.

As will be apparent to the skilled artisan, the use of an AP-1 signaling inhibitory peptide of the invention according to any embodiment described herein may require the peptide or analog be formulated into a composition for administration. Preferably, the composition is a pharmaceutical composition.

To prepare pharmaceutical or sterile compositions including a peptide, peptide analog, peptide derivative or nucleic acid encoding the peptide, is mixed with a pharmaceutically acceptable carrier or excipient. Compositions comprising a therapeutic peptide or nucleic acid are prepared, for example, by mixing with physiologically acceptable carriers, excipients, or stabilizers in the form of, e.g., lyophilized powders, slurries, aqueous solutions, lotions, or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

Formulation of a pharmaceutical compound will vary according to the route of administration selected (e.g., solution, emulsion, capsule). For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, Remington's Pharmaceutical Sciences, 17th Edition, Mack Publishing Co., Pa., 1985). For inhalation, the agent can be solubilized and loaded into a suitable dispenser for administration (e.g., an atomizer, nebulizer or pressurized aerosol dispenser).

Furthermore, where the active compound is a peptidyl compound, it can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into, a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

Selecting an administration regimen for a therapeutic composition depends on several factors, including the serum or tissue turnover rate of the entity, the level of symptoms, the immunogenicity of the entity, and the accessibility of the target cells in the biological matrix. Preferably, an administration regimen maximizes the amount of therapeutic compound delivered to the patient consistent with an acceptable level of side effects. Accordingly, the amount of composition delivered depends in part on the particular entity and the severity of the condition being treated. Guidance in selecting appropriate doses of peptides are available (see, e.g., Milgrom, et al. *New Engl. J. Med.* 341:1966-1973, 1999; Slamon, et al. *New Engl. J. Med.* 344:783-792, 2001; Beniaminovitz, et al. *New Engl. J. Med.* 342:613-619, 2000; Ghosh, et al. *New Engl. J. Med.* 348:24-32, 2003; or Lipsky, et al. *New Engl. J. Med.* 343:1594-1602, 2000).

A peptide is provided, for example, by continuous infusion, or by doses at intervals of, e.g., one day, one week, or 1-7 times per week. Doses of a composition may be provided intravenously, subcutaneously, topically, orally, nasally, rectally, intramuscularly, intracerebrally, or by inhalation. A preferred dose protocol is one involving the maximal dose or dose frequency that avoids significant undesirable side effects. A total weekly dose depends on the type and activity of the compound being used. For example, such a dose is at least about 0.05 µg/kg body weight, or at least about 0.2 µg/kg, or at least about 0.5 µg/kg, or at least about 1 µg/kg, or at least about 10 µg/kg, or at least about 100 µg/kg, or at least about 0.2 mg/kg, or at least about 1.0 mg/kg, or at least about 2.0 mg/kg, or at least about 10 mg/kg, or at least about 25 mg/kg, or at least about 50 mg/kg (see, e.g., Yang, et al. *New Engl. J. Med.* 349:427-434, 2003; or Herold, et al. *New Engl. J. Med.* 346:1692-1698, 2002.

An effective amount of a peptide for a particular patient may vary depending on factors such as the condition being treated, the overall health of the patient, the method route and dose of administration and the severity of side affects, see, e.g., Maynard, et al. (1996) A Handbook of SOPs for Good Clinical Practice, Interpharm Press, Boca Raton, Fla.; or Dent (2001) Good Laboratory and Good Clinical Practice, Urch Publ., London, UK.

Determination of the appropriate dose is made by a clinician, e.g., using parameters or factors known or suspected in the art to affect treatment or predicted to affect treatment. Generally, the dose begins with an amount somewhat less than the optimum dose and is increased by small increments thereafter until the desired or optimum effect is achieved relative to any negative side effects. Important diagnostic measures include those of symptoms of the disease and/or disorder being treated. Preferably, a compound that will be used is derived from or adapted for use in the same species as the subject targeted for treatment, thereby minimizing a humoral response to the reagent.

An effective amount of therapeutic will decrease disease symptoms, for example, as described supra, typically by at least about 10%; usually by at least about 20%; preferably at least about 30%; more preferably at least about 40%, and more preferably by at least about 50%.

The route of administration is preferably by, e.g., topical or cutaneous application to an open wound, or alternatively, by injection by intravenous, intraperitoneal, intracerebral, intramuscular, intraocular, intra-arterial, intracerebrospinal, intralesional, intrathecal, intra-arterial or pulmonary routes, or by local administration following a craniotomy or by sustained release or implant (see, e.g., Sidman et al. *Biopolymers* 22:547-556, 1983; Langer, et al. *J. Biomed. Mater. Res.* 15:167-277, 1981; Langer *Chem. Tech.* 12:98-105, 1982; Epstein, et al. *Proc. Natl. Acad. Sci. USA* 82:3688-3692, 1985; Hwang, et al. *Proc. Natl. Acad. Sci. USA* 77:4030-4034, 1980; U.S. Pat. Nos. 6,350,466 and 6,316,024).

Formulations suitable for intracerebral, intrathecal, intra-arterial or intracerebrospinal injection or other injection directly to the central nervous system are particularly preferred, especially for conditions such as brain trauma or cerebral injuries caused by wounding e.g., motor vehicle accident etc. Formulations suitable for local administration following a craniotomy are also particularly preferred.

Preferred routes of administration of a neuroprotective peptide of the invention are, for example:
(i) intravenously, for example, in a 0.9% saline solution;
(ii) intrathecally, for example, the peptide composition is given after a lumbar puncture with a 18 G needle or after subsequent insertion of a extralumbal catheter with the tip in the intrathecal space;
(iii) by selective intra-arterial digital subtraction angiography, for example, wherein a microcatheter is inserted in the femoral artery and guided to the cerebral arteries and the peptide of the invention perfused into the area;
(iv) locally after craniotomy;
(v) by intracoronary delivery using catheter-based deliveries of synthesized peptide suspended in a suitable buffer e.g., such as saline which is injected locally into the coronary artery e.g., by injecting into the myocardium through the vessel wall, using a suitable local delivery catheter such as a 10 mm InfusaSleeve catheter (Local Med, Palo Alto, Calif.) loaded over a 3.0 mm×20 mm angioplasty balloon, delivered over a 0.014 inch angioplasty guide wire;
(vi) by intracoronary bolus infusion of peptide (or derivative) wherein the peptide is manually injected, for example, through an Ultrafuse-X dual lumen catheter (SciMed, Minneapolis, Minn.) or another suitable device into proximal orifices of coronary arteries;
(vii) by intramyocardial delivery of synthesized peptide or analog e.g., under direct vision following thoracotomy or using thoracoscope or via a catheter; or
(viii) by application in a formulation comprising Gelfoam administered to a lesion e.g., in brain tissue.

Pericardial delivery of synthesized peptide or analog is typically accomplished by installation of the peptide-containing solution into the pericardial sac. The pericardium is accessed via a right atrial puncture, transthoracic puncture or via a direct surgical approach. Once the access is established, the peptide or analog is infused into the pericardial cavity and the catheter is withdrawn. Alternatively, the delivery is accomplished via the aid of slow-release polymers such as heparinal-alginate or ethylene vinyl acetate (EVAc). In both cases, once the peptide or analog is integrated into the polymer, the desired amount of peptide/polymer is inserted under the epicardial fat or secured to the myocardial surface using, for example, sutures. In addition, the peptide/polymer composition can be positioned along the adventitial surface of coronary vessels.

For administration of a peptide by a route that does not directly access the central nervous system, the peptide may have to cross the blood brain barrier. Methods and means for enabling a peptide to cross the blood brain barrier are known in the art and/or described, for example, in USSN20050142141. For example, a peptide of the invention is conjugated to an agent that enables the peptide to cross the blood brain barrier (e.g., a Trojan horse). E.g., HIR MAb 83-14 is a murine MAb that binds to the human insulin receptor (HIR). This binding triggers transport across the BBB of MAb 83-14 (Pardridge et al, *Pharm., Res.* 12: 807-816, 1995), and any drug or gene payload attached to the MAb (Wu et al., *J. Clin. Invest.*, 100: 1804-1812, 1997).

The use of molecular Trojan horses to ferry drugs or genes across the blood brain barrier is described in U.S. Pat. Nos. 4,801,575 and 6,372,250. The linking of drugs to MAb transport vectors is facilitated with use of avidin-biotin technology. In this approach, the drug or protein therapeutic is monobiotinylated and bound to a conjugate of the antibody vector and avidin or streptavidin. The use of avidin-biotin technology to facilitate linking of drugs to antibody-based transport vectors is described in U.S. Pat. No. 6,287,792. Fusion proteins have also been used where a drug is genetically fused to the MAb transport vector.

In a preferred embodiment, a therapeutic peptide described herein is administered to a subject when the subject is suffering from or has recently suffered from an ischemic event (e.g., a stroke) or nerve trauma or trauma to the central nervous system. Such timing of administration is useful for, for example, reducing the effect of reperfusion following an ischemic event. The peptide may also be administered to a subject when the subject is at risk of experiencing a reperfusion injury following an ischemic event.

The present invention is further described with reference to the following non-limiting examples.

EXAMPLE 1

Isolation of AP-1 Complex Formation Inhibitory Phylomer™ Peptides

Phylomer™ Peptide Library Construction

Genomic DNA from 15 different sequenced bacterial genomes (*Aquifex aeolicus, Bacillus subtilis, Bordetella pertussis, Borrelia burgdorferi, Chlamydia trachomatis, Escherichia coli* K12, *Haemophilus influenzae, Helicobacter pylori, Methanobacterium thermoautotrophicu, Methanococcus jannashii, Neisseria meningitides, Pyrococcus horikoshi, Pseudomonas aeruginosa, Synechocystis* PCC 6803, *Thermoplasma volcanicum*) was obtained. This DNA was used as the template for random amplification using random primers containing a FLAG-tag, designated BGFN6 and BGFN9, as follows:

```
BGFN6:
5'-GACTACAAGGACGACGACGACAAGGCTTATCAATCAATCANNNNNNN-3';

BGFN9:
5'-GACTACAAGGACGACGACGACAAGGCTTATCAATCAATCANNNNNNNNN-3'
```

The following protocol was employed:
Amplification Round 1: 3.33 µM Klenow primer, 1× Klenow buffer, 200 µM dNTPs, Klenow, PEG (8500) in total volume of 30 µl. Mix primer, DNA, and water; boil for 3-min, snap cool on ice and then transfer to tube containing the other reagents. Incubate 15° C. for 30 mins, RT for 2 hours, then 37° C. for 15 min.
Amplification Round 2: Boil tube 5 min, snap cool, add 0.5 µl Klenow enzyme and then incubate as in step 2.
Amplification Round 3: Boil tube 5 min, snap cool, add: 4 µl BGF-F9 primer (25 µM), 1 µl 10× buffer, 3 µl dNTPs (2 mM), 0.5 µl Klenow, 1.5 µl water. Incubate 15° C. for 30 min, RT for 2 hours, 37° C. for 15 min.
Amplification Round 4: Boil tube 5 min, snap cool, add 0.5 µl Klenow enzyme and then incubate as in Round 3 and products purified using Amplicon spin columns.

Cloning sites were added by conventional PCR primed from the tag sequence with the following primers:

```
BGF-F5:
5'-GAGAGgaattcAGGTCAGACTACAAGGACGACGACGACAAG-3';

BGF-R6-Acc651:
5'-GAGAGggtaccAGGTCAGACTACAAGGACGACGACGACAAG-3'.
```

The amplified sequences were digested with EcoRI/Acc651, and cloned into the vector pYTB3, a TRP1 expressing, 2-micron origin vector allowing constitutive expression of inserts from the ADH1 promoter. About $5 \times 10^6$ colony forming units (CFUs) were formed from the primary transformation and harvested from the plates. DNA was prepared from harvested cells using standard procedures.

Reverse-2-Hybrid Screening

The yeast two hybrid system described by Vidal.M., In: *The Yeast Two Hybrid System* (eds. P. Bartel and S. Fields), Oxford University Press, New York (1997), was modified to add another counter selectable marker (CYH2) and to allow flexible titration of stringency by adjustment of sugar concentrations in the screening media.

As an example to demonstrate the ability of peptides to inhibit AP-1 complex formation, inhibition of c-Jun dimerization was tested. Partial fragments of c-Jun i.e., JunZ (774-927 bp) and Jun1 (558-1002 bp), were cloned into yeast two-hybrid vectors pDD (a kanamycin-resistant variant of pGilda bait vector) and pJFK (pYesTrp prey vector (Invitrogen) modified by replacing the TRP1 yeast selection gene with HIS5), respectively, before co-transforming into *Saccharomyces cerevisiae* strain PRT480 (MATα, his3, trp1, ura3, 4 LexA-LEU2, lys2::3 cIop-LYS2, $CAN^R$, $CYH2^R$, ade2::2 LexA-CYH2-ZEO, his5::2 LexA-URA3-G418) using a standard lithium-acetate based chemical transformation protocol.

The Phylomer™ peptide library was transformed into *S. cerevisiae* strain PRT51 (MATα, his3, trp1, ura3, 6 LexA-LEU2, lys2::3 cIop-LYS2, $CYH2^R$, ade2::G418-pZero-ade2, met15::Zeo-pBLUE-met15, his5::hygro), using a high-efficiency lithium acetate-based chemical transformation protocol, slightly modified to maximize the number of transformants.

Bait/prey plasmid containing PRT480 haploids ($10^8$ cells) were mated with the Phylomer™ library ($10^7$ c.f.u.) according to a liquid mating protocol for pretransformed libraries (Clontech, USA), and plated to HW⁻ minimal media (minimal media lacking histidine and tryptophan) to select for diploids. These plates were scraped after 2 days incubation at 30° C., and the cells were washed, resuspended 1:1 (v/v) in yeast freezing solution (65% v/v glycerol, 0.1M $MgSO_4$, 25 mM Tris-Cl pH 8.0), and frozen at −80° C. in 1 ml aliquots.

To select peptides that block formation of an AP-1 complex requiring the interaction between JUN1 and JunZ, about $1.5 \times 10^7$ c.f.u Jun/Phylomer™ diploids were thawed and outgrown overnight in HW⁻ to achieve log-phase growth. The following day, 4×10⁷ cells were plated onto counter-selective media: HWU⁻ (lacking histidine, tryptophan and uracil), containing supplements of 0.02% galactose (gal), 2% raffinose (raff), 0.2 µg/ml uracil, 0.06% (w/v) 5-Fluoroorotic acid (FOA), 5 µg/ml cycloheximide. These plates were incubated for 7 days, then colonies were picked to HWU⁻ 0.02% gal, 2% raff, and then to HWL⁻ (lacking histidine, tryptophan and leucine) 0.02% gal, 2% raff to confirm blocking phenotype.

From an initial reverse-two-hybrid screen of approximately 300,000 clones expressed from a third vector (pYTB3), 95 primary transformants were identified that allowed yeast survival on media for counter-selection against an AP-1 complex formation viz. c-Jun dimerization. These included transformants comprising the clones designated PYC19 [DNA sequence set forth in SEQ ID NO: 26; encoded amino acid sequence set forth in SEQ ID NO: 27 (with FLAG epitope) and 28 (without FLAG epitope)]; PYC35 [DNA sequence set forth in SEQ ID NO: 34; encoded amino acid sequence set forth in SEQ ID NO: 35 (with FLAG epitope) and 36 (without FLAG epitope)]; PYC36 [DNA sequence set forth in SEQ ID NO: 43; encoded amino acid sequence set forth in SEQ ID NO: 44 (with FLAG epitope) and 45 (without FLAG epitope)]; PYC38/39 [DNA sequence set forth in SEQ ID NO: 52; encoded amino acid sequence set forth in SEQ ID NO: 53 (with FLAG epitope) and 54 (without FLAG epitope)]; and PYC41 [DNA sequence set forth in SEQ ID NO: 60; encoded amino acid sequence set forth in SEQ ID NO: 61 (with FLAG epitope) and 62 (without FLAG epitope)].

Subsequently, the individual plasmid clones were rescued from the yeast and re-transformed to confirm the disruption phenotype; 63% of the primary "hits", including PYC 19, PYC35, PYC26, PYC38/39 and PYC41, were positive in two assays for recapitulation of the phenotype.

EXAMPLE 2

Phylomer™ Peptides that Decrease AP-1 Controlled Reporter Gene Expression

Phylomer™ peptides that inhibit an AP-1 complex formation as described in Example 1 were tested for their ability to decrease AP-1 controlled reporter expression (since Jun dimers are AP-1 moieties). A transient transfection assay in which the expression of each clone was plasmid driven was employed, thereby avoiding the synthesis of large numbers of peptides.

Luciferase Reporter Gene Assay of AP-1 Dependent Transcriptional Activity

The K562 cell line was stably-transfected with the AP-1 luciferase reporter (AP1-Luc) of the Mercury Pathway Profiling kit (Clontech, U.S.A.), and the clonal cell line K562/AP1-Luc was established. In 6-well tissue culture plate format, K562/AP1-Luc cells were transfected with either pcDNA3 control, pcDNA3-JunDN (a dominant negative mutant of c-Jun), or pcDNA3-peptide, using Lipofectamine2000 (Life Technologies) according to manufacturer's instructions. Transfection reactions were incubated for 48 hours, cells collected and protein lysates extracted for luciferase assay according to Mercury Pathway Profiling kit and associated protocols.

Luciferase assays were performed in independent triplicates, and results for each peptide subjected to statistical analysis (SPSS software package) to determine if they were different to JunDN (positive control for AP-1 inhibition) or pcDNA-3 (negative control for AP-1 inhibition).

All AP-1 luciferase values were normalised to the renilla expression from a cotransfection control. Under these experimental conditions, approximately 30% of Phylomer™ peptides decreased AP-1 reporter activity by at least 50% when compared to the vector-only control (i.e., pcDNA3 vector). More particularly, the peptides designated PYC35, PYC36, PYC38/39 and PYC41 reduced AP-1 reporter activity to approximately 35%, 44%, 47% and 48%, respectively of the level observed for the control sample. These data demonstrate that the hit-rate from the c-Jun screen for functional blockers of AP-1 activity was high i.e., exceeding 1:13,000, suggesting that Phylomer™ peptide libraries provide a rich source of AP-1 inhibitors.

EXAMPLE 3

Peptides that Inhibit AP-1 Signaling are Neuroprotective Following Glutamate Excitotoxicity in Primary Cortical Neuronal Cultures Materials & Methods
1. Peptides Peptides used in this example comprise the amino acid sequences shown in the accompanying Sequence Listing. The peptides were designated as shown in Table 1.

TABLE 1

| Peptide Name | Description | Sequence | SEQ ID NO. |
|---|---|---|---|
| PYC19L | Phylomer™ core sequence | Leu Ile Asn Gln Ser Tyr Ala Tyr Pro Tyr Ile Tyr | SEQ ID NO: 28 |
| PYC19D | Retroinverted form of PYC19L[a] | Tyr Ile Tyr Pro Tyr Ala Tyr Ser Gln Asn Ile Leu Gly | SEQ ID NO: 29 |
| PYC19L-TAT | PYC19L with an N-terminal TAT | Gly Arg Lys Lys Arg Arg Gln Arg Arg Gly Leu Ile Asn Gln Ser Tyr Ala Tyr Pro Tyr Ile Tyr | SEQ ID NO: 30 |
| PYC19D-TAT | Retroinverted PYC19L-TAT[b] | Tyr Ile Tyr Pro Tyr Ala Tyr Ser Gln Asn Ile Leu Gly Arg Arg Arg Gln Arg Arg Lys Lys Arg Gly | SEQ ID NO: 31 |
| PYC19L-FM | PYC19L with C-terminal Kaposi FGF protein transduction domain | Leu Ile Asn Gln Ser Tyr Ala Tyr Pro Tyr Ile Tyr Gly Ala Ala Val Leu Leu Pro Val Leu Leu Ala Ala Pro | SEQ ID NO: 32 |
| PYC19D-FM | Retroinverted form of PYC19L-FM[b] | Pro Ala Ala Leu Leu Val Pro Leu Leu Val Ala Ala Gly Tyr Ile Tyr Pro Tyr Ala Tyr Ser Gln Asn Ile Leu | SEQ ID NO: 33 |

TABLE 1-continued

| Peptide Name | Description | Sequence | SEQ ID NO. |
|---|---|---|---|
| PYC35L | Phylomer™ core sequence | Ala Tyr Gln Ser Ile Arg Ser Gly Gly Ile Glu Ser Ser Ser Lys Arg Glu Arg | SEQ ID NO: 36 |
| PYC35D | Retroinverted form of PYC35L[a] | Arg Glu Arg Lys Ser Ser Ser Glu Ile Gly Gly Ser Arg Ile Ser Gln Tyr Ala Gly | SEQ ID NO: 37 |
| PYC35L-TAT | PYC35L with an N-terminal TAT | Gly Arg Lys Lys Arg Arg Gln Arg Arg Gly Ala Tyr Gln Ser Ile Arg Ser Gly Gly Ile Glu Ser Ser Ser Lys Arg Glu Arg | SEQ ID NO: 38 |
| PYC35D-TAT | retroinverted form of PYC35L-TAT[b] | Arg Glu Arg Lys Ser Ser Ser Glu Ile Gly Gly Ser Arg Ile Ser Gln Tyr Ala Gly Arg Arg Arg Gln Arg Arg Lys Lys Arg Gly | SEQ ID NO: 39 |
| PYC35L-FM | PYC35L with C-terminal Kaposi FGF protein transduction domain | Ala Tyr Gln Ser Ile Arg Ser Gly Gly Ile Glu Ser Ser Ser Lys Arg Glu Arg Gly Ala Ala Val Leu Leu Pro Val Leu Leu Ala Ala Pro | SEQ ID NO: 40 |
| PYC35D-FM | retroinverted form of PYC35L-FM[b] | Pro Ala Ala Leu Leu Val Pro Leu Leu Val Ala Ala Gly Arg Glu Arg Lys Ser Ser Ser Glu Ile Gly Gly Ser Arg Ile Ser Gln Tyr Ala | SEQ ID NO: 41 |
| PYC35DScram-TAT | retroinverted peptide comprising scrambled PYC35D peptide and retroinverted TAT[b] | Lys Ile Glu Arg Ser Glu Gly Ile Ser Gln Ser Ala Arg Ser Arg Gly Tyr Ser Gly Arg Arg Arg Gln Arg Arg Lys Lys Arg Gly | SEQ ID NO: 42 |
| PYC36L | Phylomer™ core sequence | Gly Leu Gln Gly Arg Arg Arg Gln Gly Tyr Gln Ser Ile Lys Pro | SEQ ID NO: 45 |
| PYC36D | retroinverted form of PYC36L[b] | Pro Lys Ile Ser Gln Tyr Gly Gln Arg Arg Arg Gly Gln Leu Gly | SEQ ID NO: 46 |
| PYC36L-TAT | PYC36L with an N-terminal TAT | Gly Arg Lys Lys Arg Arg Gln Arg Arg Gly Gly Leu Gln Gly Arg Arg Arg Gln Gly Tyr Gln Ser Ile Lys Pro | SEQ ID NO: 47 |
| PYC36D-TAT | retroinverted form of PYC36L-TAT[b] | Pro Lys Ile Ser Gln Tyr Gly Gln Arg Arg Arg Gly Gln Leu Gly Gly Arg Arg Gln Arg Arg Lys Lys Arg Gly | SEQ ID NO: 48 |
| PYC36L-FM | PYC36L with C-terminal Kaposi FGF protein transduction domain) | Gly Leu Gln Gly Arg Arg Arg Gln Gly Tyr Gln Ser Ile Lys Pro Gly Ala Ala Val Leu Leu Pro Val Leu Leu Ala Ala Pro | SEQ ID NO: 49 |
| PYC36D-FM | retroinverted form of PYC36L-FM[b] | Pro Ala Ala Leu Leu Val Pro Leu Leu Vat Ala Ala Gly Pro Lys Ile Ser Gln Tyr Gly Gln Arg Arg Arg Gly Gln Leu Gly | SEQ ID NO: 50 |
| PYC36D Scram-TAT | retroinverted peptide comprising scrambled PYC36D peptide and retroinverted TAT protein transduction domain[b] | Lys Arg Arg Gly Gly Ile Leu Arg Tyr Gly Gln Pro Gln Ser Gln Gly Arg Arg Gln Arg Arg Lys Lys Arg Gly | SEQ ID NO: 51 |
| PYC38/39L | Phylomer™ core sequence | Gly Leu Gln Gly Arg Arg Gln Pro Gly Gln Gln Pro Gln Gly Arg Trp Ser Gly Arg Ala Leu Pro Ala His Arg | SEQ ID NO: 54 |
| PYC38/39D | retroinverted form of PYC38/38L[b] | Arg His Ala Pro Leu Ala Arg Gly Ser Trp Arg Gly Gln Pro Gln Gln Gly Pro Gln Arg Arg Gln Leu Gly | SEQ ID NO: 55 |
| PYC38/39L-TAT | PYC38/39L with N-terminal TAT | Gly Arg Lys Lys Arg Arg Gln Arg Arg Gly Gly Leu Gln Gly Arg Arg Gln Pro Gly Gln Gln Pro Gln Gly Arg Trp Ser Gly Arg Ala Leu Pro Ala His Arg | SEQ ID NO: 56 |
| PYC38/39D-TAT | retroinverted PYC38/39L-TAT[b] | Arg His Ala Pro Leu Ala Arg Gly Ser Trp Arg Gly Gln Pro Gln Gln Gly Pro Gln Arg Arg Gln Leu Gly Gly Arg Arg Arg Gln Arg Arg Lys Lys Arg Gly | SEQ ID NO: 57 |
| PYC38/39L-FM | PYC38/39L with C-terminal Kaposi FGF protein transduction domain | Gly Leu Gln Gly Arg Arg Gln Pro Gly Gln Gln Pro Gln Gly Arg Trp Ser Gly Arg Ala Leu Pro Ala His Arg Ala Ala Val Leu Leu Pro Val Leu Leu Ala Ala Pro | SEQ ID NO: 58 |
| PYC38/39D-FM | retroinverted PYC38/39L-FM[b] | Pro Ala Ala Leu Leu Val Pro Leu Leu Val Ala Ala Gly Arg His Ala Pro Leu Ala Arg Gly Ser Trp Arg Gly Gln Pro Gln Gln Gly Pro Gln Arg Arg Gly Gln Leu Gly | SEQ ID NO: 59 |

TABLE 1-continued

| Peptide Name | Description | Sequence | SEQ ID NO. |
|---|---|---|---|
| PYC41L | Phylomer™ core sequence | Val Ser Ile Asn Gln Glu His His Arg Leu Leu Pro Leu | SEQ ID NO: 62 |
| PYC41D | retroinverted PYC41L[b] | Leu Pro Leu Leu Arg His His Glu Gln Asn Ile Ser Val Gly | SEQ ID NO: 63 |
| PYC41L-TAT | PYC41L with N-terminal TAT | Gly Arg Lys Lys Arg Arg Gln Arg Arg Arg Gly Val Ser Ile Asn Gln Glu His His Arg Leu Leu Pro Leu | SEQ ID NO: 64 |
| PYC41D-TAT | retroinverted PYC41L-TAT[b] | Leu Pro Leu Leu Arg His His Glu Gln Asn Ile Ser Val Gly Arg Arg Arg Gln Arg Arg Lys Lys Arg Gly | SEQ ID NO: 65 |
| PYC41L-FM | PYC41 with C-terminal Kaposi FGF protein transduction domain | Val Ser Ile Asn Gln Glu His His Arg Leu Leu Pro Leu Gly Ala Ala Val Leu Leu Pro Val Leu Leu Ala Ala Pro | SEQ ID NO: 66 |
| PYC41D-FM | retroinverted PYC41L-FM[b] | Pro Ala Ala Leu Leu Val Pro Leu Leu Val Ala Ala Gly Leu Pro Leu Leu Arg His His Glu Gln Asn Ile Ser Val | SEQ ID NO: 67 |
| JNK1-1D-TAT | retroinverted JNK1-1-TAT | Thr Asp Gln Ser Arg Pro Val Gln Pro Phe Leu Asn Leu Thr Thr Pro Arg Lys Pro Arg Pro Arg Arg Gln Arg Arg Lys Lys Arg Gly | SEQ ID NO: 68 |

[a]all amino acids other than glycine are D-amino acids with a C-terminal glycine linker added
[b]all amino acids other than glycine are D-amino acids All peptides are synthesized using standard procedures and HPLC-purified, e.g., by Mimotopes Pty Ltd (Australia), or GenScript Corporation (USA), or Auspep (Australia). All peptides were prepared as 100× stocks (500 μM) in normal saline.

The peptide JNKI-1 D-TAT served as a positive control. Peptides PYC35D Scram-TAT and PYC36D Scram-TAT served as negative controls, and to determine whether or not the integrity of the retroinverted Phylomer™ peptide sequence was necessary for to proficiency in attenuating neuronal cell death.

2. Primary Cortical Neuronal Cultures

Cortical neuronal cultures were established as described by Meloni et al., *Neuroscience* 108, 17-26, 2001. Briefly, cortical tissue from E18-E19 Sprague-Dawley rats was dissociated in Dulbelcco's Modified Eagle Medium (DMEM; Invitrogen, Australia) supplemented with 1.3 mM L-cysteine, 0.9 mM NaHCO$_3$, 10 units/ml papain (Sigma, USA) and 50 units/ml DNase (Sigma) and washed in cold DMEM/10% (v/v) horse serum. Neurons were resuspended in Neurobasal (NB; Invitrogen) containing 2% B27 supplement (B27; Invitrogen). Before seeding, culture vessels comprising either a 96-well plastic plate or 24-well plastic plate with 13 mm glass coverslips (ProSciTech, Australia), were coated with poly-D-lysine (50 μg/mL; 70-150K; Sigma) and incubated overnight at room temperature. The poly-D-lysine was removed and replaced with NB (containing 2% B27; 4% fetal bovine serum; 1% horse serum; 62.5 μM glutamate; 25 μM 2-mercaptoethanol; and 30 μg/mL streptomycin and 30 μg/mL penicillin). Neurons were plated to obtain approximately 10,000 viable neurons for each well of a 96-well plate, or 200,000 viable neurons per well of a 24-well plate, on day in vitro (DIV) 9. Neuronal cultures were maintained in a CO$_2$ incubator (5% CO$_2$, 95% air balance, 98% humidity) at 37° C. On DIV 4, one third of the culture medium was removed and replaced with fresh NB/2% B27 containing the mitotic inhibitor, cytosine arabinofuranoside (Sigma) at 1 μM concentration. On DIV 8, one half of the culture medium was replaced with NB/2% B27. Cultures were used on DIV 11 or 12, and consisted of >95% neurons.

3. Glutamate Excitotoxicity

To induce glutamate excitotoxicity in the cortical neuronal cultures (96-well plate format), 50 μl of conditioned media containing 200 μM glutamate was added to culture wells containing 50 μl conditioned media (100 μM final glutamate concentration). Cultures were incubated at 37° C. in a CO$_2$ incubator for 5 minutes, after which time the media was replaced with 100 μl of 50% NB/2% N$_2$ and 50% balance salt solution (NB/N2:BSS).

To determine the efficacy of a peptide in preventing or delaying glutamate excitotoxicity, peptides were added to wells at a suitable time prior to incubation of neurons in the presence of glutamate, e.g., about 15 minutes prior to incubation in glutamate or post-glutamate exposure.

For determining the time course over which any peptide was effective, peptides were added either prior to or post-glutamate exposure.

To determine calcium influx, peptides were added both prior to and post-glutamate exposure.

A non-peptide positive control, consisting of 5 μM concentration of the glutamate receptor inhibitors MK801/5 μM 6-cyano-7-nitroquinoxaline (MK801/CNQX), was used in a similar manner to peptides, either prior to or post-glutamate exposure.

Untreated and glutamate-treated control samples received media additions with and without glutamate respectively.

4. Neuronal Viability and Statistical Analysis

Eighteen hours after glutamate exposure, neuronal cultures were examined by light microscopy for qualitative assessment of neuronal damage. Neuronal viability was quantitatively measured by 3-(4,5,dimethyliazol-2-yl)-5-(3-carboxymethoxy-phenyl)-2-(4-sulfophenyl)-2H-tetrazolium salt (MTS) assay (Promega, Australia). The MTS assay measures the mitochondrial conversion of the tetrazolium salt to a water-soluble brown formazan salt, which is detected spectrophotometrically at 495 nm. MTS absorbance data was converted to reflect proportional cell viability relative to both the untreated and glutamate treated controls. Viability data was analysed by ANOVA, followed by post-hoc Fischer's PLSD test, with $p<0.05\%$ values considered statistically significant. All assays were performed with quadruplicate sister neuronal cultures repeated a minimum of four times independently.

5. Neuronal Intracellular Calcium Levels Following Glutamate Exposure

Cortical cultures (24-well plate) were loaded with the Ca2+ indicator dye Fura-2-AM (1 µM) in 300 µl NB/N2:BSS, 0.3% pluronic F-127, for 45 minutes at 37° C. The loading media was then exchanged for 300 µl of fresh NB/N2:BSS containing 5 µM peptide or MK801/CNQX and incubated for 20 minutes at 37° C. Control cultures received 300 µl of NB/N2:BSS only. Coverslips were transferred to a microscope recording chamber of the microscope in 900 µl physiological rat saline (PRS) only, or containing peptide (5 µM) or MK801/CNQX and incubated for a further 10 minutes at room temperature. A diaphragm device located on the microscope optically isolated a group of five to seven neurons for each measurement. Intracellular Ca2+ levels were recorded for 30 seconds before the addition of 100 µl of 1 mM glutamate (100 µM final concentration), and for a further 210 seconds after the addition. Measurements of Ca2+ were performed using an inverted epifluorescence microscope (Nikon TE2000, Japan) connected to a spectrophotometer (Cairn, UK). The ratio (R) of fluorescence emission (emission wavelength: 510 nm) at 340- and 380-nm excitation (F340/F380), was collected at 10 Hz, stored and analyzed using the Cairn software package (Cairn).

Results

Figure 1:
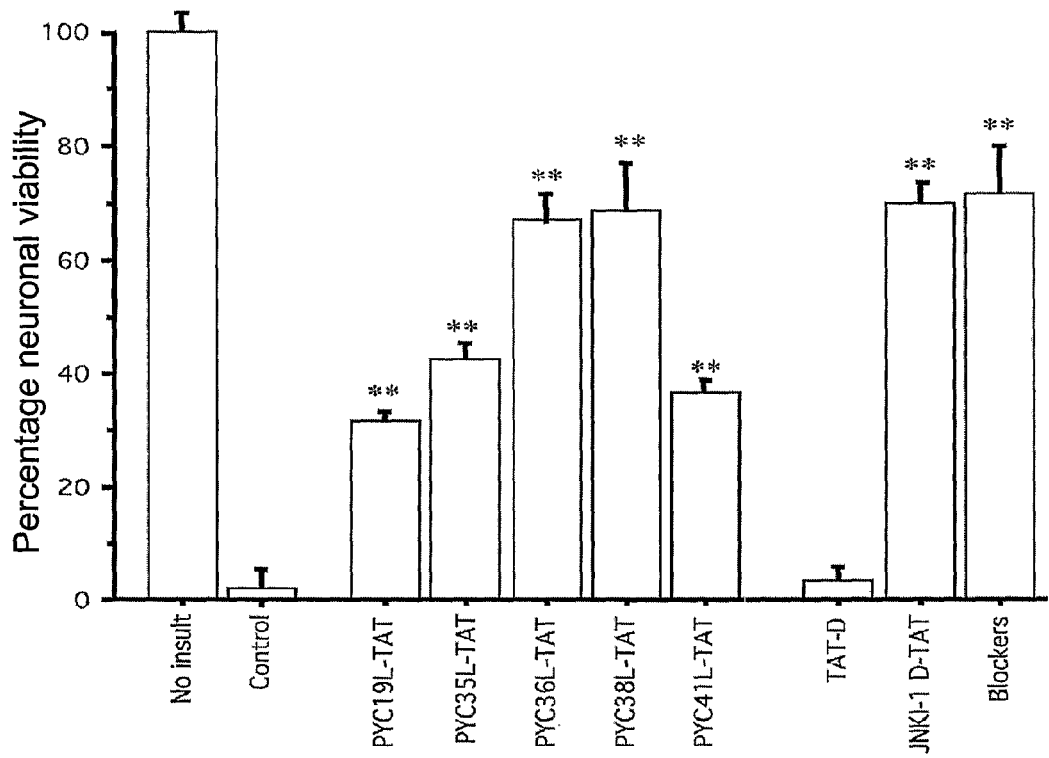
FIG. 1 is a graphical representation showing, on the y-axis the percentages of viable neurons in culture in the presence of 5 μM extracellular concentration of the Phylomer™ peptides indicated on the x-axis (PYC19L-TAT, PYC35L-TAT, PYC36L-TAT, PYC38/39L-TAT and PYC41L-TAT) following incubation with glutamate to induce excitotoxicity. Controls consisted of neuron cultures grown without glutamate (No insult), or without added peptide (Control), TAT-D peptide (TAT-D), JNK1-1D-TAT peptide (JNK1-1D-TAT), or neuron cultures incubated with a mixture of glutamate receptor inhibitors (Blockers). MTS data were expressed as percentage neuronal viability with no insult control taken as 100% viability and insult control as 5% viability (mean±SEM; n=4; *p<0.005; **p<0.0001).
Figure 2:
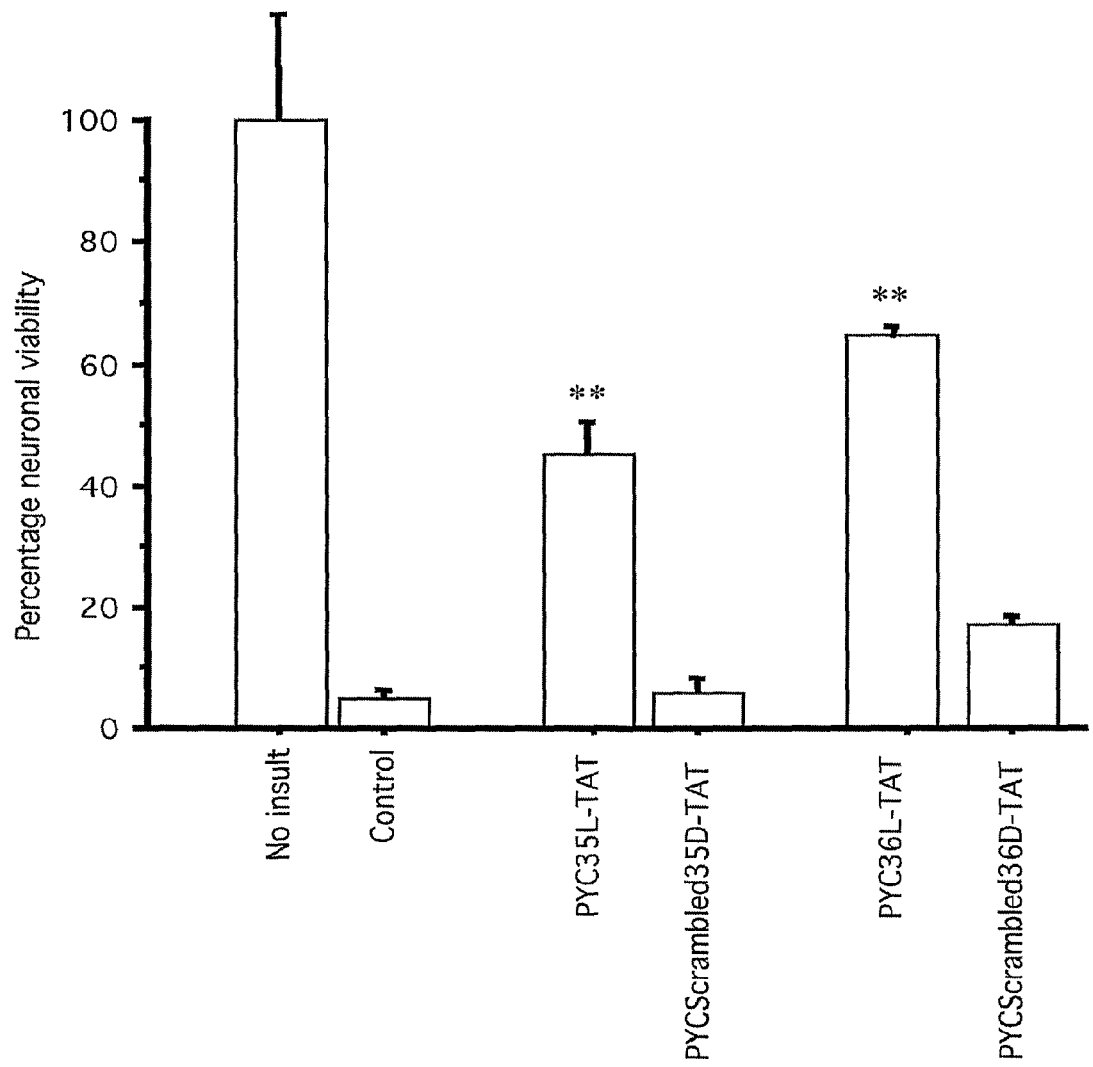
FIG. 2 is a graphical representation showing, on the y-axis the percentages of viable neurons in culture in the presence of 5 μM extracellular concentration of the retroinverted Phylomer™ peptides indicated on the x-axis (PYC35L-TAT, PYC35L-Scram-TAT, PYC36L-TAT and PYC36L Scram-TAT) following incubation with glutamate to induce excitotoxicity. Controls consisted of neuron cultures grown without glutamate (No insult), or without added peptide (Control), or JNK1-1D-TAT peptide (JNK1-1D-TAT). Data show reduced neuroprotection when the Phylomer™ sequences were scrambled. MTS data were expressed as percentage neuronal viability with no insult control taken as 100% viability and insult control as 5% viability (mean±SEM; n=4; *p<0.005; **p<0.0001).

Screening of Phylomer™ peptides in the glutamate excitotoxicity model indicated that the peptides designated PYC19L-TAT, PYC35L-TAT, PYC36L-TAT, PYC38/39L-TAT and PYC41L-TAT display neuroprotective activity (FIG. 1). Following glutamate excitotoxicity, the peptides increased neuronal viability from 2-5% basal level, to 32% for PYC19L-TAT, 42% for PYC35L-TAT, 64% PYC36L-TAT, 69% for PYC38/39L-TAT, and 38% for PYC41L-TAT. The positive peptide control JNKI-1 D-TAT increased neuronal viability to 75%. In contrast, TAT peptide alone or scrambled Phylomer™ peptides i.e., PYC35D Scram-TAT or PYC36D Scram-TAT, failed to provide neuroprotection in the glutamate model (FIG. 2).

Figure 3:
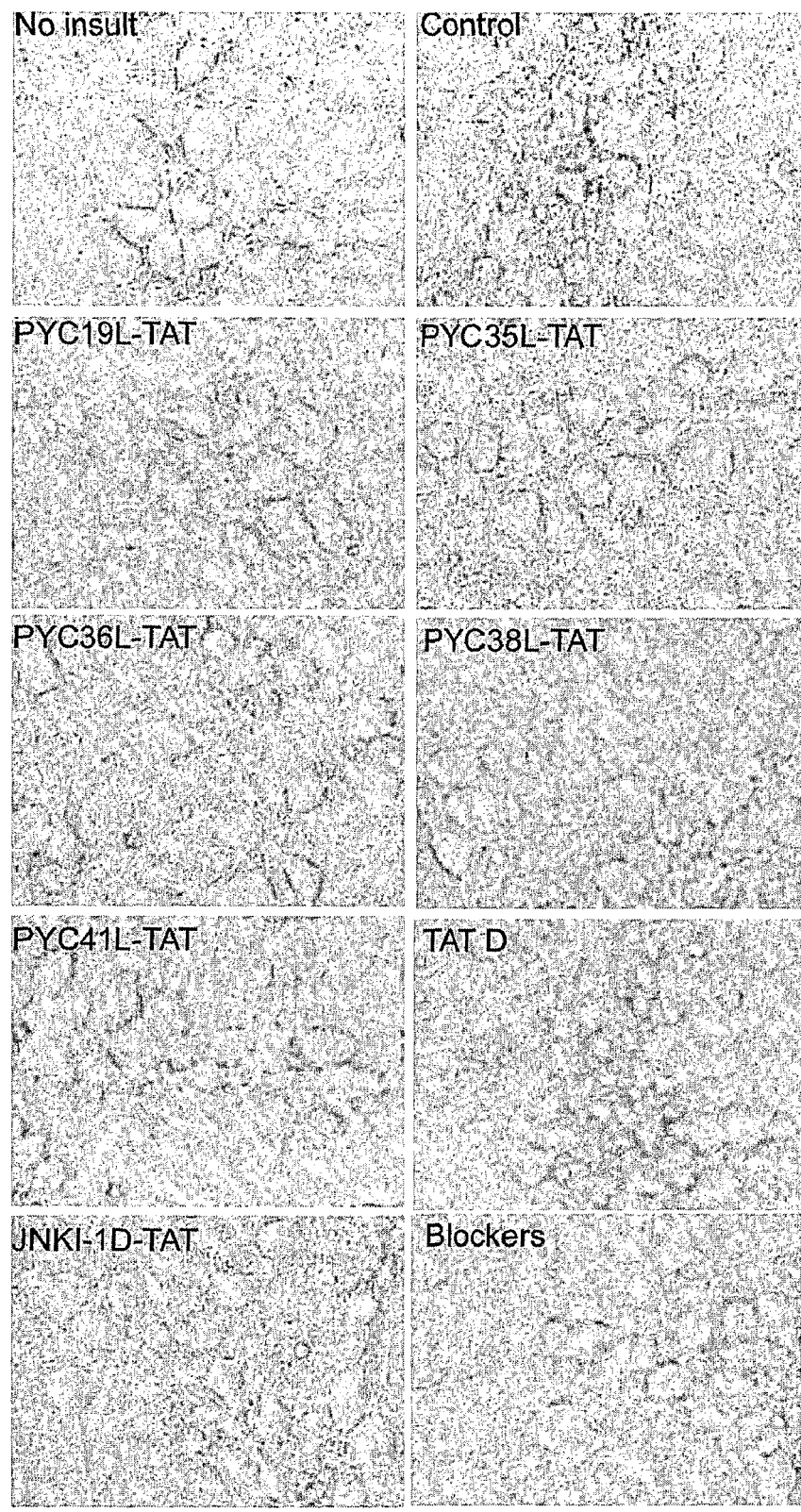
FIG. 3 shows copies of photomicrographs of neurons from cultures grown without glutamate (No insult), or incubated with glutamate in the presence of the Phylomer™ peptides (PYC19L-TAT, PYC35L-TAT, PYC36L-TAT, PYC38/39L-TAT and PYC41L-TAT), a TAT-D peptide (TAT-D), the JNK1-1D-TAT peptide (JNK1-1D-TAT), or without added peptide (Control), or with a mixture of glutamate receptor inhibitors (Blockers), as indicated in the top right of each panel. Significantly higher neuronal viability was observed for cultures not receiving glutamate, or receiving glutamate and incubated with the Phylomer™ peptides compared to TAT-D peptide (TAT-D), or no added peptide. Magnification ×200.

Neuronal viability correlated with morphological assessment observed by light microscopy (FIG. 3). At one hour post-glutamate exposure, neurons in untreated cultures and cultures treated with control peptides (TAT, PYC35D Scram-TAT, PYC36D Scram-TAT, PYC35D, PYC36D) displayed cellular rounding, and, by 18 hours post-exposure, few neurons (2-5%) appeared intact and viable. In contrast, most neurons in cultures treated with neuroprotective AP-1 signaling inhibitory peptides e.g., PYC19L-TAT, PYC35L-TAT, PYC36L-TAT, PYC38/39L-TAT, PYC41L-TAT). Or with the positive control peptide designated JNKI-1 D-TAT, or with glutamate receptor inhibitor, did not begin to round and survived glutamate excitotoxicity.

The neuroprotective Phylomer™ peptides also increased neuronal survival in a dose dependent fashion following glutamate excitotoxicity (FIG. 4). For example, an extracellular concentration of 1 µM PYC36L-TAT provided a significant level of neuroprotection, and the same extracellular concentration of the peptides PYC19L-TAT, PYC38/39L-TAT and PYC41L-TAT provided a neuroprotective trend. At an extracellular concentration of 2 µM, peptides PYC38/39L-TAT and PYC41L-TAT provided significant neuroprotection, and peptides PYC19L-TAT and PYC35L-TAT exhibited a neuroprotective trend. At extracellular concentrations of 5 µM and 10 µM, all five peptides provided significant neuroprotection.

Dose response curves showing the neuroprotective efficacies of L- and D-isoforms of these Phylomer™ peptides demonstrate that the D-isoforms are more potent (FIGS. 4a-e).

For example, an extracellular concentration of 1 µM PYC19D-TAT or PYC19L-TAT provides significant neuroprotection (FIG. 4a), however at higher concentrations, PYC19D-TAT clearly provides enhanced neuroprotection. In addition, at 5 µM, neuronal survival increased from 32% using PYC19L-TAT to 68% using the retroinverted form PYC19D-TAT.

Similar results were also obtained for PYC35-TAT peptide (FIG. 4b), wherein 500 nM PYC35D-TAT provided significant neuroprotection, compared to a requirement for 2 µM or greater concentration of PYC35L-TAT to provide significant neuroprotection; and neuronal survival at 5 µM extracellular peptide concentration increasing from 42% using PYC35L-TAT to 59% when using PYC35D-TAT.

Figure 4A:
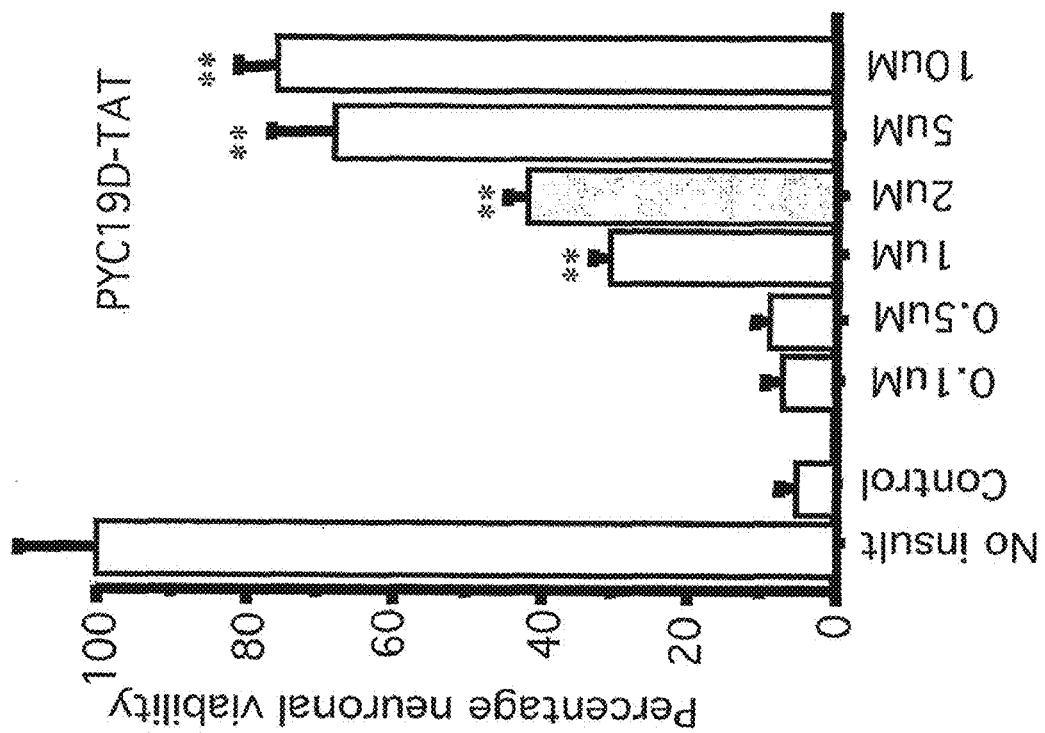
FIG. 4A provides graphical representations showing, on the y-axis the percentages of viable neurons in culture in the presence of 0.1-10 μM extracellular concentration of the Phylomer™ peptides PYC19L-TAT and PYC19D-TAT following incubation with glutamate to induce excitotoxicity. Controls consisted of neuron cultures grown without glutamate (No insult), or without added peptide (Control). MTS data were expressed as percentage neuronal viability with no insult control taken as 100% viability and insult control as 5% viability (mean±SEM; n=4; * p<0.005; **p<0.0001).
Figure 4A:
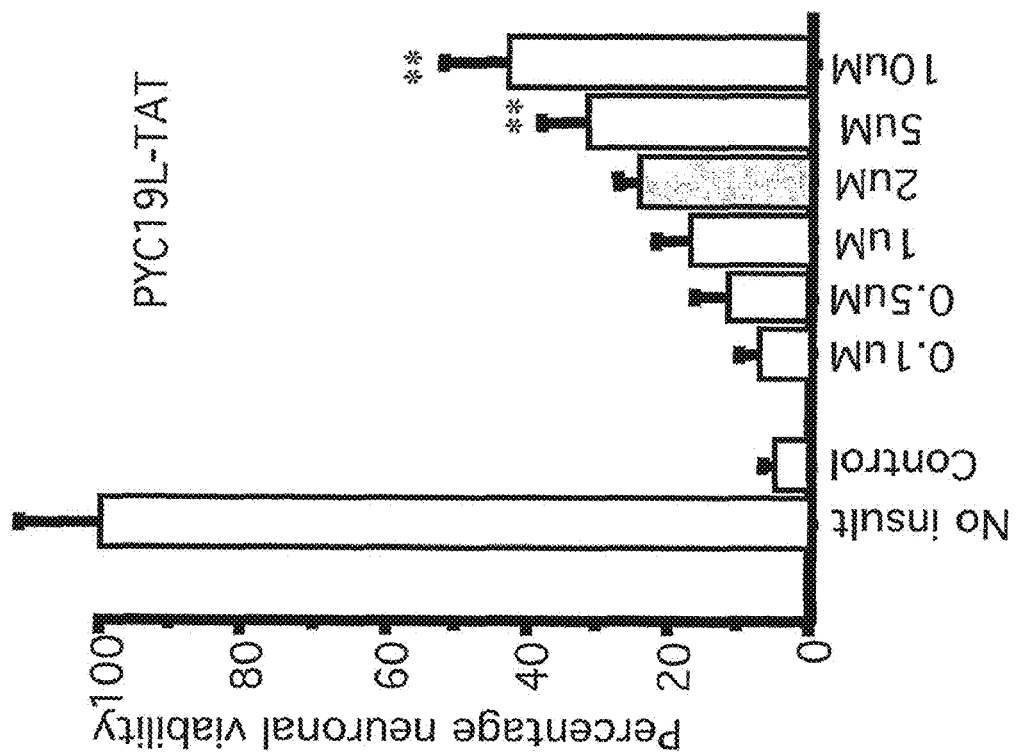
Figure 4B:
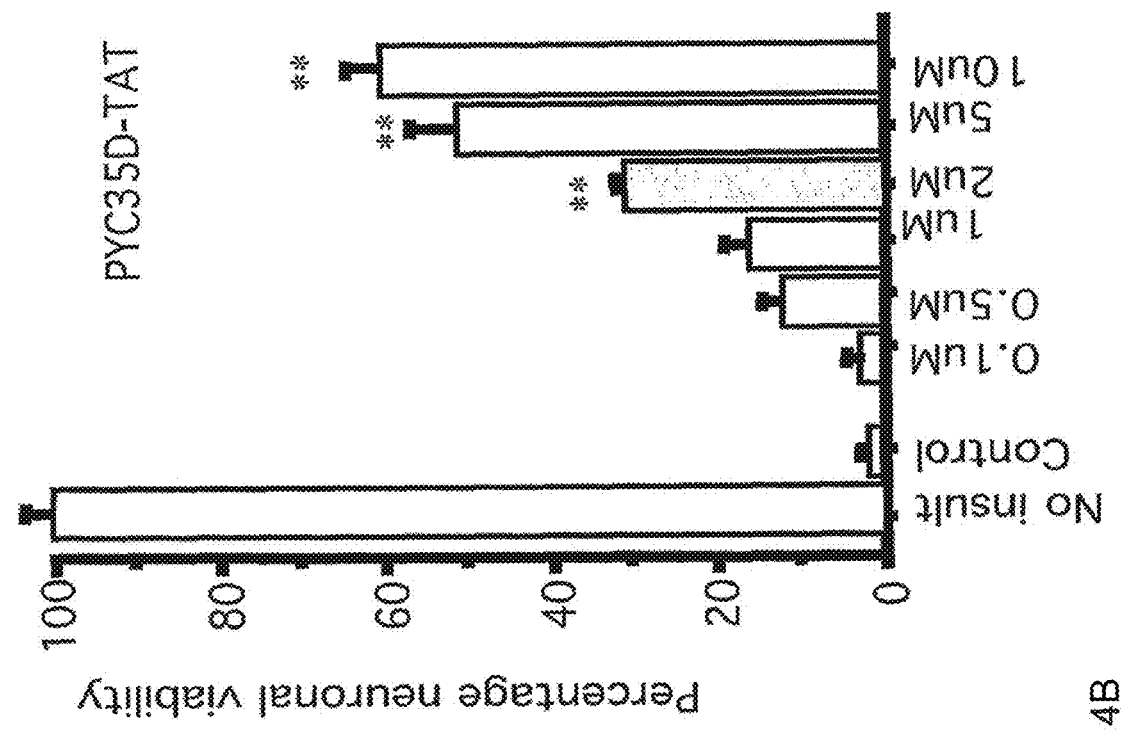
FIG. 4B provides graphical representations showing, on the y-axis the percentages of viable neurons in culture in the presence of 0.1-10 μM extracellular concentration of the Phylomer™ peptides PYC35L-TAT and PYC35D-TAT following incubation with glutamate to induce excitotoxicity. Controls consisted of neuron cultures grown without glutamate (No insult), or without added peptide (Control). MTS data were expressed as percentage neuronal viability with no insult control taken as 100% viability and insult control as 5% viability (mean±SEM; n=4; * p<0.005; **p<0.0001).
Figure 4B:
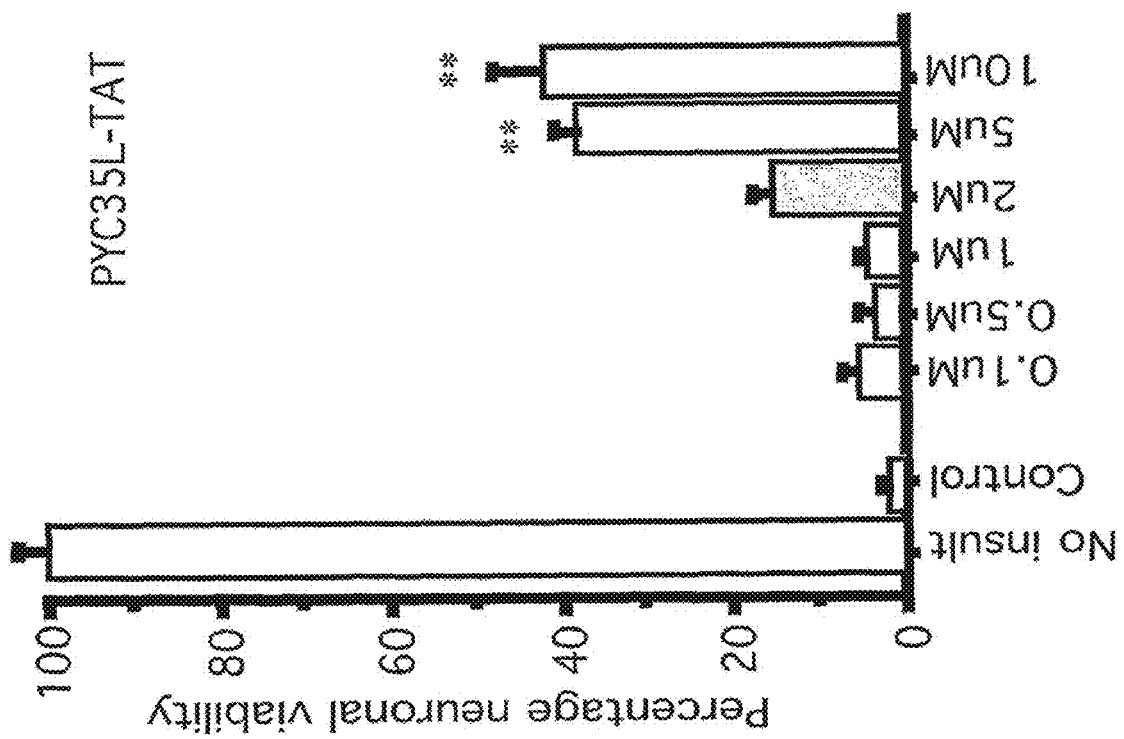
Figure 4C:
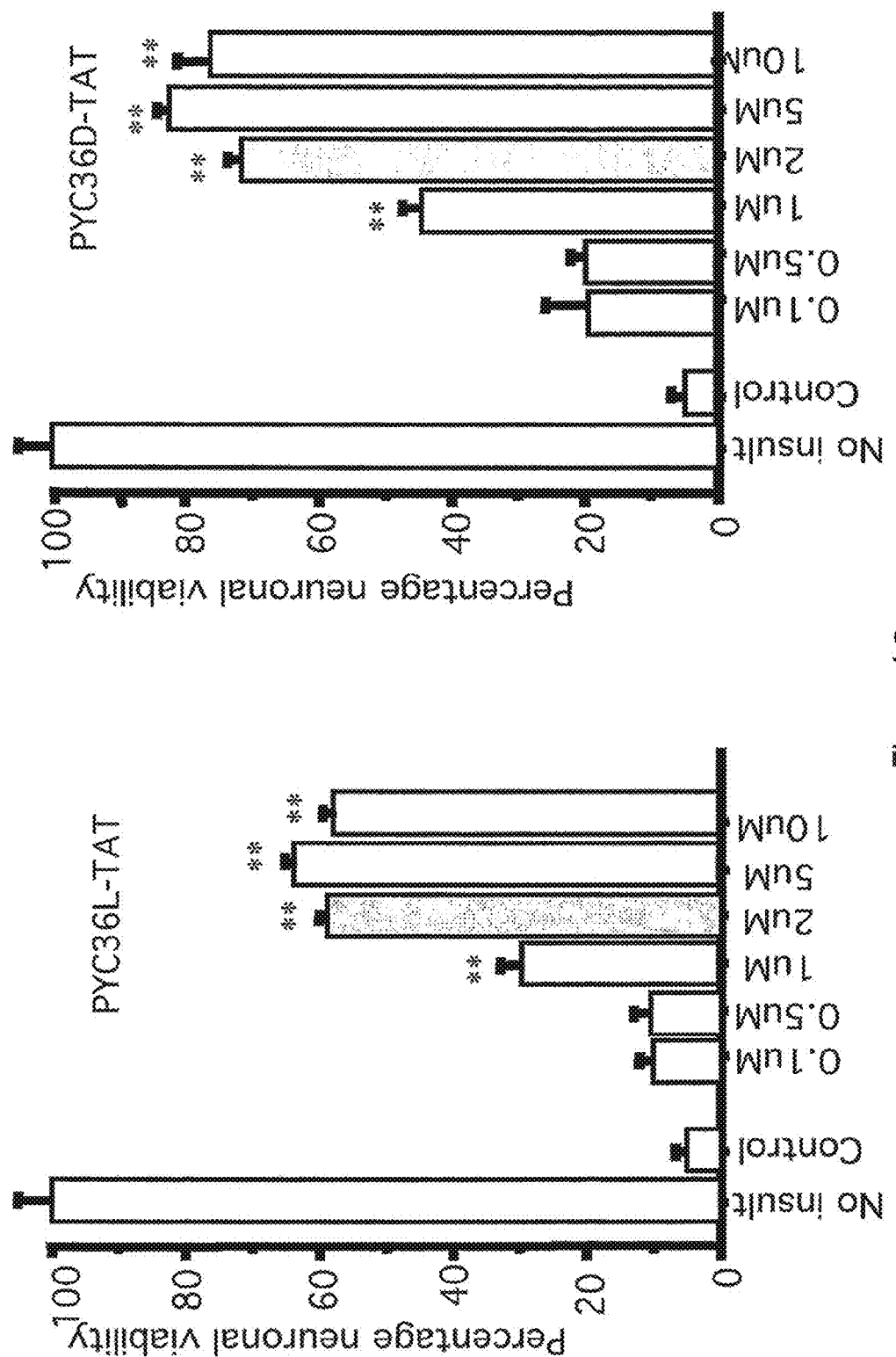
FIG. 4C provides graphical representations showing, on the y-axis the percentages of viable neurons in culture in the presence of 0.1-10 μM extracellular concentration of the Phylomer™ peptides PYC36L-TAT and PYC36D-TAT following incubation with glutamate to induce excitotoxicity. Controls consisted of neuron cultures grown without glutamate (No insult), or without added peptide (Control). MTS data were expressed as percentage neuronal viability with no insult control taken as 100% viability and insult control as 5% viability (mean±SEM; n=4; * p<0.005; 25**p<0.0001).
Figure 4D:
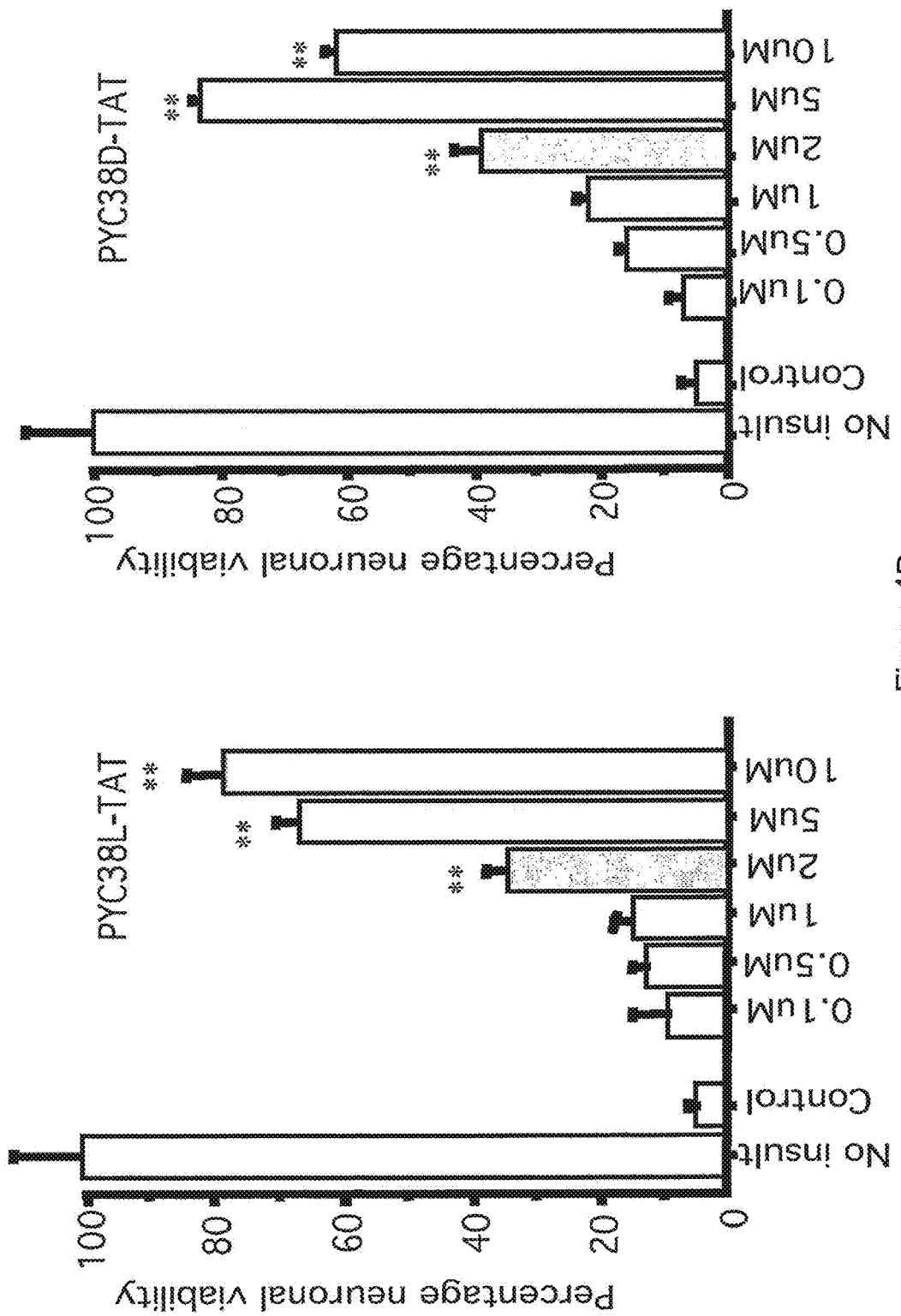
FIG. 4D provides graphical representations showing, on the y-axis the percentages of viable neurons in culture in the presence of 0.1-10 μM extracellular concentration of the Phylomer™ peptides PYC38/39L-TAT and PYC38/39D-TAT following incubation with glutamate to induce excitotoxicity. Controls consisted of neuron cultures grown without glutamate (No insult), or without added peptide (Control). MTS data were expressed as percentage neuronal viability with no insult control taken as 100% viability and insult control as 5% viability (mean±SEM; n=4; * p<0.005; **p<0.0001).

Similarly, at 5 µM extracellular peptide concentration, neuronal survival increased from 64% using PYC36L-TAT to 82% when using PYC36D-TAT (FIG. 4c). In the case of peptides PYC36L-TAT and PYC36D-TAT, whilst significant neuroprotection was achieved at 1 µM extracellular concentration for both isoforms, a significantly greater level of viability was achieved using the D-isoform, i.e., 44% for PYC36D-TAT cf. 30% for PYC36L-TAT. At lower extracellular peptide concentrations e.g., 0.1 µM and 0.5 µM, the D-isoform also displayed significant neuroprotection compared to the L-isoform.

Figure 4E:
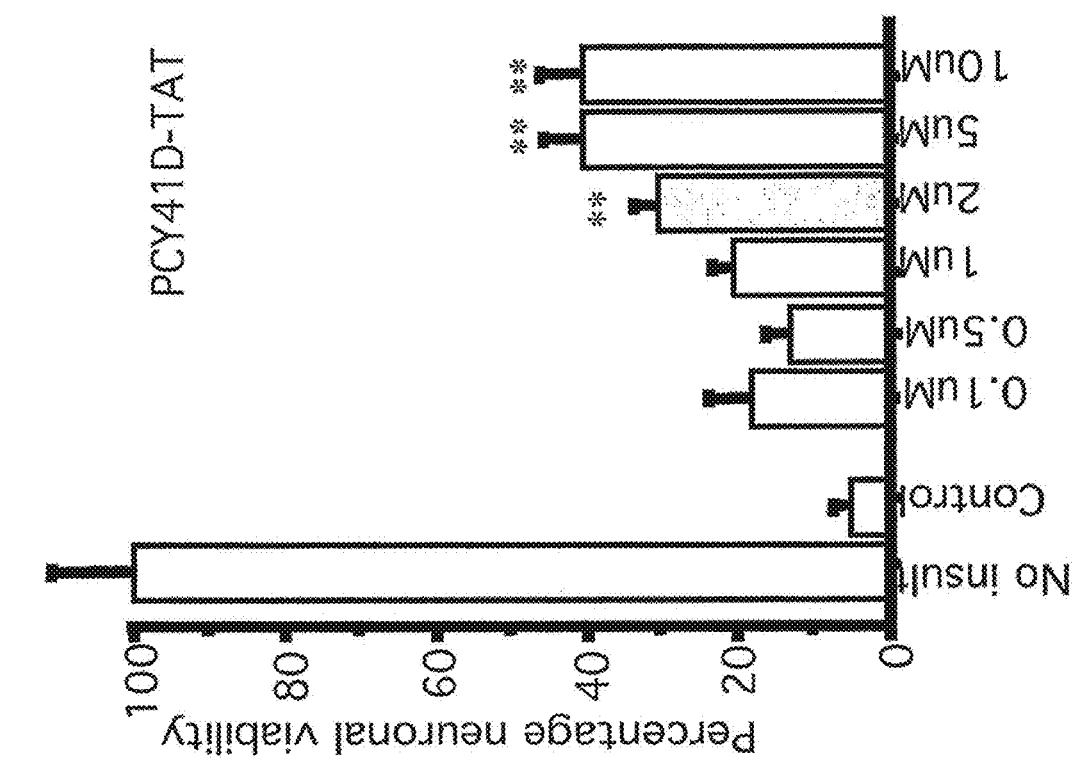
FIG. 4E provides graphical representations showing, on the y-axis the percentages of viable neurons in culture in the presence of 0.1-10 μM extracellular concentration of the Phylomer™ peptides PYC41L-TAT and PYC41D-TAT following incubation with glutamate to induce excitotoxicity. Controls consisted of neuron cultures grown without glutamate (No insult), or without added peptide (Control). MTS data were expressed as percentage neuronal viability with no insult control taken as 100% viability and insult control as 5% viability (mean±SEM; n=4; * p<0.005; **p<0.0001).
Figure 4E:
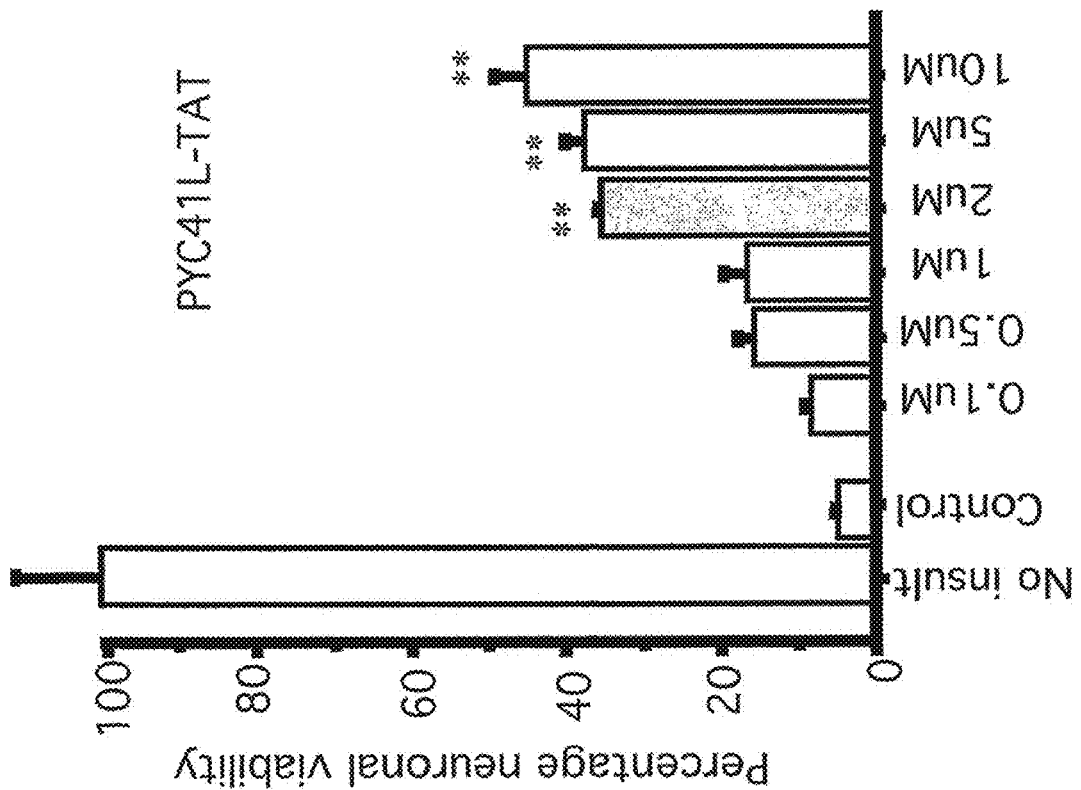

The administration of 2 µM PYC38/39L-TAT, PYC41L-TAT, PYC38/39D-TAT or PYC41D-TAT achieved an initial significant neuroprotection (FIGS. 4d,e); and at 5 µM extracellular peptide concentration, neuronal viability increased from 69% using PYC38/39L-TAT to 83% using PYC38/39D-TAT (FIG. 4d), however did not vary significantly for the peptides PYC41D-TAT and PYC41L-TAT (40% cf. 38%; FIG. 4e).

These data compare favorably with the neuronal protection conferred for the JNKI-1D-TAT peptide, which provided significant neuroprotection at an extracellular concentration of 2 µM or greater, to a maximum neuronal viability of 89% at 5 µM extracellular concentration i.e., comparable to efficacy of 5 µM PYC36D-TAT. In particular, at 1 µM concentration, the Phylomer™ peptides PYC19D-TAT, PYC36L-TAT, PYC36D-TAT and PYC38/39D-TAT at least provided greater neuroprotection than JNKI-1D-TAT; and at 2 µM concentrations the Phylomer™ peptide PYC36D-TAT provided greater neuroprotection than JNKI-1D-TAT. Moreover, 500 nM PYC35D-TAT provides significant ($p<0.0242$) neuroprotection (FIG. 4b), and 100 nM PYC36D-TAT provides significant ($p<0.0196$) protection (FIG. 4c), compared to the same concentration of JNK1-1D-TAT. In fact, the peptide JNK1-1D-TAT only exhibits significant ($p<0.0077$) neuroprotection at micromolar concentrations under these conditions.

Figure 5:
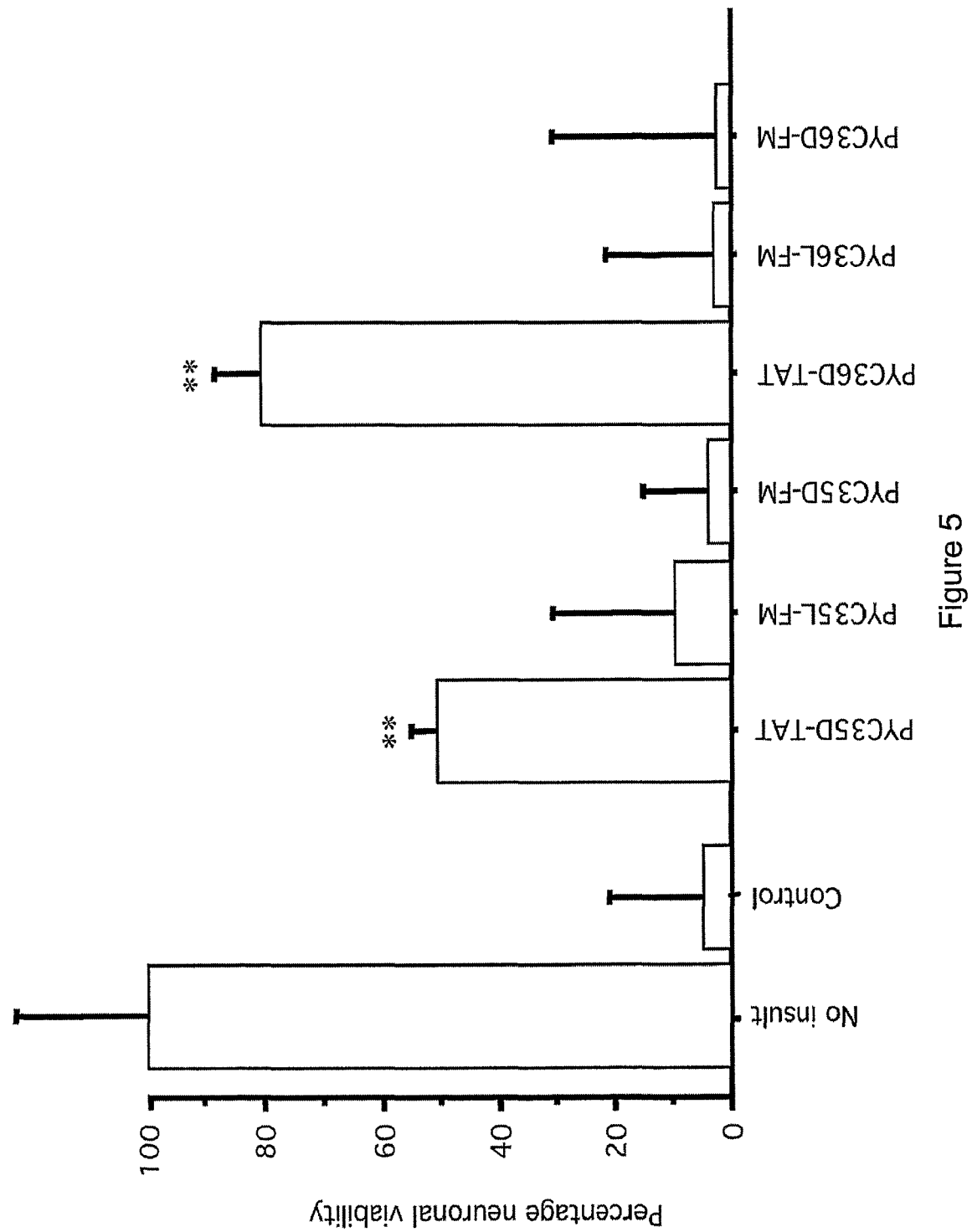
FIG. 5 provides a graphical representation showing, on the y-axis the percentages of viable neurons in culture in the presence of 5 μM extracellular concentration of the Phylomer™ peptides PYC35D-TAT, PYC35L-FM, PYC35D-FM, PYC36D-TAT, PYC36L-FM and PYC36D-FM, following incubation with glutamate to induce excitotoxicity. Controls consisted of neuron cultures grown without glutamate (No insult), or without added peptide (Control).

The efficacy of the FM and TAT transduction domains, synthesised with both L- and D-isoforms of peptides PYC35 and PYC36, were also compared (FIG. 5). Neither L-nor D-isoforms of PYC35-FM and PYC36-FM provided significant neuroprotection following glutamate excitotoxicity, compared to PYC35D-TAT and PYC36D-TAT.

Peptides were also administered over a time course, for peptides PYC35D-TAT and PYC36D-TAT. In particular, these peptides were added to neuronal cultures prior to, immediately post (0 min), or at 15, 30, 45 or 60 minutes after glutamate exposure (FIG. 6). Data indicate that administration of either PYC35D-TAT or PYC36D-TAT prior to glutamate exposure was neuroprotective.

Peptide treated and control cultures were also assessed for neuronal intracellular $Ca^{2+}$ influx following glutamate exposure. Cultures treated with peptides PYC35D-TAT or PYC36D-TAT and exposed to glutamate did not block neuronal $Ca^{2+}$ entry. Rather, there was a rapid influx of $Ca^{2+}$, with measured amplitudes of 361 and 442 respectively (FIG. 7). Similarly, neurons in control cultures exposed to glutamate also underwent rapid increases in intracellular $Ca^{2+}$ with an amplitude of 496. In contrast, neuronal cultures treated with glutamate blockers MK801/CNQX exposed to glutamate inhibited intracellular $Ca^{2+}$ influx with a nominal amplitude of 26 (FIG. 7).

In summary, this study has validated five AP-1 signaling inhibitory peptides that block neuronal death following glutamate excitotoxicity. As both c-Jun activation and glutamate excitotoxicity are linked to neurodegenerative disorders, cerebral ischemia, traumatic brain injury, epilepsy, Parkinson's Disease, Alzheimer's Disease and Amyotrophic Lateral Sclerosis (ALS), these peptides are these peptides have utility for the development of compositions for the treatment of such neurological disorders. In vivo studies will validate these peptides as neuroprotectants in animal models for various neurodegenerative disorders.

EXAMPLE 4

Peptides that Inhibit AP-1 Signaling are Neuroprotective Following N-Methyl-D-Aspartate (NMDA) Excitotoxicity in Primary Cortical Neuronal Cultures NMDA-induced excitotoxicity specifically targets the NMDA glutamate receptor to induce excitotoxicity and induces an acute form of cell death in neuronal cultures.

Materials & Methods

1. Peptides

Peptides used to determine rescue of neurons from NMDA-induced excitotoxicity were PYC35D-TAT and PYC36D-TAT as shown in Table 1.

2. NMDA Excitotoxicity

The procedure for determining NMDA excitotoxicity in neuron culture is similar to the procedure for determining glutamate excitotoxicity (Example 3), however a final NMDA concentration of 200 µM is used, and the insult time is for 15 minutes.

Results

The neuroprotective Phylomer™ peptides PYC35D-TAT and PYC36D-TAT, which have been shown herein to rescue neurons from glutamate excitotoxicity, also protect cortical neurons against NMDA-induced excitotoxicity (FIG. 8; $p<0.0001$ in both cases).

EXAMPLE 5

Peptides that Inhibit AP-1 Signaling Reduce Cell Death in an In Vitro Ischemia Cell Model The ability of retroinverted Phylomer™ peptides to protect cultured cortical neurons in an in vitro model of ischemia known as Oxygen Glucose Deprivation (OGD). This model involves inducing an energy crisis in neuronal cultures by transiently-depriving the neurons of oxygen and glucose for 35 minutes, which are essential for normal cellular metabolism and the main energy substrates that are depleted during cerebral ischemia.

Materials and Methods

1. Determination of Ischemia In Vitro

Ischemia in vitro is determined in glass wells, because plastic wells store oxygen, by removing media from neuronal cultures in glass wells and washing in 315 µl balanced salt solution (BSS; mM: 116 NaCl, 5.4 KCl, 1.8 CaCl2, 0.8 MgSO4, 1 NaH2PO4; pH 7.3) and re-adding 50 µl of BSS containing 25 mM 2-deoxy-D-glucose (ICN). Following incubation of neuronal cultures in an anaerobic chamber (Don Whitely Scientific, England) for 35 minutes, the media from each well are removed and replaced with 50 µl BSS and 50 µl of Neurobasal/2% $N_2$ supplement (Invitrogen) before placing culture wells into a $CO_2$ incubator. Control neuronal cultures received the same BSS wash procedures and media additions as ischemic cultures, but were maintained in a $CO_2$ incubator. After a further 24 h, neuronal viability was assessed using the MTS assay as described in the preceding examples.

Results

The results from this assay indicated that the retroinverted Phylomer™ peptides PYC35D-TAT and PYC36D-TAT are protective ($p<0.0001$), when they were added before or immediately after OGD (FIG. 9).

EXAMPLE 6

Peptides that Inhibit AP-1 Signaling have Half-Lives Sufficient for Therapy of Acute Ischemic Events Having established the biologically efficacy of the retro-inverso forms of the neuroprotective Phylomer™ peptides, their in vitro stabilities were assessed.

Materials and Methods

1. In Vitro Plasma Stability

A stock solution of 200 µg/ml of peptide in PBS was diluted into 1.5 ml of human plasma or PBS to achieve a final concentration of 10 µg/ml. Of this solution, 50 µl was then dispensed into 200 µl Max Recovery tubes (Axygen Scientific) in triplicate for each time point needed in the study. The tubes were incubated at 37° C. and at the appropriate time point, they were removed from the incubator and 150 µl of extraction solution (75% acetonitrile/25% water+2% formic acid) was added. The tubes were vortexed for 15 sec and then centrifuged at 11,000 RPM for 5 mins at 4° C. Then, 100 µl of the supernatant was transferred into HPLC vials for analysis.

A fixed mobile phase was used so that all of the different charged species of peptide would elute at the same time, allowing a mass measurement of non-degraded material. Injection volume: 10 µl; Column: Phenomenex Aqua C18 5 µM 150 mm×4.6 mm; Flow: 0.8 ml/min; 85% Mobile phase A: 4% formic acid in nanopure water; 15% Mobile phase B: acetonitrile; RT: 1.3 minutes; Stop time: 3.0 minutes. Mass Spectrometer: MS-03 LC/MSD Trap XCT Ultra.

2. In Vivo Plasma Stability/Clearance Rate

Male Sprague-Dawley rats (276-310 g) were dosed with peptide by i.v injection via the jugular vein. The calculated dose for each animal was 3 mg/kg of body weight and each isoflurane anaesthetised animal received dosing volumes of 0.1 ml/100 g of body weight of a 3 mg/ml solution. The remaining dosing solutions were subjected to a similar protocol as the solutions that were administered to the animals and were collected pre-labeled Maxymum Recovery (Axygen Scientific) low binding tubes, ready for quantification. Blood samples (0.2 ml) were collected just prior to dosing (pre-dose) and at various time points post-dosing according to the experimental schedule. Blood samples were collected from the jugular vein from the anaesthetized and transferred into 0.5 ml pre-labeled EDTA micro-centrifuge tubes and placed on ice. The tubes were then centrifuged for 5 mins at 3,000 RPM in a bench top microcentrifuge (4° C.). The plasma was transferred to pre-labeled 1.7 ml tubes, stored in a −80° C. freezer prior to analysis by LC-MS.

Analysis: Sample Preparation: 50 µl of plasma was added to 150 µl of precipitating solvent (75% acetonitrile/25% water+2% formic acid) and vortexed for 15 sec. The solution was centrifuged at 11,000 rpm at 4° C. for 5 mins. 100 µl of the supernatant was transferred to a HPLC vial for quantification.

The HPLC conditions were as follows: Injection: 10 µl; Column: Phenomenex Aqua C18 5 µM 150 mm×4.6 mm; Flow: 0.7 ml/min; Mobile phase A: 4% formic acid in nanopure water., Mobile phase B: acetonitrile., Retention time: 2.2 mins., Mass Spectrometer: MS-03 LC/MSD Trap XCT Ultra.

Results

An analysis of the full-length Phylomer™ peptides remaining in freshly drawn human plasma using a liquid chromatography/Mass Spectrometry (LC-MS) assay showed that PYC35D-TAT and PYC36D-TAT have half-lives of more than 12 hours (FIG. 10). To test in vivo clearance rates, these Phylomer™ peptides were injected into rats and, at various time points, blood samples were taken and analysed to quantify the remaining full-length peptide by LC-MS. Peptides PYC35D-TAT and PYC36D-TAT had in vivo half-lives of 35 minutes and 100 minutes, respectively (data not shown).

These in vivo half-lives are in a range which would allow application in an acute treatment setting. This is appropriate for emergency therapy for stroke or traumatic brain injury, being comparable with that of tissue plasminogen activator (tPA), the leading emergency stroke therapy, which has an in vivo half life of a few minutes in rabbit blood. The biological efficacy of these peptides ex vivo and in vivo establish their suitability for acute therapeutic regimes, without necessarily the need for prior affinity maturation.

EXAMPLE 7

Peptides that Inhibit AP-1 Signaling are Neuroprotective in a Rat Model of Global Cerebral Ischemia As PYC35D-TAT and PYC36D-TAT were active ex vivo in neuroprotection assays, and exhibited long half-lives in vivo, their activities were tested in a rat model of global cerebral ischemia. For comparison, the JNK1-1D-TAT peptide was included as a control.

Materials and Methods

This study was approved by the Animal Ethics Committee of the University of Western Australia. The 2 vessel common carotid occlusion with hypotension model was used to induce global cerebral ischemia in 8-10 week old adult male Sprague-Dawley rats (Miles et al., 2001; Zhu et al., 2004). During the procedure, both cranial and rectal temperatures were measured via a thermocouple (Physitemp, New Jersey, USA), and were maintained at 37±0.2° C. with a heating fan and pad. Rats Were anesthetized with halothane/27% $O_2$/balanced $NO_2$ and ventilated before, during and for at least 15 min after global cerebral ischemia. Cerebral ischemia was recorded from the time the EEG became iso-electric and was maintained for a duration of 8 minutes. Blood pressure was reduced by exsanguination to a maintenance level between 35 and 40 mmHg during ischemia. Ten minutes before and 15 min after the ischemic insult, $PaO_2$, $PaCO_2$ and pH were measured with a pH/blood gas analyzer (ABL5 Radiometer, Copenhagen, Denmark).

Peptide doses of 11 nmoles were administered via injection to the cerebral ventricle 1 hour post ischemia. Control animals consisted of sham-operated animals and ischemic animals treated with saline. Post-surgery animals were given 5 ml of warmed 0.9% NaCl by SC injection and placed in a clean cage where rectal temperature was monitored and maintain between 37.0 and 38.0° C. with heating/cooling fan as required.

At 7 days post-ischemia animals were killed and CA1 neuronal survival was assessed by counting the number of normal-appearing pyramidal neurons per high-power field (400×) in 1000 µm segments in the medial, intermediate and lateral sections of the hippocampal CA1 region (bregma section −3.8). CA1 counts were expressed as a percentage of sham values, which was taken as 100% neuronal survival. Neuronal cell counts were conducted by an observer who was blinded to the experimental protocol.

Physiological parameters (blood pressure, gases, glucose, pH, cranial temperature) and CA1 neuronal counts were analyzed by ANOVA. If significant variance was observed post hoc Bonferroni/Dunn pair wise comparisons were made. All data are presented as mean±standard deviation. A value of $P<0.05$ was considered significant.

Results

Whilst not optimised for dosage (dose chosen to match published dosage of the D-JNKI positive control), peptides PYC35D-TAT and PYC36D-TAT blocked neuronal cell death in this model when injected intracerebroventricularly, demonstrating their efficacy in vivo (FIG. 11).

EXAMPLE 8

Peptides that Inhibit AP-1 Signaling Also Inhibit Neuronal Apoptosis as Determined by Loss of MAP2 Immunoreactivity The ability of AP-1 signaling-inhibitory peptides to inhibit neuronal apoptosis was assessed by loss of MAP2 immunoreactivity in a focal model of traumatic brain injury (Chung et al., *J. Neuroscience* 23, 3336-3342, 2003; King et al., *Neuropathol Appl Neurobiol.* 27, 115-126, 2001).

Materials and Methods

Rats were subjected to acute cortical injury as previously described by Chung et al., *J. Neuroscience* 23, 3336-3342 (2003) and King et al., *Neuropathol Appl Neurobiol.* 27, 115-126 (2001). Briefly, male 240 g Hooded-Wistar rats were deeply anaesthetized using Isofluorane (2-3%) and were given an analgesic (Meloxycam, 40 mg/kg), by subcutaneous injection. Animals were immobilized in a Stoelting stereotactic frame, and a 21 gauge blunt Hamilton syringe was inserted into the Par1 region of the somatosensory cortex to a depth of 2 mm and was left in place for 10 minutes. Then, 0.5 µl of 5 µM peptide was administered through the syringe at a rate of 0.05 µl/min. Peptide (10 µl) was applied to 1 $mm^2$ of Gelfoam, which was implanted before suturing. At 1 day post-injury (PI), rats were deeply anaesthetized with sodium pentobarbital (60 mg/kg), then perfused transcardially with a 4% paraformalydehyde and 4% sucrose fixative solution in 0.01M PBS. Brains were removed and cryoprotected in 18% and 30% sucrose solutions, respectively and 40 µm coronal sections were collected serially through the injury site for immunohistochemical labelling. All animal procedures were approved by the University of Tasmania Animal Ethics Committee (Permit A008878).

Sections were labelled with Nissl Red, Nuclear Yellow and anti-MAP2 to allow a quantitative assessment of neuronal loss around the lesion. Sections from the lesion centre and 200 µm anterior and posterior to the centre of the injury, at layer III of the neocortex were included in the analysis and the area of MAP2 loss was scored by blinded observers. Three sections from each of three animals were examined for each treatment and significance assessed by ANOVA and post-hoc comparison (Tukey test).

All data are presented as mean±standard error. A value of P<0.05 was considered significant.

Results

In this model, PYC35D-TAT was neuroprotective when compared with a negative control peptide designated PYC35D Scram-TAT in which the Phylomer™ peptide moiety was scrambled (p<0.05) (FIGS. 12,13). Peptide PYC35SD-TAT provided greater neuroprotection in this head injury model than the peptide JNK1-1D-TAT (FIG. 12).

Together, these studies established that these AP-1 signaling inhibitory Phylomer™ peptides provide neuroprotective activity both in vitro and in vivo, and are promising leads for therapeutic development, especially for acute treatment settings such as in migraine, stroke, acute head trauma injury and organ reperfusion injury.

We claim:

1. A neuroprotective AP-1 signaling inhibitory peptide that is a fusion peptide comprising a protein transduction domain having the amino acid sequence of SEQ ID NO: 1 and a peptide having the sequence of SEQ ID NO:54 wherein the protein transduction domain and the peptide are separated by a linker, or a retroinverted analog of said fusion peptide comprising one or more D-amino acids.

2. The neuroprotective AP-1 signaling inhibitory peptide of claim 1 wherein said inhibitory peptide provides enhanced inhibition of glutamate excitotoxicity in vitro relative to an equimolar concentration of the peptide JNK1-1D-TAT (SEQ ID NO: 68).

3. The neuroprotective AP-1 signaling inhibitory peptide of claim 2 wherein said inhibitory peptide significantly inhibits glutamate excitotoxicity at a concentration of less than about 2 μM.

4. The neuroprotective AP-1 signaling inhibitory peptide of claim 1 wherein said inhibitory peptide comprises a sequence selected from the group consisting of SEQ ID NO:56 and SEQ ID NO:57.

5. The neuroprotective AP-1 signaling inhibitory peptide of claim 1 wherein said inhibitory peptide protects neurons from cell death in vivo.

6. The neuroprotective AP-1 signaling inhibitory peptide of claim 1 wherein the linker comprises 1 to 6 glycine residues or other amino acids of low immunogenicity.

7. A neuroprotective composition comprising (i) an amount of a neuroprotective AP-1 signaling inhibitory peptides according to claim 1 sufficient to reduce, delay or prevent neuronal apoptosis and/or necrosis in an animal; and (ii) a suitable carrier or excipient for application to the central nervous system of the animal.

8. The neuroprotective composition of claim 7 comprising a plurality of said neuroprotective AP-1 signaling inhibitory peptides.

9. The neuroprotective composition of claim 7 further comprising JNK inhibitory peptide JNK1-1D-TAT (SEQ ID NO: 68).

10. A method for preventing or delaying neuronal cell death in a subject having cerebral ischemia, said method comprising administering an AP-1 signaling inhibitory peptide according to claim 1 or a composition comprising said peptide to a subject in need of treatment.

11. The method of claim 10 comprising repeated administration of the peptide or composition.

* * * * *